United States Patent
Phenix et al.

(10) Patent No.: US 11,826,435 B2
(45) Date of Patent: Nov. 28, 2023

(54) CONDURITOL AZIRIDINE DERIVATIVES AND USES THEREOF

(71) Applicants: University of Saskatchewan, Saskatoon (CA); Daniel Tesolin, Thunder Bay (CA)

(72) Inventors: Christopher Phenix, Saskatoon (CA); Daniel Tesolin, Thunder Bay (CA); Morshed Chowdhury, Saskatoon (CA); Shusheng Wang, Saskatoon (CA)

(73) Assignee: UNIVERSITY OF SASKATCHEWAN, Saskatoon (CA)

( * ) Notice: Subject to any disclaimer, the term of this patent is extended or adjusted under 35 U.S.C. 154(b) by 0 days.

(21) Appl. No.: 16/756,872

(22) PCT Filed: Oct. 19, 2018

(86) PCT No.: PCT/CA2018/051323
§ 371 (c)(1),
(2) Date: Apr. 17, 2020

(87) PCT Pub. No.: WO2019/075574
PCT Pub. Date: Apr. 25, 2019

(65) Prior Publication Data
US 2021/0052752 A1     Feb. 25, 2021

Related U.S. Application Data

(60) Provisional application No. 62/574,575, filed on Oct. 19, 2017.

(51) Int. Cl.
*A61K 51/04*     (2006.01)
*C07D 401/12*    (2006.01)

(52) U.S. Cl.
CPC ........ *A61K 51/0455* (2013.01); *C07D 401/12* (2013.01)

(58) Field of Classification Search
CPC .......................... A61K 51/0455; C07D 401/12
USPC ....................................................... 424/1.89
See application file for complete search history.

(56) References Cited

U.S. PATENT DOCUMENTS

2013/0143228 A1*  6/2013  Aerts ................... C07D 303/36
                                                                435/7.1

FOREIGN PATENT DOCUMENTS

KR    20120107030 A  *  2/2012
WO    2019075574 A1     4/2019

OTHER PUBLICATIONS

Tesolin Thesis-Lakehead University, 2017, 1-109 (Year: 2017).*
Adams et al. Chem. Commun. 2015, 51, 11390-11393. (Year: 2015).*
Phenix et al. PNAS, 107, 2010, 10842-10847. (Year: 2010).*
Way et al. Chem. Commun. 2015, 51, 3838-3841. (Year: 2015).*
Glaser et al. Bioconjugate Chem. 2007, 18, 989-993. (Year: 2007).*
Kuhnast et al. Bioconjugate Chem. 2004, 15, 617-627 (Year: 2004).*
Zhang et al. Curr. Top. Med. Chem. 2007, 7, 1817-1828. (Year: 2007).*
Schroder et al. Eur. J. Org. Chem. 2016, 4787-4794. (Year: 2016).*
Ogawa et al. Bioorg. Med. Chem. Lett. 1999, 9, 1493-1498. (Year: 1999).*
Walvoort et al. Chem Commun. 2012, 48, 10386-10388. (Year: 2012).*
Witte et al. Nat. Chem. Biol. 2010, 6, 907-913. (Year: 2010).*
International Search Report and Written Opinion of corresponding International Application No. PCT/CA2018/051323 dated Feb. 7, 2019, 9 pages.
Tesolin, D., The Development of Molecular Probes for the in vitro and in vivo Study of Glucocerebrosidase, Lakehead University Canada, Mar. 31, 2017. 108 pages.
Adams, B.T. et al., N-Alkylated aziridines are easily-prepared, potent, specific and cell-permeable covalent inhibitors of human B-glucocerebrosidase, Chem. Comm., vol. 51, No. 57, pp. 11390-11393, Jul. 21, 2015.
Jiang, J. et al., Comparing Cyclophellitol N-Alkyl and N-Acyl Cyclophellitol Aziridines as Activity-Based Glycosidase Probes, Chem. Eur. J., vol. 21, No. 30, pp. 10861-10869, Jul. 1, 2015.
Nakata, M. et al., A family of cyclophellitol analogs: Synthesis and evaluation, J. Antibiotics, vol. 46, No. 12, pp. 1919-1922, Jan. 1, 1993.
Phenix, C et al., Towards PET Tracers for Imaging beta-glucocerebrosidase activity, 52nd American Chemical Society, National Meeting and Exposition, Philadelphia, PA, United States, Aug. 21-25, 2016.
Akohwarien, A et al., Design, synthesis and kinetic evaluation of conduritol aziridine derivatives as inhibitors of beta-glucocerebrosidase; a potential biomarker for Parkinson's disease. Sixth Western Canadian Medicinal Chemistry Workshop (WCMCW), Saskatoon, Saskatchewan, Sep. 21-23, 2018 (Abstract of oral presentation is provided).

(Continued)

*Primary Examiner* — Michael G. Hartley
*Assistant Examiner* — Sean R Donohue
(74) *Attorney, Agent, or Firm* — Bereskin & Parr LLP/S.E.N.C.R.L., s.r.l.; Sandra Marone

(57) ABSTRACT

The present application relates to conduritol aziridines of Formula (I), and uses thereof, for example, of $^{18}$F-labelled derivatives thereof in positron-emission tomography (PET) imaging of β-glucocerebrosidase activity.

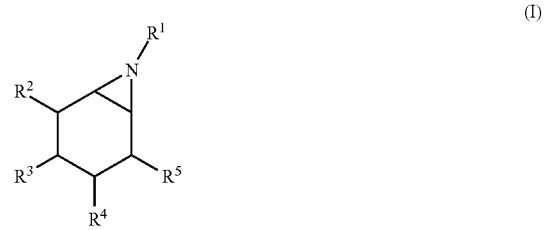

16 Claims, 8 Drawing Sheets

(56) References Cited

OTHER PUBLICATIONS

Phenix, C et al., Imaging of enzyme replacement therapy using PET. PNAS, Jun. 15, 2010, vol. 107. no. 24, pp. 10842-10847.

Way, J D., et al., Sonogashira cross-coupling reaction with 4-[18F]fluoroiodobenzene for rapid 18F-labelling of peptides; ChemComm, Jan. 8, 2015, 51, pp. 3838-3841.

Zhang, et al., [18F]Fluoroalkyl Agents: Synthesis, Reactivity and Application for Development of PET Ligands in Molecular Imaging; Current Topics In Medicial Chemistry, 2007, 7, pp. 1817-1828.

Glaser, et al., "Click Labelling" with 2-[18F]Fluoroethylazide for Positron Emission Tomography, Bionconjugate Chem., 2007, 18, pp. 989-993.

Kuhnast, B. et al., Design and Synthesis of a New [18F]Fluoropyridine-Based Haloacetamide Reagent for the Labeling of Oligonucleotides: 2-Bromo-N-[3-(2-[18F]fluoropyridin-3-yloxy) propyl]acetamide, Bioconjugate Chem., 2004, 15, pp. 617-627.

Aureli, Massimo et al., "Cell Surface Associated Glycohydrolases in Normal and Gaucher Disease Fibroblasts" (2012) J Inherit Metab Dis 35: p. 1081-1091.

\* cited by examiner

CONDURITOL AZIRIDINE DERIVATIVES AND USES THEREOF

CROSS-REFERENCE TO RELATED APPLICATIONS

This application is a National Stage of co-pending International Application No. PCT/CA2018/051323 filed on Oct. 19, 2018, which claims the benefit of priority from U.S. provisional application No. 62/574,575 filed on Oct. 19, 2017, the contents of both of which are incorporated herein by reference in their entirety.

FIELD

The present application relates to conduritol aziridine derivatives and uses thereof, for example, of $^{18}$F-labelled derivatives thereof in positron-emission tomography (PET) imaging of β-glucocerebrosidase activity.

BACKGROUND

Despite the prevalence of Parkinson's disease (PD), the disease is difficult to diagnose early with the vast majority of individuals already having significant neuronal death prior to therapeutic intervention. PD is characterized by the lysosome's unusual inability to dispose of α-synuclein in areas of the brain that primarily control motor function. Recently, studies have shown that in post-mortem brain samples from suspected PD patients, there is a deficiency in the activity of the lysosomal enzyme glucocerebrosidase (GCase).

Glucocerebrosidase

There are four known human β-glucosidases: lysosomal GCase (a member of the CAZy glycoside hydrolase family GH30), non-lysosomal glucosylceramidase (GBA2, family GH116), broad-specificity β-glucosidase (GBA3, family GH1), and intestinal lactase/phlorizin hydrolase (family GH1).

GCase is a lysosomal enzyme that catalyzes the hydrolysis of the β-glucosyl linkage in the natural substrate glucosylceramide. GCase is classified as a retaining β-glucosidase meaning it has specificity for cleaving β-glucosyl linkages and the β configuration of the resulting glucose is retained after cleavage.[1]

GCase is expressed from the GBA1 gene and is translated in the cytosol of the cell.[2] After translation, the protein is recognized by trafficking receptor LIMP2 and packaged in a vesicle.[3] This is all facilitated in the endoplasmic reticulum. GCase is trafficked from the endoplasmic reticulum to the Golgi for further processing and will finally reach the lysosome where the vesicle empties its cargo.[4] Once GCase reaches the lysosome it forms a complex with co-activator Saposin C and hydrolyzes its substrate glucosylceramide on the surface of the lysosomal membrane. The exact mechanism by which this complex forms is still not clear but it is known Saposin C is required for GCase enzymatic function.[5]

Glucosylceramide hydrolysis is important in the production of ceramide for cells. Ceramide is a required precursor for many lipid metabolic pathways and its production has a large impact on cellular membrane structure as well as many signalling pathways.[6] Ceramide can alternatively be generated through de novo synthesis and through the breakdown of sphingomyelin but in some cells[7], like neurons, glucosylceramide hydrolysis accounts for 50-90% of sphingolipid production. Deficiencies in GCase can therefore have a large impact in cellular ceramide levels. Deficiencies in GCase can also result in harmful accumulation of glucosylceramide in the lysosome. Severe enzyme deficiency, which results from inheritance of two mutation GBA1 genes, can result in a lysosomal storage disorder known as Gaucher disease. Mutation of the GBA1 gene and Gaucher disease have recently been implicated as strong risk factors for developing Parkinson's disease.[9]

Gaucher Disease: a Lysosomal Storage Disorder

The most common lysosomal storage disease is Gaucher disease where 1 in 40,000-50,000 live births are born with the disease.[10] The disease is a recessive genetic disorder where a number of mutations in the GBA1 gene can cause a dysfunctional GCase enzyme to be expressed.[11] In these cases, the mutant enzyme does not fold properly preventing trafficking across the endoplasmic reticulum or the mutation disrupts its ability to interact with Saposin C.[12] Lysosomal GCase deficiency will result in lysosome dysfunction after accumulation of glucosylceramide begins. Significant reduction in ceramide production results and, in turn, reduction in sphingolipid synthesis will occur which may, for example, have severe pathological implications.[13]

In Type I Gaucher disease, the main symptoms are chronic pain resulting from inflammation and enlargement of the spleen and liver (splenomegaly and hepatomegaly, respectively), blood related problems (e.g. anaemia, thrombocytopenia) and chronic bone pain (e.g. osteopenia, osteonecrosis and skeletal deformities)[14] resulting from deficient GCase activity primarily in macrophages.[13] These symptoms, with the addition of severe neurological symptoms affect patients with Type II (acute neurological) and Type III (chronic neurological) Gaucher disease, both of which are deadly forms.[15]

Currently, the most effective form of therapy for Gaucher disease is through Enzyme Replacement Therapy. This involves injections of exogenously produced enzyme to increase otherwise deficient levels of GCase activity in a patient.[16] This recombinant form of GCase is marketed as Cerezyme®. However, Enzyme Replacement Therapy with Cerezyme can be costly so research has also focused on the discovery of small molecular chaperones that can help traffic mutated GCase to the lysosome through binding to the active site stabilizing the folded tertiary structure and thus escaping ubiquination and degradation in the ER.[17] Discovery of such molecular chaperones for GCase has gained increased importance due to new evidence suggesting the heavy involvement of GCase in the progression of Parkinson's disease as described herein below.

GCase as a Potential Biomarker of Parkinson's Disease

Although the most common form of Gaucher disease is a mild and non-neuronopathic variant, it is well established that Gaucher disease patients and their relatives have an increased risk in developing PD.[18] PD is one of the most common neurodegenerative diseases.[19] For example, it is estimated that 55,000 Canadians aged 18 or older have been diagnosed with PD. Its symptoms are clinically characterised by bradykinesia (slowness of movement), resting tremor, postural instability and eventually, cognitive impairment such as dementia.[20] The underlying pathology in PD involves the abnormal accumulation of α-synuclein protein fibrils. Studies in cells and animals revealed that α-synuclein, a protein with the potential to mis-fold and alter basic cellular function, readily accumulates if GCase activity is lost, thus indicating the importance of GCase activity for proper α-synuclein degradation.[21]

Normally α-synuclein is highly soluble in the cell but in PD this protein forms highly ordered insoluble aggregates in the neurons of the brain.[22] Large aggregates, otherwise known as Lewy Bodies, form in the lysosomes of dopaminergic neurons.[20] The eventual result of Lewy Body growth is the death of dopaminergic neurons in the brain.[23] The most effective treatment for PD, to date, is treatment through dopamine replacement therapy. This therapy includes the replacement of dopamine, for example, by the administration of levodopa, dopamine agonists or by using monoamine oxidase B inhibitors.[24] However, sometimes patients feel the side effects from these therapies can be worse than the disease itself.[25] Accordingly, since it may be worse to receive dopamine replacement therapy than to begin therapy early, clinical diagnosis of PD typically takes around two years before treatment will begin.[26]

Clinical diagnosis of PD relies on the presence of the motor impairment symptoms described above and the absence of other features indicative of similar neurodegenerative disorders.[20] When clear signs of these symptoms are present it is estimated that the accuracy of a clinical diagnosis is 76 to 92%.[27] However, as stated in most reviews, motor symptoms only present themselves after 50% of dopaminergic neurons in the substantia nigra are already dead.[28] In younger patients, it typically takes about 7 years after the presentation of initial clinical symptoms to make a diagnosis. Early diagnosis may, for example, be difficult because early clinical symptoms overlap with other diseases like multiple system atrophy, corticobasal degeneration and progressive supranuclear palsy.[20] These diseases all share common physical symptoms but differ in their pathophysiology. Since Lewy Body pathophysiology is a very early indicator of PD, detection of α-synuclein levels in the brain could potentially accurately diagnose early PD compared to clinical diagnosis through expert symptom assessment. Currently, however, no blood test or imaging agent exists for the biochemical diagnosis of PD or the detection of Lewy Bodies in vivo.[20] Indeed, the presence of neuronal Lewy Bodies and diagnosis of PD can only be confirmed at autopsy during post-mortem brain tissue examination.[29] Accordingly, techniques that can aid in early and specific detection of PD are desirable to begin interventions, for example in younger patients, while symptoms are relatively mild and any intervention may still provide benefit and/or stop neuronal death. For example, a non-invasive test that can monitor changes in brain biochemistry during the onset of PD may be used to help screen for new biomarkers and therapeutic targets, tailor therapy to an individual by monitoring disease progression, evaluate response to targeted therapies, and/or distinguish PD from related illnesses.

Efforts have been made to image α-synuclein using Positron Emission Tomography (PET) but the inability to develop imaging probes that specifically bind to α-synuclein over other neuronal fibrils has been a major set-back in probe development.[20] Imaging dopamine uptake is the only current method used to gather biochemical information about PD. Through the use of DaTscan®, clinicians are able to visualize uptake of a radioactively labelled dopamine to gather molecular information about the disease characterized by the loss of dopaminergic neurons.[30] A problem with this technique is the loss of dopaminergic neurons is not specific to PD so DaTscans can only help confirm a diagnosis not make one by itself. Accordingly, neurologists currently use a "wait and watch" philosophy when it comes to accurately diagnosing and treating PD.[24] Waiting for a disease to progress until severe symptoms appear is not an ideal strategy for disease management. While not wishing to be limited by theory, the early stages of PD may provide the most opportune time for intervention although it remains the most difficult time to diagnosis. By having a tool to detect early Lewy Body formation, through either direct or indirect detection, neurologists may, for example, be able to extend the quality of life of their patients by influencing what therapies a patient receives and when they receive them while researchers may be equipped with a better tool for developing a cure.

GCase may be a useful target for developing such a tool. Recently, studies have shown that patients with Gaucher disease are at a higher risk of developing PD compared to a healthy control. One study of nearly 6000 patients showed that Type I Gaucher disease patients are 6 to 17 fold more likely to develop PD compared to a healthy group of patients.[31] Although Gaucher disease patients have homozygous mutations of the GBA1 gene, other studies have shown that that even heterozygous carriers of GBA1 mutations are at higher risk than the general population. A study of large cohorts of PD patients showed 4-7% were found to carry heterozygous GBA1 mutations.[32] A different study looking at 57 post-mortem brain samples from PD patients demonstrated 12% carried at least one mutation in the GBA1 gene.[33] Additionally, it has been reported that in a group of 5000 patients, there was a greater than 1 in 5 chance for a PD patient to carry a GBA1 mutation.[34]

It is clear that there is a strong correlation between GBA1 mutations and the occurrence of PD but further investigation in cells, animals and humans were undertaken to understand the role that GCase has in the progression of the disease, for example, the correlation between GCase and Lewy Body formation. For example, a dementia study has shown that of 95 patients with pathological Lewy Body findings, 28% of them had GBA1 mutations.[35] When another group examined post-mortem brain samples from PD patients, they found that from the patients that were homozygous and heterozygous for GBA1 mutations, 80% and 75% respectively showed that the GCase protein was co-localized within the Lewy Bodies.[34] The link between GCase and PD was further confirmed when PD patients who had heterozygous mutations in GBA1 were shown to have significant levels of the enzyme co-precipitated in their Lewy bodies.[34] Further, it was demonstrated that in cell lines with a GBA1 deficiency, global lysosomal dysfunction was correlated with α-synuclein aggregation.[36] Taken together, while not wishing to be limited by theory, these studies strongly suggest that GCase, both mutant and wild type, are involved in Lewy body formation.

Subsequent studies using post-mortem brain samples from PD patients carrying a heterozygous mutation in the GBA1 gene confirmed that a significant deficiency in GCase activity was found in cells sampled from the SN (58% lower) and putamen (47% lower) compared to healthy controls.[37] Such low levels indicated that other biological processes, e.g. changes in GCase trafficking to the lysosome, were affecting levels of enzyme activity in the brain samples.

Increased α-synuclein levels were not only shown to occur in cell lines with GBA1 knockouts but also in vivo with GBA1 mutant mouse models of Gaucher disease. It has been shown over the course of the mouse's life, increases in α-synuclein levels were directly correlated to decreases in GCase enzymatic activity.[38] Mice receiving injections of exogenous recombinant GCase enzyme were found to have reduced levels of α-synuclein, fewer pathological Lewy Bodies and some cognitive symptoms associated with PD were ameliorated.[13] This data is consistent with results obtained from experiments using cell lines having GBA1 deficiency and lysosomal dysfunction that promoted α-synuclein aggregation but recovered normal lysosomal function with the addition of exogenous GCase.[36] While not wishing to be limited by theory, this suggests that GCase activity alone is able to mitigate the aggregation of α-synuclein in the formation of Lewy Bodies presumably due to normal lysosomal function.

Observable decreases in GCase activity in PD patients have also been reported without any GBA1 mutations. This was surprising because it was initially thought that decrease in GCase activity was directly a consequence of the expression of mutant enzyme that was catalytically incompetent. One thorough investigation evaluated 19 post-mortem brain samples from patients confirmed of having PD but no GBA1 mutations.[39] The patients varied from being afflicted by early to late stages of progression of PD. Neuronal death was only present in the late stage samples, although, sodium dodecyl sulphate (SDS) soluble α-synuclein levels were elevated in all samples. SDS-soluble refers to proteins that are largely insoluble in water but will only dissolve in the presence of strong detergents like SDS. This includes samples containing insoluble α-synuclein aggregates (Lewy Body) or GCase. There was a strong negative correlation shown between the levels of SDS-soluble α-synuclein increasing and the SDS-soluble GCase levels decreasing. Lysosomal GCase enzyme activity was also shown to decrease. This observation was seen in both early and late stages of the disease. This is interesting because GCase activity is shown to decrease even in early stages of the disease before neuronal death has occurred. Furthermore, these results were taken from patients without GBA1 mutations who expressed the healthy enzyme suggesting that GCase activity may decrease in all patients with PD. These two facts together highlight the significant impact GCase may have as a biomarker for the progression of PD or a therapeutic target.

A more comprehensive biochemical analysis that measured GCase activity, α-synuclein levels and lysosomal function, was performed on patients who carry wild type GBA1 and who were diagnosed with the non-genetic (sporadic) form of PD. A deficiency in GCase activity was associated with early accumulation of α-synuclein leading to chaperone-mediated autophagy dysfunction believed to exacerbate the age-related effects observed in lysosomal activity.[40] Deficiency in GCase enzyme activity also occurred in early PD suggesting that reduction in GCase activity arose prior to significant neuronal loss.[40] Taken together, these studies provide strong preclinical and clinical evidence that a deficiency in GCase activity may reveal early PD prior to significant neuronal death. Additionally, lysosomal activity and cellular levels of GCase have been shown to be decreased early on in the disease, before neuronal death has occurred and in patients without any GBA1 mutations suggesting, while not wishing to be limited by theory, that GCase activity may, for example, be a universal biomarker for PD patients.

There were reductions in GCase concentration, both in the cytoplasm and lysosome, in the early stages of the disease. Despite this early reduction, GCase concentration in the cytoplasm seemed to remain at this level, even in the late stage PD samples.[39] GCase mRNA levels also appeared to remain constant throughout the progression of the disease. Lysosomal GCase enzymatic activity, however, seemed to drop continuously as the disease progressed from early to late.[39] While not wishing to be limited by theory, this suggests in PD there is not a reduction in the GCase being produced but rather the amount that is reaching the lysosome. A separate study has demonstrated that there is a bidirectional pathogenic loop in PD where α-synuclein accumulation reduces GCase trafficking to the lysosome while trafficking of GCase to lysosome reduces α-synuclein levels.[41] While not wishing to be limited by theory, this suggests GCase also may present a therapeutic target because promotion of its trafficking to the lysosome can reduce α-synuclein aggregation.

In sum, GCase activity levels are directly correlated with the accumulation of α-synuclein, the formation of Lewy Bodies and thus the pathogenicity of PD. The disease is promoted by the inheritance of mutant forms of GCase but can still progress regardless of if GBA1 mutations exist or not. The exact reason GCase activity levels drop in PD patients is still unknown and, while not wishing to be limited by theory, may be part of some negative feedback loop between α-synuclein aggregation and GCase trafficking to the lysosome. It has also been shown that lysosomal GCase activity decreases occur early on in the progression of PD and can be detected before neuronal death occurs. These data suggest, for example, that GCase is an attractive biomarker for detecting the early and accurate onset of PD and as a potential therapeutic target for drug development in patients with or without GBA1 mutations.

GCase Molecular Probe Design

Since activity of GCase is shown to be decreased in patients with PD it is desirable to develop activity-based probes in order to detect activity and track GCase biodistribution within a biological system.

Activity-based protein profiling enlists the help of a molecular probe that is designed to interact with the active site of a particular enzyme. These activity-based probes take advantage of an enzyme's catalytic mechanism in order to irreversibly bind within the active site.[42] Probes can be developed by taking a compound that binds well to the active site of an enzyme and coupling to this compound a detectable tag such as a fluorescent molecule or a radioactive isotope. Typically, these probes optimally have 3 characteristics in order for them to be useful activity based probes: 1) high affinity for the active site so they can bind to the enzyme at biologically significant concentrations, 2) high selectivity to the target enzyme so they produce a signal for only one target, 3) a "warhead" that does not reduce active site binding and forms an irreversible covalent bond at some point during the enzyme's catalytic mechanism.[43]

Two off-site targets to be concerned with for the production of GCase activity based probes are GBA2 and GBA3 which are β-glucosidases from the same family as GCase. These glucosidases are found in the cytosol rather than the lysosome.[44] Often compounds that are potent binders of GCase also bind well with GBA2 or GBA3.

One of the structures to mimic for an activity based probe is GCase's natural substrate glucosylceramide. However, while the structure of the natural substrate of an enzyme is often used as a starting point in the design of inhibitors glucosylceramide is not simple to synthesize in large amounts or easily modified. One way of circumventing this issue is by replacing the ceramide moiety with a different leaving group while keeping the glucose moiety intact since GCase recognizes glucose in the natural substrate.

For example, Withers et al. have shown that if you replace one of the hydroxyls on glucose with an electronegative fluorine and install a good leaving group at the anomeric carbon, this generates a mechanism-based inhibitor where the glucosyl-enzyme intermediate is rapidly formed but only slowly hydrolyzed, especially when the fluorine is in the 2 position.[45] Several examples of this type of activity-based probe with fluorine in the 2 position and a good leaving group on the anomeric oxygen of glucose have been reported.[42] For example, Phenix et al. synthesized a β-2,4-dinitrophenyl-fluorodeoxyglucose (Scheme 1, compound 1.1) for the purpose of labelling Cerezyme®, a recombinant form of GCase used for treating Gaucher disease.[46] The authors also synthesized this compound with radioactive fluorine-18 ($^{18}$F) showing the glucosyl-enzyme is extremely stable (t½>1300 min). However, despite a very stable glucosyl-enzyme intermediate, these 2-fluoroglucose probes had lower binding affinities.

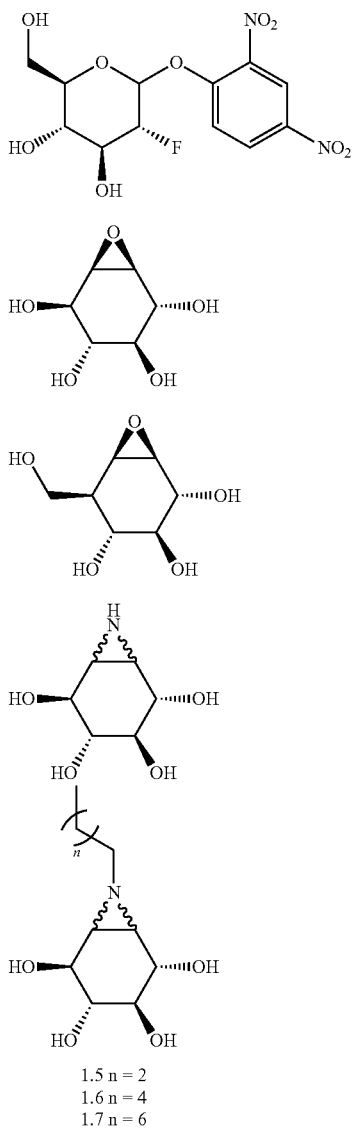

Scheme 1

1.1

1.2

1.3

1.4

1.5 n = 2
1.6 n = 4
1.7 n = 6

One of the first and most widely available irreversible inhibitors of GCase was conduritol-B-epoxide (CBE) (Scheme 1; compound 1.2) having a $K_i$ value of about 140 μM.[47] Unlike the fluorosugar inhibitors that are pyranohexoses, CBE is an inositol-based compound whose polyhydroxyl cyclohexane conformation demonstrates excellent GCase active site recognition. Unlike glucose of the natural substrate, CBE is not a pyranose and as a result cannot be efficiently hydrolyzed from the active site of the covalent inhibitor-enzyme complex. The covalent complex has been shown to form through nucleophilic attack from glutamic acid residue 340 on the epoxide of CBE. In 2005, Premkumar et al. published a crystal structure of CBE covalently bound to GCase showing that the hydroxyl groups of the conduritol backbone formed hydrogen bonds within the active site and that the epoxide opened to form a covalent bond with the nucleophilic glutamic acid 340.[48] While CBE is a reasonably potent inhibitor of GCase it also inhibits the cytosolic beta-glucosidase GBA2.[48]

Aerts and Overkleeft have developed several cyclophellitol and aziridine-type cyclophellitol based probes with fluorescent and biotin tags.[49] The cyclophellitol based inhibitors contain the electrophilic epoxide warhead and, like CBE, form non-hydrolysable inhibitor-enzyme complexes. The structure of cyclophellitol (Scheme 1, compound 1.3) is a compromise between that of glucose and CBE but unlike the Withers fluoro-glucose based inhibitors, in which carbon 2 was modified, a modification was made in compound 1.3 to mimic a carbon 6 modification on glucose.[50] This was done because, from structural biology studies, it is known modifications at carbon 2 prevent useful enzyme-substrate interactions while bulky hydrophobic modifications at carbon 6 are tolerated, and in fact, may enhance active site binding.[42] Withers' reported a conduritol aziridine glucosidase inhibitor (Scheme 1, compound 1.4) published in 1989[51]. Other inhibitors that were synthesized and characterized are compounds 1.5, 1.6 and 1.7 (Scheme 1).[44] Compounds 1.5 to 1.7 were synthesized and characterized as racemic mixtures of the two enantiomers. These activity-based irreversible inhibitors were prepared in 8 steps from commercially available myo-inositol. Adams et al. also reported that by lengthening the alkyl chain on the aziridine, the potency of the inhibitor increased.[44] Furthermore, 1.7 has excellent in vitro characteristics in terms of its cell permeability and selective inhibition of GCase over GBA2 and GBA3. Additionally, while not wishing to be limited by theory, its inositol backbone may potentially allow it to be a substrate for inositol transporters promoting its passage across the Blood Brain Barrier (BBB). The BBB is a selective membrane, made up of tightly joined endothelial cells, that selectively allow certain small lipophilic molecules to passively enter the brain and express proteins that actively transport hydrophilic substances.[52] Considering the structure of compound 1.7, it is not a highly lipophilic compound. However, aziridine 1.7 has been shown to be cell permeable by Adams et al.[42] BBB permeability in vitro can be studied, for example, using a trans-well assay that employs canine kidney cell lines that overexpress important protein pumps while also forming a tight monolayer of cells that mimics the BBB.[53]

Table 1 includes an overview of the reported kinetic data on the compounds shown in Scheme 1 for inhibition of GCase.

Recent results have shown that the N-octyl conduritol aziridine 1.7 inactivation rates are enhanced towards GCase in the presence of Saposin C, an allosteric activator protein that helps GCase gain access to glucosyl ceramide within the cell membrane. Aberrant expression of Saposin C is known to be involved in juvenile Gaucher disease and lipid antigen presentation in T cells,[54] meaning a GCase radiotracer may also be useful in the context of Saposin C variants of Gaucher disease and immune function.

Radiopharmaceuticals for PET Imaging

Positron Emission Tomography (PET) is a sensitive and clinically established nuclear-based molecular imaging modality that produces 3-D images of biological and pharmacological processes in the body.

There are several positron emitting isotopes available for the production of radiopharmaceuticals. The most commonly used positron emitting isotopes are $^{11}$C, $^{131}$I and $^{18}$F. To choose a radionuclide for a GCase radiotracer two main things may be considered: 1) half-life of the nuclide and 2) the effects the radioactive atom will have on the probe's biological activity. Generally, $^{18}$F is the isotope of choice for PET due to its low positron kinetic energy permitting high-resolution imaging, relatively low costs, and relatively long half-life (about 110 minutes), longer than the short half-life of $^{11}$C (20 minutes) but not as long as the half-life of $^{131}$I (8 days). Having a longer half-life may help enable radiochemical synthesis, for example, as reaction times can be increased as well as allowing time for purification, quality control and/or shipping to a small animal imaging facility or ultimately a patient. If the half-life is too long, however, radioactive safety risks may be higher because the injected animal or human remains radioactive for longer periods of time. $^{18}$F may also be used to label a drug or probe without significantly affecting its biological activity. This is because $^{18}$F is an isostere of both hydrogen and hydroxyl groups.[55] $_{18}$F is available at virtually all cyclotron sites.

Due to the power of PET to image protein activity and/or expression non-invasively, a significant number of radiotracers have been developed to assess neurophysiological markers of disease in humans. Although new radiotracers to assist in CNS-disease diagnosis are desirable, the full power of PET is often more suited to study the biology of novel drug targets, validate neurobiology in disease states, and/or as a companion for drug development. PET is becoming an increasingly important research tool in the pharmaceutical industry for example, for determining brain and organ uptake of radioactive versions of experimental CNS drugs, establishing proof of drug mechanism, measuring receptor occupancy of a drug at specific doses, and guiding dosing regimens to optimize therapeutic response and minimizing side effects; all intended to accelerate decision making for clinical trials. In addition, PET is being used to quantify the pharmacodynamic effects, understanding pathophysiology of CNS disease and revealing how genetic variation can affect therapeutic response.[56] Significant efforts have been made to develop PET tracers that are irreversible inhibitors of enzyme activity in the brain including monoamine oxidase,[57] acetylcholine esterase,[58] fatty acid amide hydrolase,[59] and monoacyl glycerol lipase.[60] Quantitative imaging of enzyme activity using irreversible PET tracers is more technically challenging than reversible inhibitors, kinetic modeling techniques are used as well as careful optimization of inhibitor efficiency.[59(e),61]

SUMMARY

New conduritol aziridine derivatives have been prepared which are inhibitors of the lysosomal enzyme glucocerebrosidase (GCase). Radioactive derivatives may be useful for detection of GCase in animal-based models and humans using PET imaging. Such activity-based probes may, for example, be useful molecular tools for elucidating GCase's involvement in the progression of PD, for evaluating therapeutic potential of new drugs and/or for the accurate and early diagnosis of PD. Non-fluorinated derivatives may be useful, for example, in creating models of diseases associated with decreased β-glucocerebrosidase activity.

Accordingly, the present application includes a compound of Formula I:

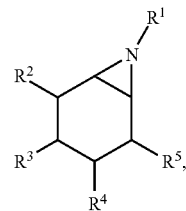

I wherein
R$^1$ is a group selected from:
—(CH$_2$)$_x$CH$_2$X,

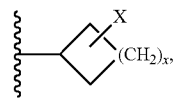

—(CH$_2$)$_y$CHX(CH$_2$)$_z$CH$_3$,
—(CH$_2$)$_y$NH(CH$_2$)$_z$CH$_2$X,

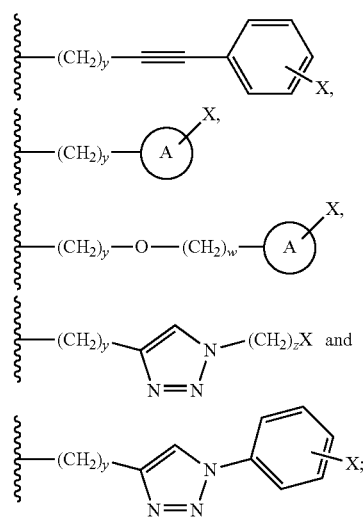

x is an integer between 1 and 20;
y is an integer between 1 and 10;
z is an integer between 1 and 10;
w is an integer between 0 and 10;

is aryl or heteroaryl;
(i) one or two of R$^2$, R$^3$, R$^4$ and R$^5$ is —OC$_{1-20}$alkyl or —OC$_{4-20}$cycloalkyl, the others are —OH, and X is H or F;
(ii) one of R$^2$, R$^3$, R$^4$ and R$^5$ is F-substituted —OC$_{1-20}$ alkyl or F-substituted —OC$_{4-20}$cycloalkyl, two or three of the others are —OH, optionally one of the others is —OC$_{1-20}$alkyl or —OC$_{4-20}$cycloalkyl, and X is H;
(iii) one of R$^2$, R$^3$, R$^4$ and R$^5$ is F, the others are —OH, and X is H; or (iv) all of $R^2$, $R^3$, $R^4$ and $R^5$ are —OH, and X is H or F; and F is $^{19}F$ or $^{18}F$;

provided that when all of $R^2$, $R^3$, $R^4$ and $R^5$ are —OH, $R^1$ is not $(CH_2)_xCH_2X$, wherein X is H or F; or —$(CH_2)_y$CHX$(CH_2)_z$CH$_3$, wherein X is H.

The present application also includes a compound of Formula I:

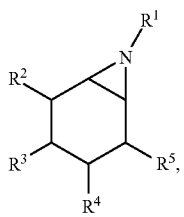

I wherein
$R^1$ is a group selected from:
—$(CH_2)_xCH_2X$,

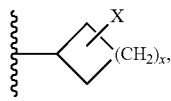

—$(CH_2)_y$CHX$(CH_2)_z$CH$_3$,
—$(CH_2)_y$NH$(CH_2)_z$CH$_2$X,

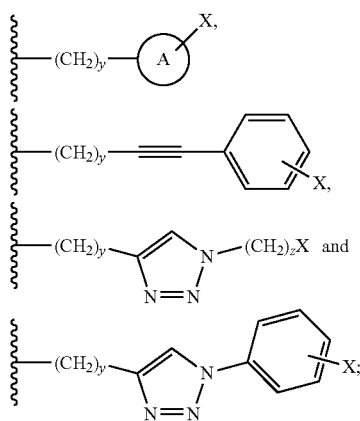

x is an integer between 1 and 20;
y is an integer between 1 and 10;
z is an integer between 1 and 10;

is aryl or heteroaryl;
(i) one or two of $R^2$, $R^3$, $R^4$ and $R^5$ is —OC$_{1-20}$alkyl or —OC$_{4-20}$cycloalkyl, the others are —OH, and X is H or F;
(ii) one of $R^2$, $R^3$, $R^4$ and $R^5$ is F-substituted —OC$_{1-20}$alkyl or F-substituted —OC$_{4-20}$cycloalkyl, two or three of the others are —OH, optionally one of the others is —OC$_{1-20}$alkyl or —OC$_{4-20}$cycloalkyl, and X is H;
(iii) one of $R^2$, $R^3$, $R^4$ and $R^5$ is F, the others are —OH, and X is H; or
(iv) all of $R^2$, $R^3$, $R^4$ and $R^5$ are —OH, and X is H or F; and
F is $^{19}F$ or $^{18}F$;

provided that when all of $R^2$, $R^3$, $R^4$ and $R^5$ are —OH, $R^1$ is not $(CH_2)_xCH_2X$, wherein X is H or F; or —$(CH_2)_y$CHX$(CH_2)_z$CH$_3$, wherein X is H.

The present application also includes a use of an $^{18}F$-labelled compound of the application for positron-emission tomography (PET) imaging of β-glucocerebrosidase activity in a subject.

The present application also includes a method for imaging β-glucocerebrosidase activity in a subject, the method comprising:
administering an $^{18}F$-labelled compound of the application to the subject; and
detecting the presence of retained radioactivity in the subject using positron-emission tomography (PET).

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which.

DETAILED DESCRIPTION

I. Definitions

Figure 1:
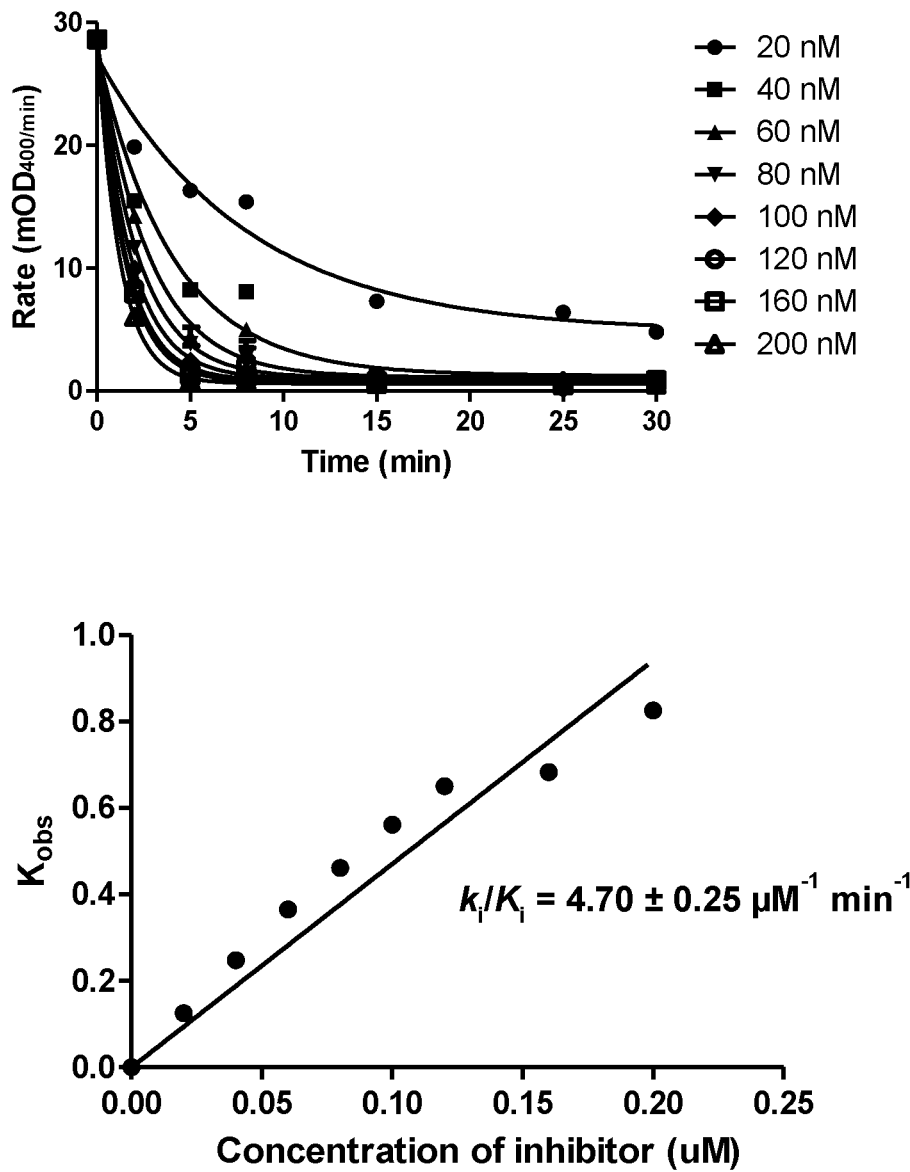
FIG. 1 shows a plot of remaining enzyme activity over time at the indicated inhibitor concentrations fitted to a one phase decay equation for N-octyl conduritol aziridine (top) and a plot of the observed rate constants of inactivation versus the concentration of inhibitor for that compound (bottom).

Unless otherwise indicated, the definitions and embodiments described in this and other sections are intended to be applicable to all embodiments and aspects of the present application herein described for which they are suitable as would be understood by a person skilled in the art.

The present application refers to a number of chemical terms and abbreviations used by those skilled in the art. Nevertheless, definitions of selected terms are provided for clarity and consistency.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process/method steps. As used herein, the word "consisting" and its derivatives, are intended to be close ended terms that specify the presence of stated features, elements, components, groups, integers, and/or steps, and also exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a compound" should be understood to present certain aspects with one compound or two or more additional compounds. In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions for the reaction to proceed to a sufficient extent to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression "proceed to a sufficient extent" as used herein with reference to the reactions or process/method steps disclosed herein means that the reactions or steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 100% of the starting material or substrate is converted to product.

The term "protecting" as used herein refers to using a chemical moiety, i.e. a "protecting group" of "PG" which protects or masks a reactive portion of a molecule to prevent side reactions in that reactive portion of the molecule, while manipulating or reacting a different portion of the molecule. After the manipulation or reaction is complete, the protecting group is removed under conditions that do not degrade or decompose the remaining portions of the molecule, i.e. the protected reactive portion of the molecule is "deprotected". The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas).

The term "leaving group" as used herein refers to a group that is readily displaceable by a nucleophile, for example, under $S_N^2$ nucleophilic substitution reaction conditions. Examples of suitable leaving groups include OMs. The abbreviation "Ms" as used herein refers to the group methanesulfonyl.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1-n2}$". For example, the term $C_{1-20}$alkyl means an alkyl group having 1, 2, 3, 4, 5, 6, 7, 8, 9, 10, 11, 12, 13, 14, 15, 16, 17, 18, 19 or 20 carbon atoms.

The term "aryl" as used herein, whether it is used alone or as part of another group, refers to cyclic groups that contain at least one aromatic ring. In an embodiment of the present application, the aryl group contains from 6, 9, 10 or 14 atoms, such as phenyl, naphthyl, indanyl or anthracenyl.

The term "heteroaryl" as used herein refers to cyclic groups that contain at least one aromatic ring and at least one heteroatom, such as N, O and/or S. The number of atoms that are possible in the referenced heteroaryl group are indicated by the numerical prefix $C_{n1-n2}$. For example, the term $C_{5-10}$heteroaryl means an aryl group having 5, 6, 7, 8, 9 or 10 atoms, in which at least one atom is a heteroatom, such as N, O and/or S.

The term "cycloalkyl" as used herein, whether it is used alone or as part of another group, means a mono- or bicyclic, saturated cycloalkyl group. The number of carbon atoms that are possible in the referenced cycloalkyl group are indicated by the numerical prefix "$C_{n1-n2}$". For example, the term $C_{4-20}$cycloalkyl means a cycloalkyl group having 4, 5, 6, 7, 8, 9, 10, 11, 12, 13, 14, 15, 16, 17, 18, 19 or 20 carbon atoms. When a cycloalkyl group contains more than one cyclic structure or rings, the cyclic structures are fused, bridged, spiro connected or linked by a single bond. A first cyclic structure being "fused" with a second cyclic structure means the first cyclic structure and the second cyclic structure share at least two adjacent atoms therebetween. A first cyclic structure being "bridged" with a second cyclic structure means the first cyclic structure and the second cyclic structure share at least two non-adjacent atoms therebetween. A first cyclic structure being "spiro connected" with a second cyclic structure means the first cyclic structure and the second cyclic structure share one atom therebetween.

The structures,

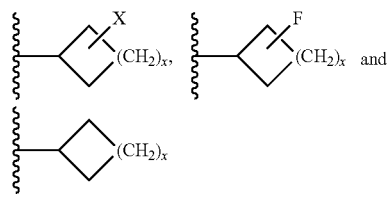

as used herein include both mono- and bicyclic saturated cycloalkyl groups.

The term "F-substituted" as used herein in reference to a group which contains an alkyl means that one of the H atoms in the alkyl group is replaced with F. For example, the term F-substituted —O$C_{1-20}$alkyl refers to a group in which one of the H atoms in the $C_{1-20}$alkyl is replaced with F.

The term "F-substituted" as used herein in reference to a group which contains a cycloalkyl means that one of the H atoms in the cycloalkyl group is replaced with F. For example, the term F-substituted —O$C_{4-20}$cycloalkyl refers to a group in which one of the H atoms in the $C_{4-20}$cycloalkyl is replaced with F.

The term "compound of the application" and the like as used herein refers to compounds of Formula I, including compounds of Formulae I(a), I(a)(i), (a)(ii), I(b), I(b)(i), I(b)(ii), I(c) and I(d).

The term "$^{18}$F labelled compound of the application" and the like as used herein refers to compounds of Formulae I (wherein X is F), I(a) (wherein X is F), I(a)(i), I(b) (wherein X is F), I(b)(i), I(c) and I(d), wherein X is $^{18}$F.

The term "non-fluorinated compound of the application" and the like as used herein refers to compounds of Formulae I (wherein X is H), I(a) (wherein X is H), I(a)(ii), I(b) (wherein X is H) and I(b)(ii).

The term "subject" as used herein includes all members of the animal kingdom including mammals. In an embodiment, the subject is a human.

The term "radiopharmaceutically acceptable" means compatible with the administration to or use in subjects such as humans for imaging β-glucocerebrosidase activity by positron-emission-tomography (PET).

The term "pharmaceutically acceptable" means compatible with the administration to or use in cells or subjects such as mammals.

In embodiments of the present application, the compounds described herein have at least one asymmetric center. Where compounds possess more than one asymmetric center, they may exist as diastereomers. It is to be further understood that while the stereochemistry of the compounds may be as shown in any given compound listed herein, such compounds may also contain certain amounts (e.g. less than 20%, optionally less than 10%, optionally less than 5%, optionally less than 1%) of compounds having alternate stereochemistry.

II. Compounds, Methods of Preparation Thereof and Compositions

New conduritol aziridine derivatives have been prepared which are inhibitors of the lysosomal enzyme glucocerebrosidase (GCase).

Accordingly, the present application includes a compound of Formula I:

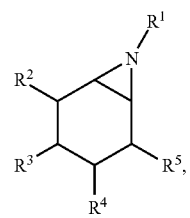

wherein $R^1$ is a group selected from:

—(CH$_2$)$_x$CH$_2$X,

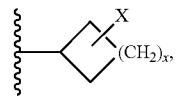

—(CH$_2$)$_y$CHX(CH$_2$)$_z$CH$_3$,
—(CH$_2$)$_y$NH(CH$_2$)$_z$CH$_2$X,

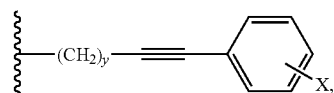

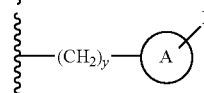

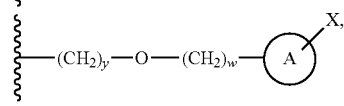

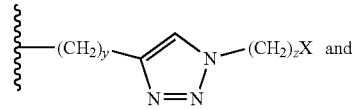

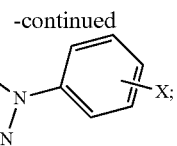

x is an integer between 1 and 20;
y is an integer between 1 and 10;
z is an integer between 1 and 10;
w is an integer between 0 and 10;

is aryl or heteroaryl;
  (i) one or two of $R^2$, $R^3$, $R^4$ and $R^5$ is —$OC_{1-20}$alkyl or —$OC_{4-20}$cycloalkyl, the others are —OH, and X is H or F;
  (ii) one of $R^2$, $R^3$, $R^4$ and $R^5$ is F-substituted —$OC_{1-20}$alkyl or F-substituted —$OC_{4-20}$cycloalkyl, two or three of the others are —OH, optionally one of the others is —$OC_{1-20}$alkyl or —$OC_{4-20}$cycloalkyl, and X is H;
  (iii) one of $R^2$, $R^3$, $R^4$ and $R^5$ is F, the others are —OH, and X is H; or
  (iv) all of $R^2$, $R^3$, $R^4$ and $R^5$ are —OH, and X is H or F; and
F is $^{19}F$ or $^{18}F$;
provided that when all of $R^2$, $R^3$, $R^4$ and $R^5$ are —OH, $R^1$ is not $(CH_2)_xCH_2X$, wherein X is H or F; or —$(CH_2)_y$CHX$(CH_2)_z$CH_3$, wherein X is H.

The present application also includes a compound of Formula I:

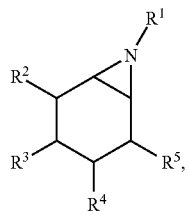

I wherein
$R^1$ is a group selected from:
—$(CH_2)_xCH_2X$,

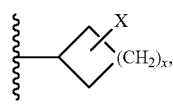

—$(CH_2)_y$CHX$(CH_2)_z$CH_3$,
—$(CH_2)_y$NH$(CH_2)_z$CH_2X$,

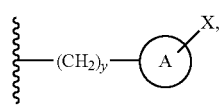

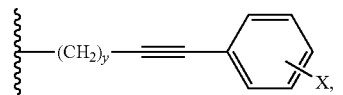

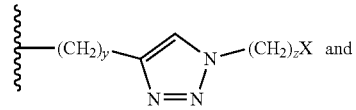

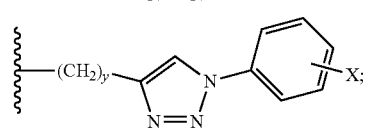

x is an integer between 1 and 20;
y is an integer between 1 and 10;
z is an integer between 1 and 10;

is aryl or heteroaryl;
  (i) one or two of $R^2$, $R^3$, $R^4$ and $R^5$ is —$OC_{1-20}$alkyl or —$OC_{4-20}$cycloalkyl, the others are —OH, and X is H or F;
  (ii) one of $R^2$, $R^3$, $R^4$ and $R^5$ is F-substituted —$OC_{1-20}$alkyl or F-substituted —$OC_{4-20}$cycloalkyl, two or three of the others are —OH, optionally one of the others is —$OC_{1-20}$alkyl or —$OC_{4-20}$cycloalkyl, and X is H;
  (iii) one of $R^2$, $R^3$, $R^4$ and $R^5$ is F, the others are —OH, and X is H; or
  (iv) all of $R^2$, $R^3$, $R^4$ and $R^5$ are —OH, and X is H or F; and
F is $^{19}F$ or $^{18}F$;
provided that when all of $R^2$, $R^3$, $R^4$ and $R^5$ are —OH, $R^1$ is not $(CH_2)_xCH_2X$, wherein X is H or F; or —$(CH_2)_y$CHX$(CH_2)_z$CH_3$, wherein X is H.

In an embodiment, the compound of Formula I has one or is a mixture of both of the following stereochemical configurations:

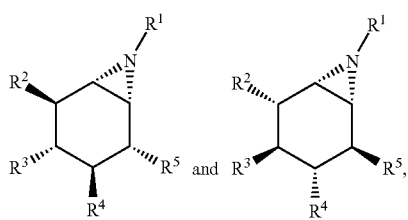

wherein $R^1$, $R^2$, $R^3$, $R^4$ and $R^5$ are as defined for the compound of Formula I.

In an embodiment, all of $R^2$, $R^3$, $R^4$ and $R^5$ are —OH.

Accordingly, in some embodiments of the present application, the compound of Formula I is a compound of Formula I(a):

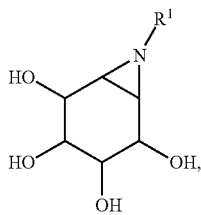

wherein

R¹ is a group selected from:

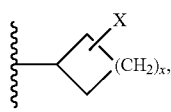

—(CH$_2$)$_y$CHX(CH$_2$)$_z$CH$_3$,
—(CH$_2$)$_y$NH(CH$_2$)$_z$CH$_2$X,

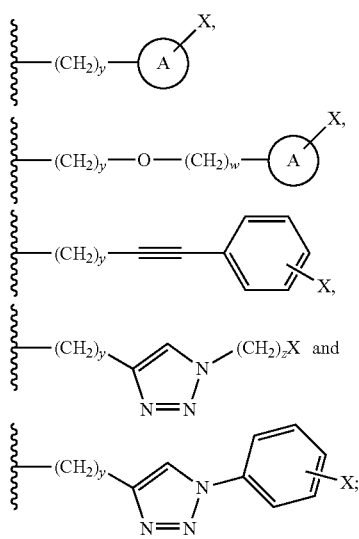

x is an integer between 1 and 20;
y is an integer between 1 and 10;
z is an integer between 1 and 10;
w is an integer between 0 and 10;

is aryl or heteroaryl;
X is H or F; and
F is $^{19}$F or $^{18}$F,
provided that when X is H, R¹ is not —(CH$_2$)$_y$CHX(CH$_2$)$_z$CH$_3$.

In some embodiments of the present application, the compound of Formula I is a compound of Formula I(a):

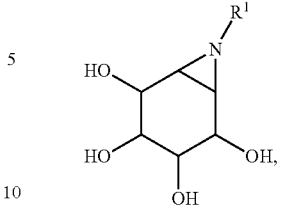

wherein

R¹ is a group selected from:

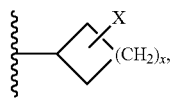

—(CH$_2$)$_y$CHX(CH$_2$)$_z$CH$_3$,
—(CH$_2$)$_y$NH(CH$_2$)$_z$CH$_2$X,

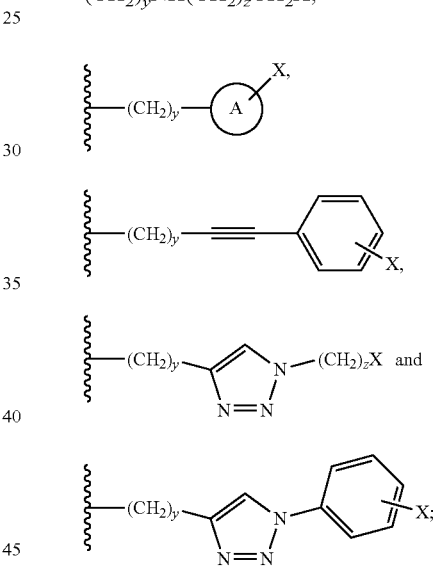

x is an integer between 1 and 20;
y is an integer between 1 and 10;
z is an integer between 1 and 10;

is aryl or heteroaryl;
X is H or F; and
F is $^{19}$F or $^{18}$F,
provided that when X is H, R¹ is not —(CH$_2$)$_y$CHX(CH$_2$)$_z$CH$_3$.

In an embodiment, the compound of Formula I(a) has one or is a mixture of both of the following stereochemical configurations:

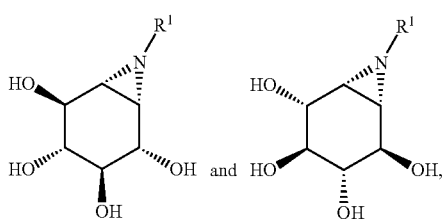

wherein R¹ is as defined for the compound of Formula I(a).

In an embodiment, X is F. Accordingly, in some embodiments of the present application, the compound of Formula I is a compound of Formula I(a)(i):

I(a)(i)

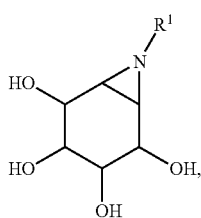

wherein
R¹ is a group selected from:

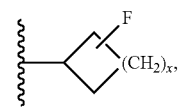

—(CH₂)$_y$CHF(CH₂)$_z$CH₃,
—(CH₂)$_y$NH(CH₂)$_z$CH₂F,

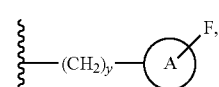

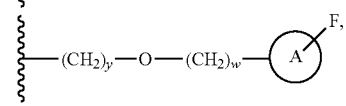

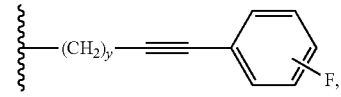

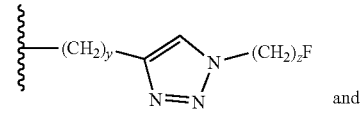

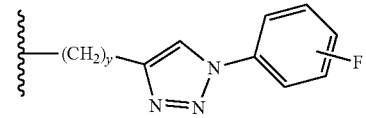

;

Ⓐ is aryl or heteroaryl;
x is an integer between 1 and 20;
y is an integer between 1 and 10;
z is an integer between 1 and 10;
w is an integer between 0 and 10; and
F is ¹⁹F or ¹⁸F.

In some embodiments of the present application, the compound of Formula I is a compound of Formula I(a)(i):

I(a)(i)

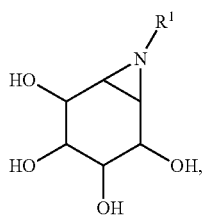

wherein
R¹ is a group selected from:

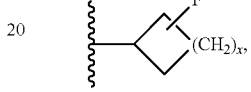

—(CH₂)$_y$CHF(CH₂)$_z$CH₃,
—(CH₂)$_y$NH(CH₂)$_z$CH₂F,

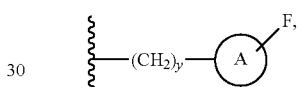

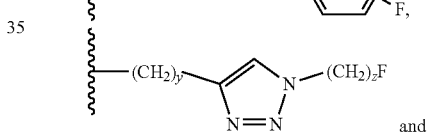

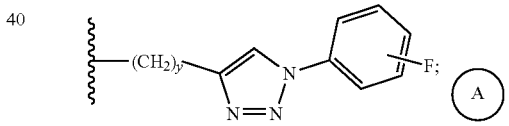

and

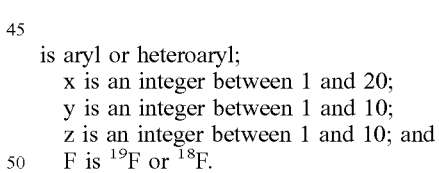

Ⓐ is aryl or heteroaryl;
x is an integer between 1 and 20;
y is an integer between 1 and 10;
z is an integer between 1 and 10; and
F is ¹⁹F or ¹⁸F.

In some embodiments of the compound of Formula I, wherein all of R², R³, R⁴ and R⁵ are —OH and X is F and the compound of Formula I(a)(i), R¹ is

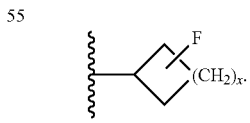

In another embodiment, x is an integer between 1 and 10. In a further embodiment, x is an integer between 2 and 7. In another embodiment of the present application, R¹ is a cyclopentyl or adamantyl group in which one of the hydrogen atoms has been replaced by a fluorine atom.

In some embodiments of the compound of Formula I, wherein all of R², R³, R⁴ and R⁵ are —OH and X is F and the compound of Formula I(a)(i), $R^1$ is —$(CH_2)_y$CHF$(CH_2)_z$-$CH_3$. In another embodiment, y+z is an integer between 2 and 10. In a further embodiment, y+z is an integer between 4 and 7. In another embodiment of the present application, y is 2 and z is 4.

In an embodiment, the compound of Formula I has the structure:

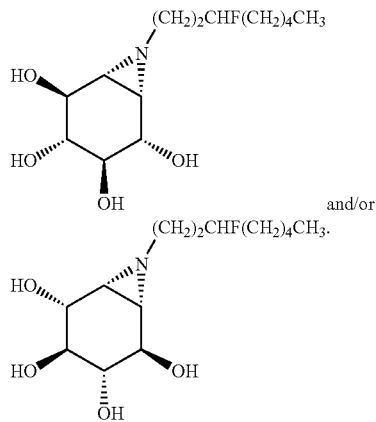

and/or

In some embodiments of the compound of Formula I, wherein all of $R^2$, $R^3$, $R^4$ and $R^5$ are —OH and X is F and the compound of Formula I(a)(i), $R^1$ is —$(CH_2)_y$NH$(CH_2)_z$-$CH_2F$. In another embodiment, y+z is an integer between 2 and 10. In a further embodiment, y+z is an integer between 4 and 7. In another embodiment, y is 2. In a further embodiment, z is 4.

In some embodiments of the compound of Formula I, wherein all of $R^2$, $R^3$, $R^4$ and $R^5$ are —OH and X is F and the compound of Formula I(a)(i), $R^1$ is

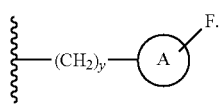

In another embodiment,

is aryl. In a further embodiment,

is phenyl. In another embodiment,

is $C_{5-10}$heteroaryl. In a further embodiment, the heteroatom in the heteroaryl group is nitrogen. In another embodiment,

is pyridyl. In a further embodiment, y is an integer between 2 and 10. In another embodiment, y is an integer between 4 and 8. In a further embodiment, y is 6.

In some embodiments of the compound of Formula I, wherein all of $R^2$, $R^3$, $R^4$ and $R^5$ are —OH and X is F and the compound of Formula I(a)(i), $R^1$ is

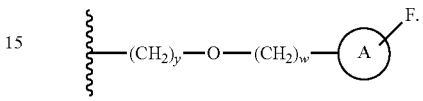

In another embodiment,

is aryl. In a further embodiment,

is phenyl. In another embodiment,

is $C_{5-10}$heteroaryl. In a further embodiment, the heteroatom in the heteroaryl group is nitrogen. In another embodiment,

is pyridyl. In another embodiment, $R^1$ is

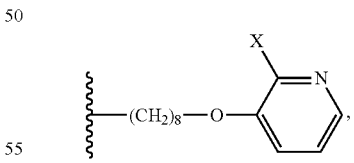

wherein X is F. In a further embodiment, y is an integer between 4 and 10. In another embodiment, y is an integer between 6 and 10. In a further embodiment, y is 8. In another embodiment, w is an integer of between 0 and 4. In a further embodiment, w is 0. In another embodiment, y is an integer between 4 and 10 and w is 0. In a further embodiment, y is an integer between 6 and 10 and w is 0. In another embodiment, y is 8 and w is 0.

In an embodiment, the compound of Formula I has the structure:

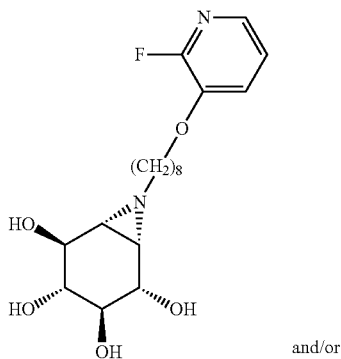

and/or

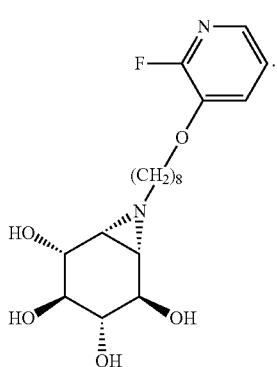

In some embodiments of the compound of Formula I, wherein all of $R^2$, $R^3$, $R^4$ and $R^5$ are —OH and X is F and the compound of Formula I(a)(i), $R^1$ is

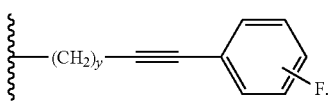

In another embodiment, $R^1$ is

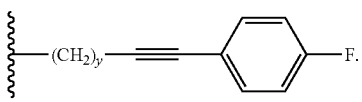

In a further embodiment, y is an integer between 2 and 8. In another embodiment, y is an integer between 3 and 5. In a further embodiment, y is 4.

In an embodiment, the compound of Formula I has the structure:

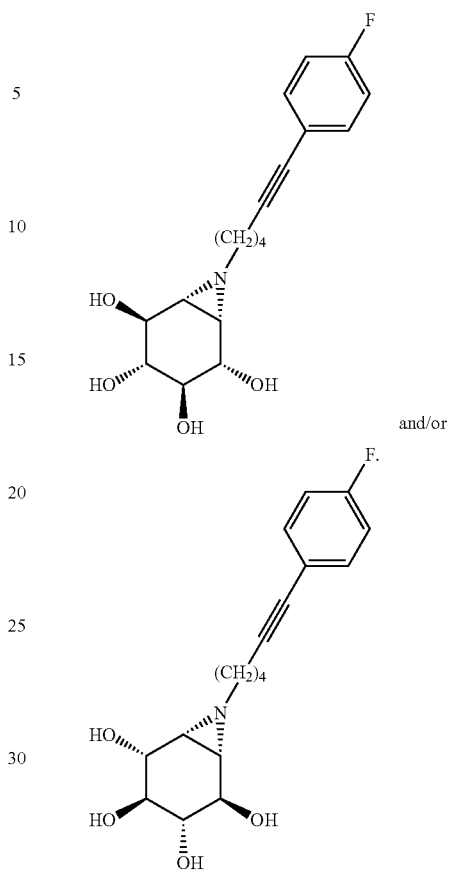

and/or

In some embodiments of the compound of Formula I, wherein all of $R^2$, $R^3$, $R^4$ and $R^5$ are —OH and X is F and the compound of Formula I(a)(i), $R^1$ is:

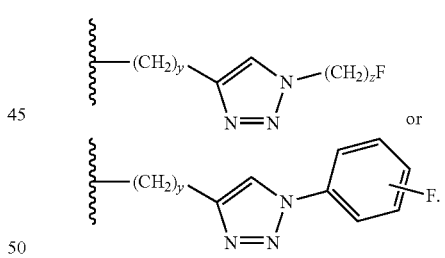

In some embodiments of the compound of Formula I, wherein all of $R^2$, $R^3$, $R^4$ and $R^5$ are —OH and X is F and the compound of Formula I(a)(i), $R^1$ is

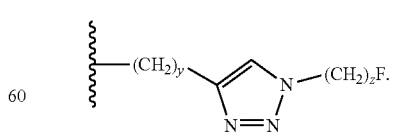

In another embodiment, y+z is an integer between 2 and 10. In a further embodiment, y+z is an integer between 4 and 7. In another embodiment of the present application, y is 1 and z is 4.

In some embodiments of the compound of Formula I, wherein all of $R^1$, $R^2$, $R^3$ and $R^4$ are —OH and X is F and the compound of Formula I(a)(i), $R^1$ is

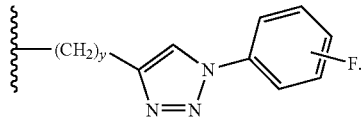

In another embodiment, y is an integer between 2 and 10. In a further embodiment, y is an integer between 4 and 6. In another embodiment of the present application, y is 5.

In an embodiment, X is H. Accordingly, in some embodiments of the present application, the compound of Formula I is a compound of Formula I(a)(ii):

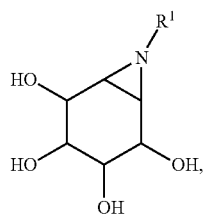

I(a)(ii)

wherein
$R^1$ is a group selected from:

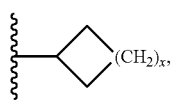

—(CH$_2$)$_y$NH(CH$_2$)$_z$CH$_3$,

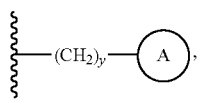

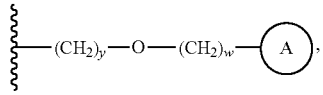

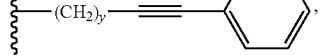

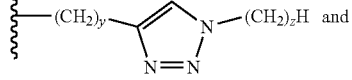

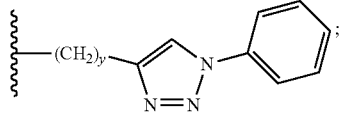

x is an integer between 1 and 20;
y is an integer between 1 and 10;
z is an integer between 1 and 10;
w is an integer between 0 and 10; and

is aryl or heteroaryl.

In some embodiments of the present application, the compound of Formula I is a compound of Formula I(a)(ii):

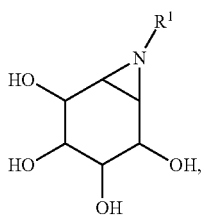

I(a)(ii)

wherein
$R^1$ is a group selected from:

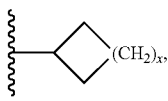

—(CH$_2$)$_y$NH(CH$_2$)$_z$CH$_3$,

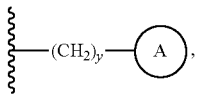

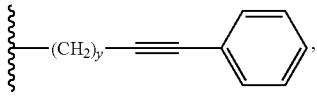

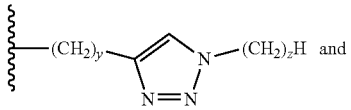

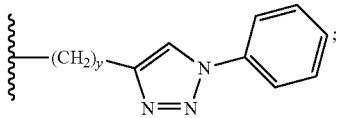

x is an integer between 1 and 20;
y is an integer between 1 and 10;
z is an integer between 1 and 10; and

is aryl or heteroaryl.

In some embodiments of the compound of Formula I, wherein all of $R^2$, $R^3$, $R^4$ and $R^5$ are —OH and X is H and the compound of Formula I(a)(ii), $R^1$ is

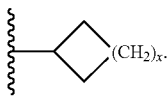

In another embodiment, x is an integer between 1 and 10. In a further embodiment, x is an integer between 2 and 7. In another embodiment of the present application, $R^1$ is a cyclopentyl or adamantyl group.

In some embodiments of the compound of Formula I, wherein all of $R^2$, $R^3$, $R^4$ and $R^5$ are —OH and X is H and the compound of Formula I(a)(ii), $R^1$ is —$(CH_2)_yNH(CH_2)_zCH_3$. In another embodiment, y+z is an integer between 2 and 10. In a further embodiment, y+z is an integer between 4 and 7. In another embodiment, y is 2. In a further embodiment, z is 4.

In some embodiments of the compound of Formula I, wherein all of $R^2$, $R^3$, $R^4$ and $R^5$ are —OH and X is H and the compound of Formula I(a)(ii), $R^1$ is

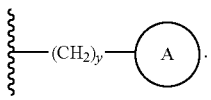

In another embodiment,

is aryl. In a further embodiment,

is phenyl. In another embodiment,

is $C_{5-10}$heteroaryl. In a further embodiment, the heteroatom in the heteroaryl group is nitrogen. In another embodiment,

is pyridyl. In a further embodiment, y is an integer between 2 and 10. In another embodiment, y is an integer between 4 and 8. In a further embodiment, y is 6.

In some embodiments of the compound of Formula I, wherein all of $R^2$, $R^3$, $R^4$ and $R^5$ are —OH and X is H and the compound of Formula I(a)(ii), $R^1$ is

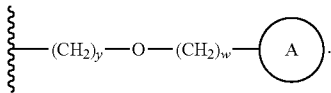

In another embodiment,

is aryl. In a further embodiment,

is phenyl. In another embodiment,

is $C_{5-10}$heteroaryl. In a further embodiment, the heteroatom in the heteroaryl group is nitrogen. In another embodiment,

is pyridyl. In another embodiment, $R^1$ is

wherein X is H. In a further embodiment, y is an integer between 4 and 10. In another embodiment, y is an integer between 6 and 10. In a further embodiment, y is 8. In another embodiment, w is an integer of between 0 and 4. In a further embodiment, w is 0. In another embodiment, y is an integer between 4 and 10 and w is 0. In a further embodiment, y is an integer between 6 and 10 and w is 0. In another embodiment, y is 8 and w is 0.

In some embodiments of the compound of Formula I, wherein all of $R^2$, $R^3$, $R^4$ and $R^5$ are —OH and X is H and the compound of Formula I(a)(ii), $R^1$ is

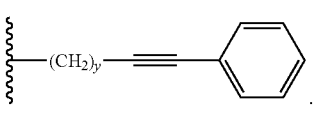

In another embodiment, y is an integer between 2 and 8. In another embodiment, y is an integer between 3 and 5. In a further embodiment, y is 4.

In some embodiments of the compound of Formula I, wherein all of $R^2$, $R^3$, $R^4$ and $R^5$ are —OH and X is H and the compound of Formula I(a)(i), $R^1$ is:

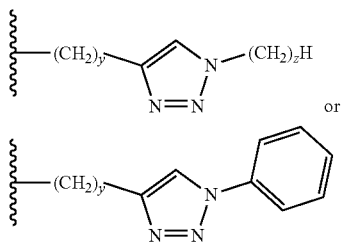

In some embodiments of the compound of Formula I, wherein all of $R^2$, $R^3$, $R^4$ and $R^5$ are —OH and X is H and the compound of Formula I(a)(ii), $R^1$ is

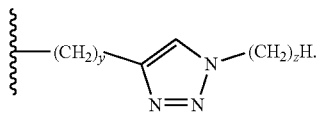

In another embodiment, y+z is an integer between 2 and 10. In a further embodiment, y+z is an integer between 4 and 7. In another embodiment of the present application, y is 1 and z is 4.

In some embodiments of the compound of Formula I, wherein all of $R^2$, $R^3$, $R^4$ and $R^5$ are —OH and X is H and the compound of Formula I(a)(ii), $R^1$ is

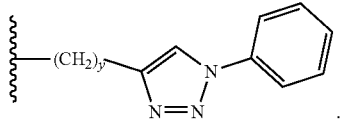

In another embodiment, y is an integer between 2 and 10. In a further embodiment, y is an integer between 4 and 6. In another embodiment of the present application, y is 5.

Dialkylated conduritol aziridine derivatives were found to be potent inhibitors of GCase in the studies reported herein. Derivatives wherein an additional —OH group is converted to an ether form may also be of interest, for example, to reduce total polar surface area and potentially increase brain penetrance. Accordingly, in an embodiment of the present application, one or two of $R^2$, $R^3$, $R^4$ and $R^5$ is —OC$_{4-20}$alkyl or —OC$_{4-20}$cycloalkyl and the others are —OH.

Accordingly, in some embodiments of the present application, the compound of Formula I is a compound of Formula I(b):

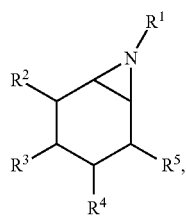

I(b)

wherein
one or two of $R^2$, $R^3$, $R^4$ and $R^5$ is —OC$_{4-20}$alkyl or —OC$_{4-20}$cycloalkyl and the others are —OH;

$R^1$ is a group selected from:

—(CH$_2$)$_x$CH$_2$X,

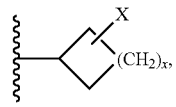

—(CH$_2$)$_y$CHX(CH$_2$)$_z$CH$_3$,
—(CH$_2$)$_y$NH(CH$_2$)$_z$CH$_2$X,

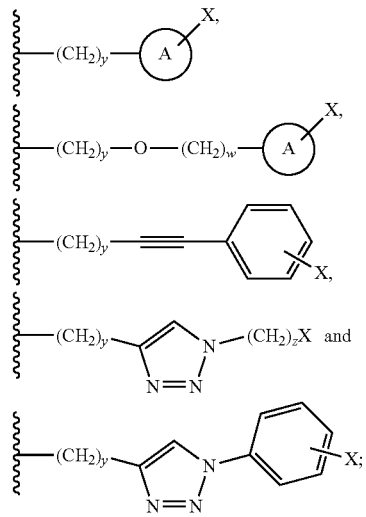

x is an integer between 1 and 20;
y is an integer between 1 and 10;
z is an integer between 1 and 10;
w is an integer between 0 and 10;

A is aryl or heteroaryl;
X is H or F; and
F is $^{19}$F or $^{18}$F.

In some embodiments of the present application, the compound of Formula I is a compound of Formula I(b):

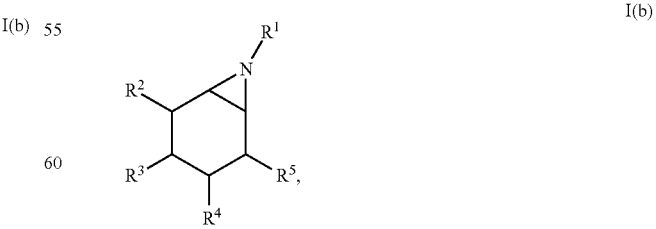

I(b)

wherein
one or two of $R^2$, $R^3$, $R^4$ and $R^5$ is —OC$_{4-20}$alkyl or —OC$_{4-20}$cycloalkyl and the others are —OH;

$R^1$ is a group selected from:

—$(CH_2)_xCH_2X$,

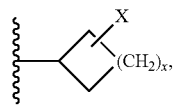

—$(CH_2)_yCHX(CH_2)_zCH_3$,
—$(CH_2)_yNH(CH_2)_zCH_2X$,

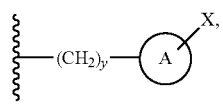

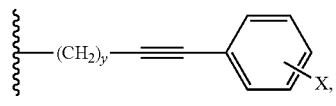

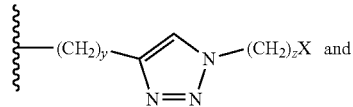

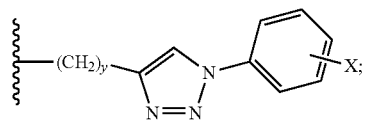

x is an integer between 1 and 20;
y is an integer between 1 and 10;
z is an integer between 1 and 10;

is aryl or heteroaryl;
X is H or F; and
F is $^{19}F$ or $^{18}F$.

In an embodiment, the compound of Formula I(b) has one or is a mixture of both of the following stereochemical configurations:

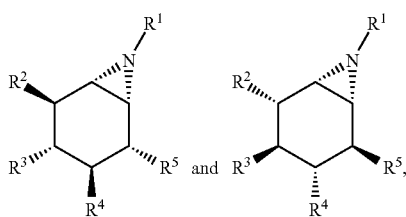

wherein $R^1$, $R^2$, $R^3$, $R^4$ and $R^5$ are as defined for the compound of Formula I(b).

In an embodiment, X is F. Accordingly, in some embodiments of the present application, the compound of Formula I is a compound of Formula I(b)(i):

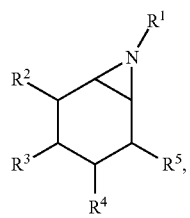

wherein
one or two of $R^2$, $R^3$, $R^4$ and $R^5$ is —$OC_{4-20}$alkyl or —$OC_{4-20}$cycloalkyl and the others are —OH;
$R^1$ is a group selected from:
—$(CH_2)_xCH_2F$,

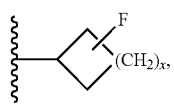

—$(CH_2)_yCHF(CH_2)_zCH_3$,
—$(CH_2)_yNH(CH_2)_zCH_2F$,

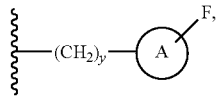

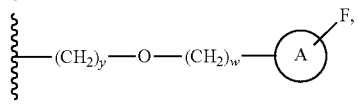

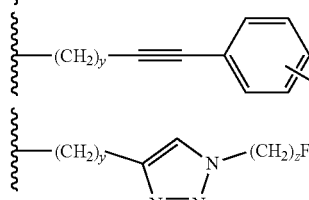

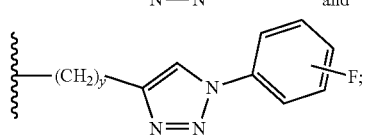

x is an integer between 1 and 20;
y is an integer between 1 and 10;
z is an integer between 1 and 10;
w is an integer between 0 and 10;

is aryl or heteroaryl; and
F is $^{19}F$ or $^{18}F$.

In some embodiments of the present application, the compound of Formula I is a compound of Formula I(b)(i):

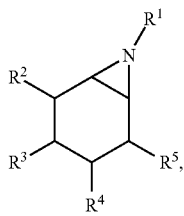

wherein
one or two of $R^2$, $R^3$, $R^4$ and $R^5$ is —$OC_{4-20}$alkyl or —$OC_{4-20}$cycloalkyl and the others are —OH;
$R^1$ is a group selected from:
—$(CH_2)_xCH_2F$,

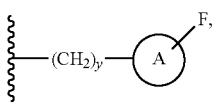

—$(CH_2)_yCHF(CH_2)_zCH_3$,
—$(CH_2)_yNH(CH_2)_zCH_2F$,

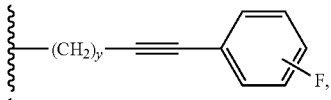

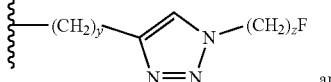

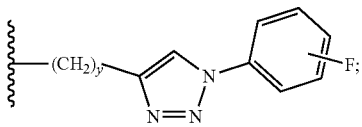

and

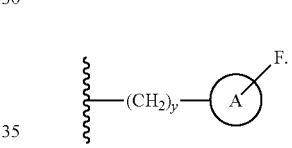

x is an integer between 1 and 20;
y is an integer between 1 and 10;
z is an integer between 1 and 10;

is aryl or heteroaryl; and
F is $^{19}F$ or $^{18}F$.

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is F and the compound of Formula I(b)(i), $R^1$ is —$(CH_2)_xCH_2F$. In another embodiment, x is an integer between 2 and 10. In another embodiment, x is an integer between 3 and 7. In a further embodiment, x is 3. In another embodiment, x is 7. In another embodiment, x is 5.

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is F and the compound of Formula I(b)(i), $R^1$ is I(b)(i)

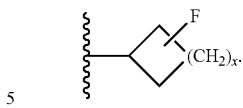

In another embodiment, x is an integer between 1 and 10. In a further embodiment, x is an integer between 2 and 7. In another embodiment, $R^5$ is a cyclopentyl or adamantyl group in which one of the hydrogen atoms has been replaced by a fluorine atom.

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is F and the compound of Formula I(b)(i), $R^1$ is —$(CH_2)_yCHF(CH_2)_zCH_3$. In another embodiment, y+z is an integer between 2 and 10. In a further embodiment, y+z is an integer between 4 and 7. In another embodiment, y is 2 and z is 4.

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is F and the compound of Formula I(b)(i), $R^1$ is —$(CH_2)_yNH(CH_2)_zCH_2F$. In another embodiment, y+z is an integer between 2 and 10. In a further embodiment, y+z is an integer between 4 and 7. In another embodiment of the present application, y is 2. In a further embodiment, z is 4.

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is F and the compound of Formula I(b)(i), $R^1$ is

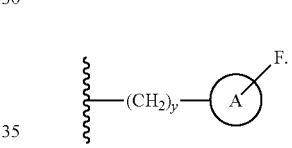

In another embodiment,

is aryl. In a further embodiment,

is phenyl. In another embodiment,

is $C_{5-10}$ heteroaryl. In a further embodiment, the heteroatom in the heteroaryl group is nitrogen. In another embodiment,

is pyridyl. In a further embodiment, y is an integer between 2 and 10. In another embodiment, y is an integer between 4 and 8. In a further embodiment, y is 6.

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is F and the compound of Formula I(b)(i), $R^1$ is

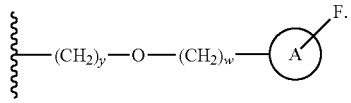

In another embodiment,

is aryl. In a further embodiment,

is phenyl. In another embodiment,

is $C_{5-10}$heteroaryl. In a further embodiment, the heteroatom in the heteroaryl group is nitrogen. In another embodiment,

is pyridyl. In another embodiment, $R^1$ is

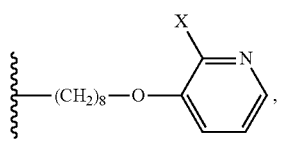

wherein X is F. In a further embodiment, y is an integer between 4 and 10. In another embodiment, y is an integer between 6 and 10. In a further embodiment, y is 8. In another embodiment, w is an integer of between 0 and 4. In a further embodiment, w is 0. In another embodiment, y is an integer between 4 and 10 and w is 0. In a further embodiment, y is an integer between 6 and 10 and w is 0. In another embodiment, y is 8 and w is 0.

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is F and the compound of Formula I(b)(i), $R^1$ is

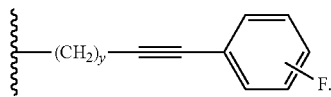

In another embodiment, $R^1$ is

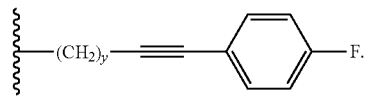

In a further embodiment, y is an integer between 2 and 8. In another embodiment of the present application, y is an integer between 3 and 5. In a further embodiment, y is 4.

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is F and the compound of Formula I(b)(i), $R^1$ is:

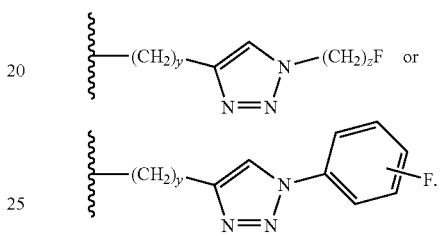

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is F and the compound of Formula I(b)(i), $R^1$ is

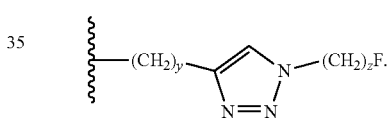

In another embodiment, y+z is an integer between 2 and 10. In a further embodiment, y+z is an integer between 4 and 7. In another embodiment, y is 1 and z is 4.

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is F and the compound of Formula I(b)(i), $R^1$ is

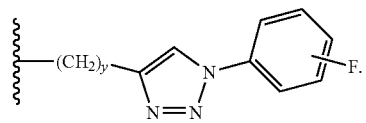

In another embodiment, y is an integer between 2 and 10. In a further embodiment, y is an integer between 4 and 6. In another embodiment, y is 5.

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is F and the compound of Formula I(b)(i), one or both of $R^2$ and $R^4$ are —$OC_{1-20}$alkyl or —$OC_{4-20}$cycloalkyl and the others of $R^2$, $R^3$, $R^4$ and $R^5$ are —OH. In another embodiment, $R^2$ is —$OC_{4-12}$alkyl or —$OC_{4-12}$cycloalkyl, $R^4$ is —$OC_{1-4}$alkyl and $R^3$ and $R^5$ are —OH. In a further embodiment, $R^2$ is —$OC_{4-10}$alkyl or —$OC_{4-12}$cycloalkyl, $R^4$ is —$OCH_3$ and $R^3$ and $R^5$ are —OH. In another embodiment of the present application, $R^2$ is —O-n-hexyl, —O-n-octyl, —O-isopropyl, —O-isobutyl, —O— cyclopentyl or —O-adamantyl, $R^4$ is —OCH$_3$ and $R^3$ and $R^5$ are —OH. In a further embodiment, $R^2$ is —O-n-hexyl, $R^4$ is —OCH$_3$ and $R^3$ and $R^5$ are —OH.

In some embodiments of the compound of Formula I, wherein one or two of $R^2$, $R^3$, $R^4$ and $R^5$ is —OC$_{1-20}$alkyl or —OC$_{4-20}$cycloalkyl, the others are —OH and X is F and the compound of Formula I(b)(i), $R^2$ is —OC$_{1-20}$alkyl or —OC$_{4-20}$cycloalkyl and $R^3$, $R^4$ and $R^5$ are —OH. In another embodiment, $R^2$ is —OC$_{4-12}$alkyl or —OC$_{4-12}$cycloalkyl, and $R^3$, $R^4$ and $R^5$ are —OH. In a further embodiment, $R^2$ is —OC$_{4-10}$alkyl or —OC$_{4-12}$cycloalkyl, and $R^3$, $R^4$ and $R^5$ are —OH. In another embodiment of the present application, $R^2$ is —O-n-hexyl, —O-n-octyl, —O-isopropyl, —O-isobutyl, —O-cyclopentyl or —O-adamantyl, and $R^3$, $R^4$ and $R^5$ are —OH. In a further embodiment, $R^2$ is linear C$_{4-8}$alkyl and $R^3$, $R^4$ and $R^5$ are —OH. In another embodiment, $R^2$ is —O—(CH$_2$)$_3$CH$_3$, —O—(CH$_2$)$_5$CH$_3$ or —O—(CH$_2$)$_7$CH$_3$ and $R^3$, $R^4$ and $R^5$ are —OH. In a further embodiment, $R^2$ is —O—(CH$_2$)$_7$CH$_3$ and $R^3$, $R^4$ and $R^5$ are —OH. In a further embodiment, $R^2$ is —O—(CH$_2$)$_3$CH$_3$ and $R^3$, $R^4$ and $R^5$ are —OH. In another embodiment, $R^2$ is —O—(CH$_2$)$_5$CH$_3$ and $R^3$, $R^4$ and $R^5$ are —OH.

In an embodiment, the compound of Formula I has the structure:

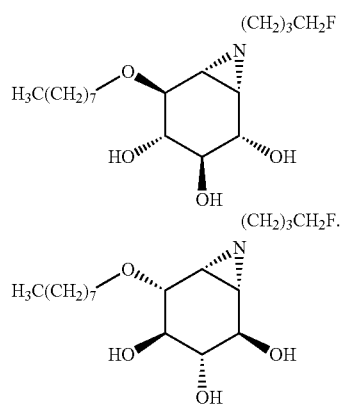

and/or

In an embodiment, the compound of Formula I has the structure:

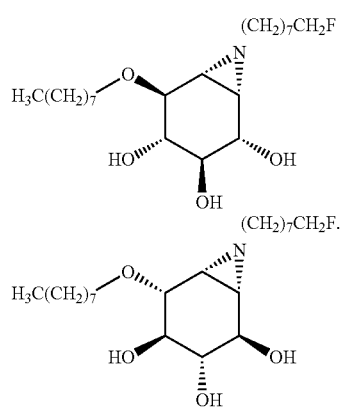

and/or

In an embodiment, X is H. Accordingly, in some embodiments of the present application, the compound of Formula I is a compound of Formula I(b)(ii):

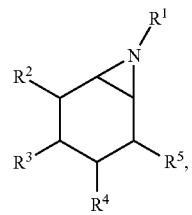

wherein one or two of $R^2$, $R^3$, $R^4$ and $R^5$ is —OC$_{4-20}$alkyl or —OC$_{4-20}$cycloalkyl and the others are —OH;

$R^1$ is a group selected from:

—(CH$_2$)$_x$CH$_3$,

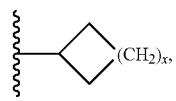

—(CH$_2$)$_y$NH(CH$_2$)$_z$CH$_3$,

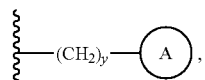

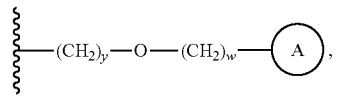

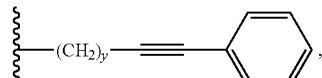

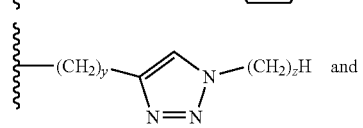

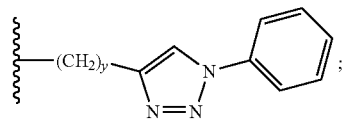

x is an integer between 1 and 20;
y is an integer between 1 and 10;
z is an integer between 1 and 10;
w is an integer between 0 and 10; and

is aryl or heteroaryl.

In some embodiments of the present application, the compound of Formula I is a compound of Formula I(b)(ii):

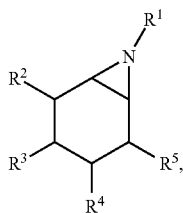

wherein
one or two of $R^2$, $R^3$, $R^4$ and $R^5$ is $-OC_{4-20}$alkyl or $-OC_{4-20}$cycloalkyl and the others are $-OH$;
$R^1$ is a group selected from:
$-(CH_2)_xCH_3$,

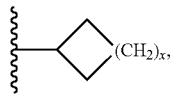

$-(CH_2)_yNH(CH_2)_zCH_3$,

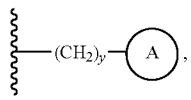

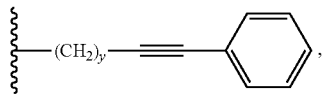

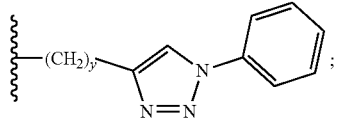

x is an integer between 1 and 20;
y is an integer between 1 and 10;
z is an integer between 1 and 10; and

is aryl or heteroaryl.

In some embodiments of the compound of Formula I, wherein one or two of $R^2$, $R^3$, $R^4$ and $R^5$ is $-OC_{1-20}$alkyl or $-OC_{4-20}$cycloalkyl, the others are $-OH$ and X is H and the compound of Formula I(b)(ii), $R^1$ is $-(CH_2)_xCH_3$. In another embodiment, x is an integer between 2 and 10. In another embodiment, x is an integer between 3 and 7. In a further embodiment, x is 3. In another embodiment, x is 7. In another embodiment, x is 5.

In some embodiments of the compound of Formula I, wherein one or two of $R^2$, $R^3$, $R^4$ and $R^5$ is $-OC_{1-20}$alkyl or $-OC_{4-20}$cycloalkyl, the others are $-OH$ and X is H and the compound of Formula I(b)(ii), $R^1$ is

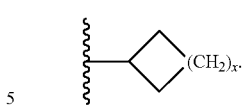

In another embodiment, x is an integer between 1 and 10. In a further embodiment, x is an integer between 2 and 7. In another embodiment, $R^5$ is a cyclopentyl or adamantyl.

In some embodiments of the compound of Formula I, wherein one or two of $R^2$, $R^3$, $R^4$ and $R^5$ is $-OC_{1-20}$alkyl or $-OC_{4-20}$cycloalkyl, the others are $-OH$ and X is H and the compound of Formula I(b)(ii), $R^1$ is $-(CH_2)_yNH(CH_2)_zCH_3$. In another embodiment, y+z is an integer between 2 and 10. In a further embodiment, y+z is an integer between 4 and 7. In another embodiment of the present application, y is 2. In a further embodiment, z is 4.

In some embodiments of the compound of Formula I, wherein one or two of $R^2$, $R^3$, $R^4$ and $R^5$ is $-OC_{1-20}$alkyl or $-OC_{4-20}$cycloalkyl, the others are $-OH$ and X is H and the compound of Formula I(b)(ii), $R^1$ is

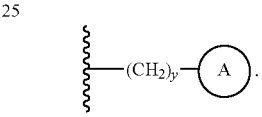

In another embodiment,

is aryl. In a further embodiment,

is phenyl. In another embodiment,

is $C_{5-10}$heteroaryl. In a further embodiment, the heteroatom in the heteroaryl group is nitrogen. In another embodiment,

is pyridyl. In a further embodiment, y is an integer between 2 and 10. In another embodiment, y is an integer between 4 and 8. In a further embodiment, y is 6.

In some embodiments of the compound of Formula I, wherein one or two of $R^2$, $R^3$, $R^4$ and $R^5$ is $-OC_{1-20}$alkyl or $-OC_{4-20}$cycloalkyl, the others are $-OH$ and X is H and the compound of Formula I(b)(ii), $R^1$ is

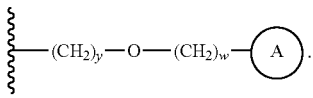

In another embodiment,

is aryl. In a further embodiment,

is phenyl. In another embodiment,

is $C_{5-10}$heteroaryl. In a further embodiment, the heteroatom in the heteroaryl group is nitrogen. In another embodiment,

is pyridyl. In another embodiment, $R^1$ is

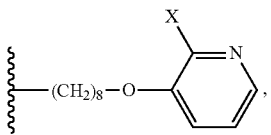

wherein X is H. In a further embodiment, y is an integer between 4 and 10. In another embodiment, y is an integer between 6 and 10. In a further embodiment, y is 8. In another embodiment, w is an integer of between 0 and 4. In a further embodiment, w is 0. In another embodiment, y is an integer between 4 and 10 and w is 0. In a further embodiment, y is an integer between 6 and 10 and w is 0. In another embodiment, y is 8 and w is 0.

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is H and the compound of Formula I(b)(ii), $R^1$ is

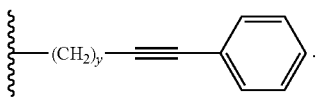

In a further embodiment, y is an integer between 2 and 8. In another embodiment of the present application, y is an integer between 3 and 5. In a further embodiment, y is 4.

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is H and the compound of Formula I(b)(ii), $R^1$ is:

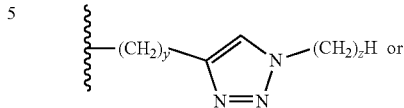

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is H and the compound of Formula I(b)(ii), $R^1$ is

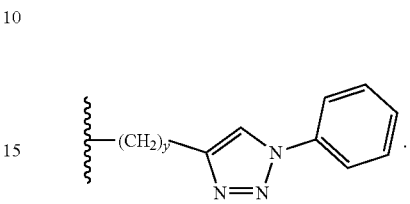

In another embodiment, y+z is an integer between 2 and 10. In a further embodiment, y+z is an integer between 4 and 7. In another embodiment, y is 1 and z is 4.

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is H and the compound of Formula I(b)(ii), $R^1$ is

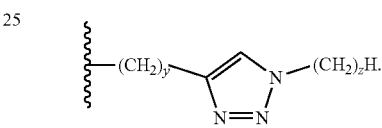

In another embodiment, y is an integer between 2 and 10. In a further embodiment, y is an integer between 4 and 6. In another embodiment, y is 5.

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is H and the compound of Formula I(b)(ii), one or both of $R^2$ and $R^4$ are —$OC_{1-20}$alkyl or —$OC_{4-20}$cycloalkyl and the others of $R^2$, $R^3$, $R^4$ and $R^5$ are —OH. In another embodiment, $R^2$ is —$OC_{4-12}$alkyl or —$OC_{4-12}$cycloalkyl, $R^4$ is —$OC_{1-4}$alkyl and $R^3$ and $R^5$ are —OH. In a further embodiment, $R^2$ is —$OC_{4-10}$alkyl or —$OC_{4-12}$cycloalkyl, $R^4$ is —$OCH_3$ and $R^3$ and $R^5$ are —OH. In another embodiment of the present application, $R^2$ is —O-n-hexyl, —O-n-octyl, —O-isopropyl, —O-isobutyl, —O-cyclopentyl or —O-adamantyl, $R^4$ is —$OCH_3$ and $R^2$ and $R^4$ are —OH. In a further embodiment, $R^2$ is —O-n-hexyl, $R^4$ is —$OCH_3$ and $R^3$ and $R^5$ are —OH.

In an embodiment, the compound of Formula I has the structure:

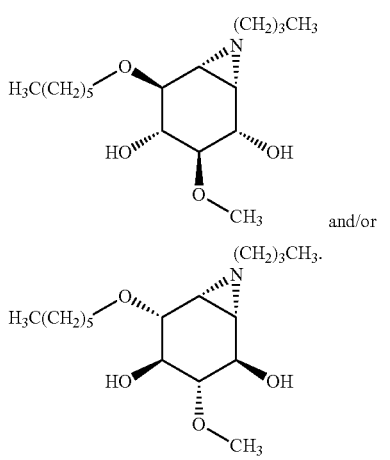 and/or

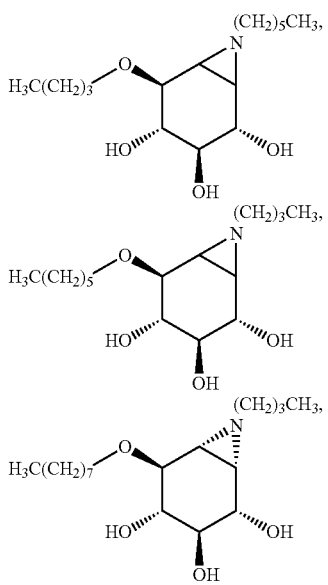

In some embodiments of the compound of Formula I, wherein one or two of $R^2$, $R^3$, $R^4$ and $R^5$ is —$OC_{1-20}$alkyl or —$OC_{4-20}$cycloalkyl, the others are —OH and X is H and the compound of Formula I(b)(ii), $R^2$ is —$OC_{1-20}$alkyl or —$OC_{4-20}$cycloalkyl and $R^3$, $R^4$ and $R^5$ are —OH. In another embodiment, $R^2$ is —$OC_{4-12}$alkyl or —$OC_{4-12}$cycloalkyl, and $R^3$, $R^4$ and $R^5$ are —OH. In a further embodiment, $R^2$ is —$OC_{4-10}$alkyl or —$OC_{4-12}$cycloalkyl, and $R^3$, $R^4$ and $R^5$ are —OH. In another embodiment of the present application, $R^2$ is —O-n-hexyl, —O-n-octyl, —O-isopropyl, —O-isobutyl, —O-cyclopentyl or —O-adamantyl, and $R^3$, $R^4$ and $R^5$ are —OH. In a further embodiment, $R^2$ is linear $C_{4-8}$-alkyl and $R^3$, $R^4$ and $R^5$ are —OH. In another embodiment, $R^2$ is —O—$(CH_2)_3CH_3$, —O—$(CH_2)_5CH_3$ or —O—$(CH_2)_7CH_3$ and $R^3$, $R^4$ and $R^5$ are —OH. In a further embodiment, $R^2$ is —O—$(CH_2)_7CH_3$ and $R^3$, $R^4$ and $R^5$ are —OH. In a further embodiment, $R^2$ is —O—$(CH_2)_3CH_3$ and $R^3$, $R^4$ and $R^5$ are —OH. In another embodiment, $R^2$ is —O—$(CH_2)_5CH_3$ and $R^3$, $R^4$ and $R^5$ are —OH.

In an embodiment, the compound of Formula I is selected from:

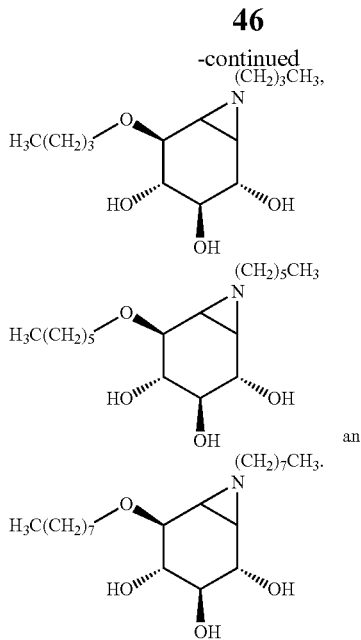

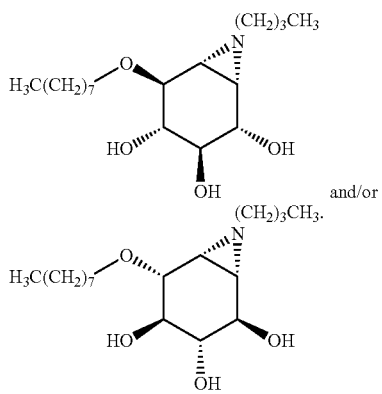 and

In an embodiment, the compound of Formula I has the structure:

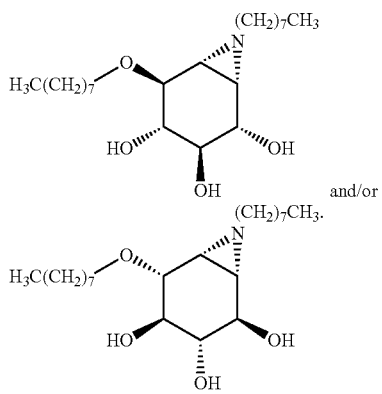

In an embodiment, the compound of Formula I has the structure:

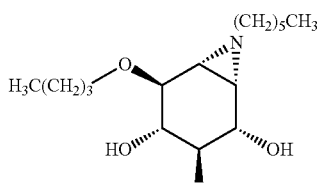

and/or

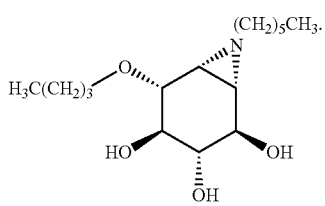

In an embodiment, the compound of Formula I has the structure:

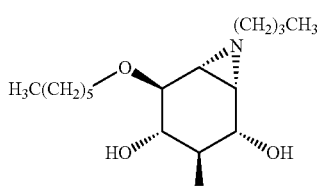

and/or

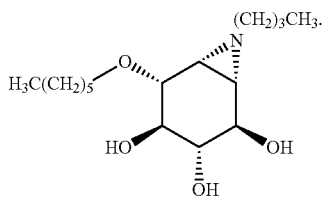

In an embodiment, the compound of Formula I has the structure:

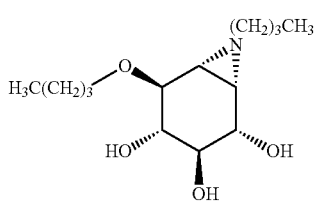

and/or

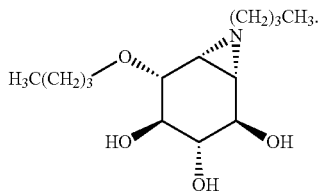

In an embodiment, the compound of Formula I has the structure:

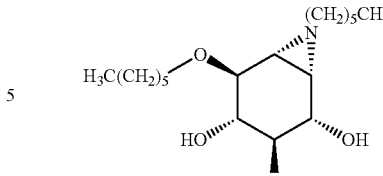

and/or

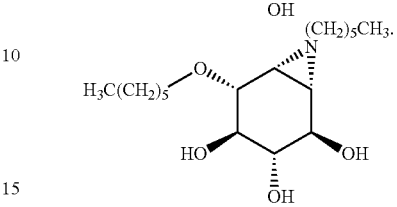

Alternatively, the fluorinated label may be on a substituent attached to an oxygen rather than the substituent attached to the nitrogen. Accordingly, in an embodiment, one of $R^2$, $R^3$, $R^4$ and $R^5$ is F-substituted —$OC_{1-20}$alkyl or F-substituted —$OC_{4-20}$cycloalkyl, two or three of the others are —OH, optionally one of the others is —$OC_{1-20}$alkyl or —$OC_{4-20}$cycloalkyl, and X is H.

Accordingly, in some embodiments of the present application, the compound of Formula I is a compound of Formula I(c):

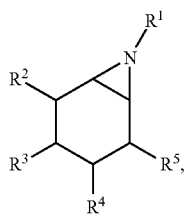

I(c)

wherein
one of $R^2$, $R^3$, $R^4$ and $R^5$ is F-substituted —$OC_{1-20}$alkyl or F-substituted —$OC_{4-20}$cycloalkyl, two or three of the others are —OH, and optionally one of the others is —$OC_{1-20}$alkyl or —$OC_{4-20}$cycloalkyl;
$R^1$ is a group selected from:
—$(CH_2)_xCH_3$,

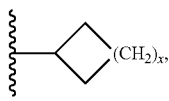

—$(CH_2)_yNH(CH_2)_zCH_3$,

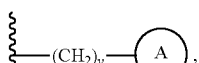

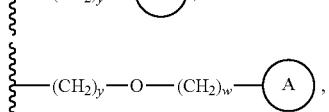

-continued

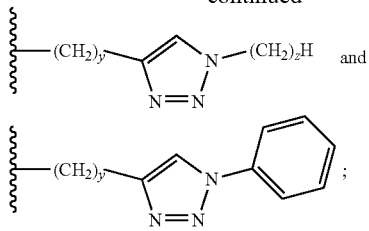 and

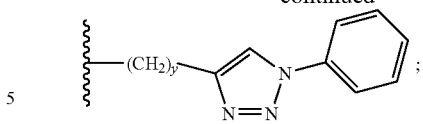 ;

x is an integer between 1 and 20;
y is an integer between 1 and 10;
z is an integer between 1 and 10; and

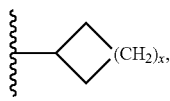

is aryl or heteroaryl.

In an embodiment, the compound of Formula I(c) has one or is a mixture of both of the following stereochemical configurations:

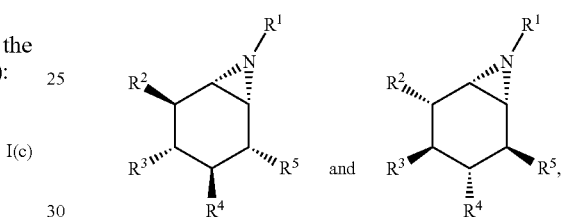

wherein $R^1$, $R^2$, $R^3$, $R^4$ and $R^5$ are as defined for the compound of Formula I(c).

In some embodiments of the compound of Formula I, wherein one of $R^2$, $R^3$, $R^4$ and $R^5$ is F-substituted —$OC_{1-20}$alkyl or F-substituted —$OC_{4-20}$cycloalkyl, two or three of the others are —OH, optionally one of the others is —$OC_{1-20}$alkyl or —$OC_{4-20}$cycloalkyl, and X is H and the compound of Formula I(c), $R^1$ is —$(CH_2)_xCH_3$. In another embodiment, x is an integer between 2 and 10. In another embodiment, x is an integer between 3 and 7. In a further embodiment, x is 3. In another embodiment, x is 7. In another embodiment, x is 5.

In some embodiments of the compound of Formula I, wherein one of $R^2$, $R^3$, $R^4$ and $R^5$ is F-substituted —$OC_{1-20}$alkyl or F-substituted —$OC_{4-20}$cycloalkyl, two or three of the others are —OH, optionally one of the others is —$OC_{1-20}$alkyl or —$OC_{4-20}$cycloalkyl, and X is H and the compound of Formula I(c), $R^1$ is

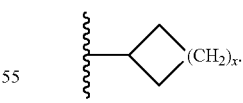

In another embodiment, x is an integer between 1 and 10. In a further embodiment, x is an integer between 2 and 7. In another embodiment, $R^1$ is a cyclopentyl or adamantyl.

In some embodiments of the compound of Formula I, wherein one of $R^2$, $R^3$, $R^4$ and $R^5$ is F-substituted —$OC_{1-20}$alkyl or F-substituted —$OC_{4-20}$cycloalkyl, two or three of the others are —OH, optionally one of the others is —$OC_{1-20}$alkyl or —$OC_{4-20}$cycloalkyl, and X is H and the compound of Formula I(c), $R^1$ is —$(CH_2)_yNH(CH_2)_zCH_3$. In another embodiment, y+z is an integer between 2 and 10.

x is an integer between 1 and 20;
y is an integer between 1 and 10;
z is an integer between 1 and 10;
w is an integer between 0 and 10; and

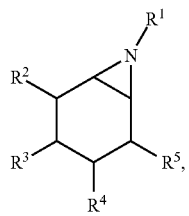

is aryl or heteroaryl.

In some embodiments of the present application, the compound of Formula I is a compound of Formula I(c):

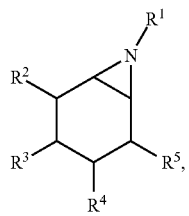   I(c)

wherein
one of $R^2$, $R^3$, $R^4$ and $R^5$ is F-substituted —$OC_{1-20}$alkyl or F-substituted —$OC_{4-20}$cycloalkyl, two or three of the others are —OH, and optionally one of the others is —$OC_{1-20}$alkyl or —$OC_{4-20}$cycloalkyl;
$R^1$ is a group selected from:
—$(CH_2)_xCH_3$,

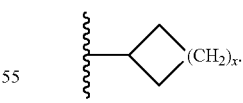

—$(CH_2)_yNH(CH_2)_zCH_3$,

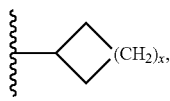,

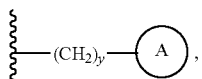,

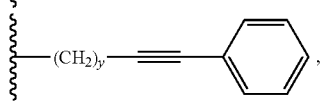 and

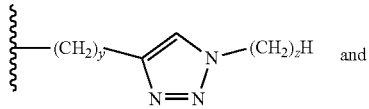

In a further embodiment, y+z is an integer between 4 and 7. In another embodiment of the present application, y is 2. In a further embodiment, z is 4.

In some embodiments of the compound of Formula I, wherein one of $R^2$, $R^3$, $R^4$ and $R^5$ is F-substituted —$OC_{1-20}$ alkyl or F-substituted —$OC_{4-20}$cycloalkyl, two or three of the others are —OH, optionally one of the others is —$OC_{1-20}$alkyl or —$OC_{4-20}$cycloalkyl, and X is H and the compound of Formula I(c), $R^1$ is

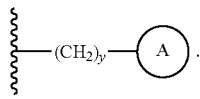

In another embodiment,

is aryl. In a further embodiment,

is phenyl. In another embodiment,

is $C_{5-10}$heteroaryl. In a further embodiment, the heteroatom in the heteroaryl group is nitrogen. In another embodiment,

is pyridyl. In a further embodiment, y is an integer between 2 and 10. In another embodiment, y is an integer between 4 and 8. In a further embodiment, y is 6.

In some embodiments of the compound of Formula I, wherein one of $R^2$, $R^3$, $R^4$ and $R^5$ is F-substituted —$OC_{1-20}$ alkyl or F-substituted —$OC_{4-20}$cycloalkyl, two or three of the others are —OH, optionally one of the others is —$OC_{1-20}$alkyl or —$OC_{4-20}$cycloalkyl, and X is H and the compound of Formula I(c), $R^1$ is

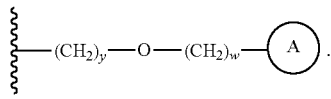

In another embodiment,

is aryl. In a further embodiment,

is phenyl. In another embodiment,

is $C_{5-10}$heteroaryl. In a further embodiment, the heteroatom in the heteroaryl group is nitrogen. In another embodiment,

is pyridyl. In another embodiment, $R^1$ is

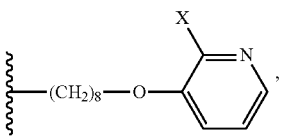

wherein X is H. In a further embodiment, y is an integer between 4 and 10. In another embodiment, y is an integer between 6 and 10. In a further embodiment, y is 8. In another embodiment, w is an integer of between 0 and 4. In a further embodiment, w is 0. In another embodiment, y is an integer between 4 and 10 and w is 0. In a further embodiment, y is an integer between 6 and 10 and w is 0. In another embodiment, y is 8 and w is 0.

In some embodiments of the compound of Formula I, wherein one of $R^2$, $R^3$, $R^4$ and $R^5$ is F-substituted —$OC_{1-20}$ alkyl or F-substituted —$OC_{4-20}$cycloalkyl, two or three of the others are —OH, optionally one of the others is —$OC_{1-20}$alkyl or —$OC_{4-20}$cycloalkyl, and X is H and the compound of Formula I(c), $R^1$ is

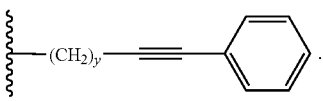

In a further embodiment, y is an integer between 2 and 8. In another embodiment of the present application, y is an integer between 3 and 5. In a further embodiment, y is 4.

In some embodiments of the compound of Formula I, wherein one of $R^2$, $R^3$, $R^4$ and $R^5$ is F-substituted —$OC_{1-20}$ alkyl or F-substituted —$OC_{4-20}$cycloalkyl, two or three of the others are —OH, optionally one of the others is —$OC_{1-20}$alkyl or —$OC_{4-20}$cycloalkyl, and X is H and the compound of Formula I(c), $R^1$ is:

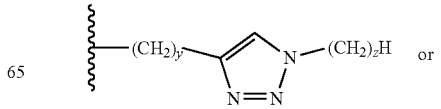 or

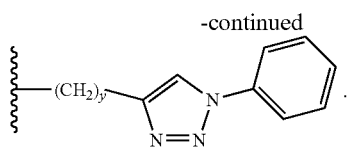

In some embodiments of the compound of Formula I, wherein one of $R^2$, $R^3$, $R^4$ and $R^5$ is F-substituted —$OC_{1-20}$alkyl or F-substituted —$OC_{4-20}$cycloalkyl, two or three of the others are —OH, optionally one of the others is —$OC_{1-20}$alkyl or —$OC_{4-20}$cycloalkyl, and X is H and the compound of Formula I(c), $R^1$ is

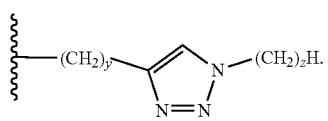

In another embodiment, y+z is an integer between 2 and 10. In a further embodiment, y+z is an integer between 4 and 7. In another embodiment, y is 1 and z is 4.

In some embodiments of the compound of Formula I, wherein one of $R^2$, $R^3$, $R^4$ and $R^5$ is F-substituted —$OC_{1-20}$alkyl or F-substituted —$OC_{4-20}$cycloalkyl, two or three of the others are —OH, optionally one of the others is —$OC_{1-20}$alkyl or —$OC_{4-20}$cycloalkyl, and X is H and the compound of Formula I(c), $R^1$ is

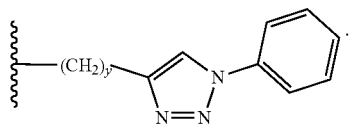

In another embodiment, y is an integer between 2 and 10. In a further embodiment, y is an integer between 4 and 6. In another embodiment, y is 5.

In some embodiments of the compound of Formula I, wherein one of $R^2$, $R^3$, $R^4$ and $R^5$ is F-substituted —$OC_{1-20}$alkyl or F-substituted —$OC_{4-20}$cycloalkyl, two or three of the others are —OH, optionally one of the others is —$OC_{1-20}$alkyl or —$OC_{4-20}$cycloalkyl, and X is H and the compound of Formula I(c), $R^2$ is F-substituted —$OC_{1-20}$alkyl or F-substituted —$OC_{4-20}$cycloalkyl and $R^3$, $R^4$ and $R^5$ are —OH. In another embodiment, $R^2$ is F-substituted —$OC_{4-12}$ alkyl or F-substituted —$OC_{4-12}$cycloalkyl, and $R^3$, $R^4$ and $R^5$ are —OH. In a further embodiment, $R^2$ is F-substituted —$OC_{4-10}$alkyl or F-substituted —$OC_{4-12}$ cycloalkyl, and $R^3$, $R^4$ and $R^5$ are —OH. In another embodiment, $R^2$ is F-substituted —O-n-hexyl, —O-n-octyl, —O-isopropyl, —O-isobutyl, —O-cyclopentyl or —O-adamantyl, and $R^3$, $R^4$ and $R^5$ are —OH. In a further embodiment, $R^2$ is F-substituted linear $C_{4-8}$alkyl and $R^3$, $R^4$ and $R^5$ are —OH. In another embodiment, $R^2$ is —O—$(CH_2)_3CH_2F$, —O—$(CH_2)_5CH_2F$ or —O—$(CH_2)_7CH_2F$ and $R^3$, $R^4$ and $R^5$ are —OH. In a further embodiment, $R^2$ is —O—$(CH_2)_7CH_2F$ and $R^3$, $R^4$ and $R^5$ are —OH. In a further embodiment, $R^2$ is —O—$(CH_2)_3CH_2F$ and $R^3$, $R^4$ and $R^5$ are —OH. In another embodiment, $R^2$ is —O—$(CH_2)_5CH_2F$ and $R^3$, $R^4$ and $R^5$ are —OH. In some embodiments of the compound of Formula I, one of $R^2$, $R^3$, $R^4$ and $R^5$ is F-substituted —$OC_{1-20}$alkyl or F-substituted —$OC_{4-20}$cycloalkyl, the others are —OH and X is H and the compound of Formula I(c), one of the OH groups in $R^3$, $R^4$ or $R^5$ is replaced with —$OC_{1-20}$alkyl or —$OC_{4-20}$cycloalkyl. In another embodiment, $R^4$ is replaced with —$OC_{1-20}$alkyl or —$OC_{4-20}$cycloalkyl. In a further embodiment, $R^4$ is replaced with —$OC_{1-12}$alkyl. In another embodiment of the present application, $R^4$ is replaced with —O—$CH_3$.

In an embodiment, the compound of Formula I has the structure:

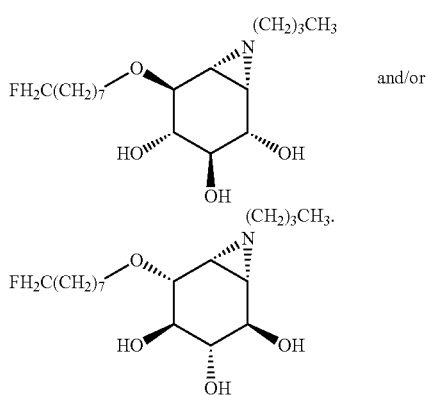

and/or

In an embodiment, the compound of Formula I has the structure:

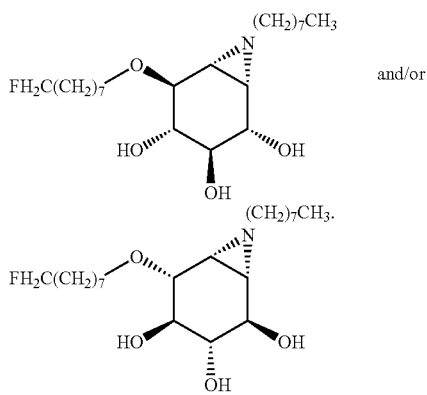

and/or

In some embodiments, an —OH group on the inositol ring is replaced with $^{18}F$. For example, such radiolabeled compounds may be prepared by radiolabeling the desired precursor using $^{18}F$-PyFluor. Accordingly, in an embodiment, one of $R^2$, $R^3$, $R^4$ and $R^5$ is F and the others are —OH.

Accordingly, in some embodiments of the present application, the compound of Formula I is a compound of Formula I(d):

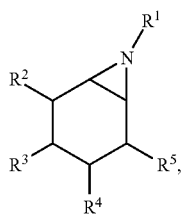

I(d)

wherein one or two of $R^2$, $R^3$, $R^4$ and $R^5$ is F and the others are —OH;

$R^1$ is a group selected from:

—$(CH_2)_xCH_3$,

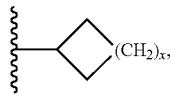

—$(CH_2)_yNH(CH_2)_zCH_3$,

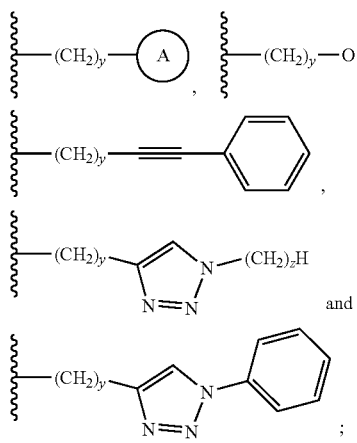

;

x is an integer between 1 and 20;
y is an integer between 1 and 10;
z is an integer between 1 and 10;
w is an integer between 0 and 10;

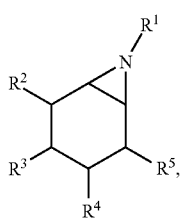

is aryl or heteroaryl; and

F is $^{19}F$ or $^{18}F$.

In some embodiments of the present application, the compound of Formula I is a compound of Formula I(d):

I(d)

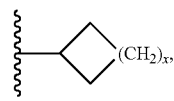

wherein one or two of $R^2$, $R^3$, $R^4$ and $R^5$ is F and the others are —OH; $R^1$ is a group selected from:

—$(CH_2)_xCH_3$,

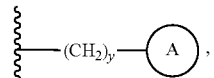

—$(CH_2)_yNH(CH_2)_zCH_3$,

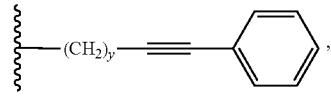

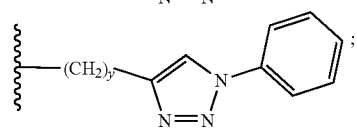

and

;

x is an integer between 1 and 20;
y is an integer between 1 and 10;
z is an integer between 1 and 10;

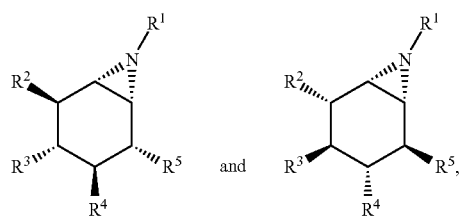

is aryl or heteroaryl; and

F is $^{19}F$ or $^{18}F$.

In an embodiment, the compound of Formula I(d) has one or is a mixture of both of the following stereochemical configurations:

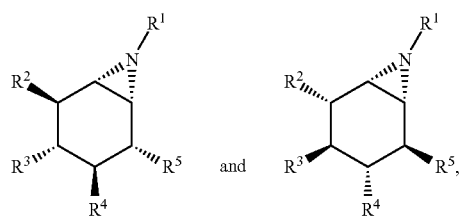

wherein $R^1$, $R^2$, $R^3$, $R^4$ and $R^5$ are as defined for the compound of Formula I(d).

In some embodiments of the compound of Formula I, wherein one of $R^2$, $R^3$, $R^4$ and $R^5$ is F and the others are —OH and the compound of Formula I(d), $R^1$ is —$(CH_2)_x$ $CH_3$. In another embodiment, x is an integer between 3 and 11. In a further embodiment, x is an integer between 5 and 8.

In some embodiments of the compound of Formula I, wherein one of $R^2$, $R^3$, $R^4$ and $R^5$ is F and the others are —OH and the compound of Formula I(d), $R^1$ is

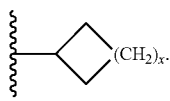

In another embodiment, x is an integer between 1 and 10. In a further embodiment, x is an integer between 2 and 7. In another embodiment of the present application, $R^5$ is a cyclopentyl or adamantyl group.

In some embodiments of the compound of Formula I, wherein one of $R^2$, $R^3$, $R^4$ and $R^5$ is F and the others are —OH and the compound of Formula I(d), $R^1$ is —$(CH_2)_y$NH$(CH_2)_z$CH$_3$. In another embodiment, y+z is an integer between 2 and 10. In a further embodiment, y+z is an integer between 4 and 7. In another embodiment of the present application, y is 2. In a further embodiment, z is 4.

In some embodiments of the compound of Formula I, wherein one of $R^2$, $R^3$, $R^4$ and $R^5$ is F and the others are —OH and the compound of Formula I(d), $R^1$ is

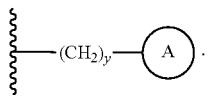

In another embodiment,

is aryl. In a further embodiment,

is phenyl. In another embodiment,

is $C_{5-10}$heteroaryl. In a further embodiment, the heteroatom in the heteroaryl group is nitrogen. In another embodiment,

is pyridyl. In a further embodiment, y is an integer between 2 and 10. In another embodiment, y is an integer between 4 and 8. In a further embodiment, y is 6.

In some embodiments of the compound of Formula I, wherein one of $R^2$, $R^3$, $R^4$ and $R^5$ is F and the others are —OH and the compound of Formula I(d), $R^1$ is

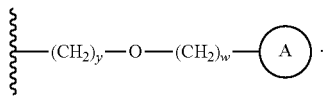

In another embodiment,

is aryl. In a further embodiment,

is phenyl. In another embodiment,

is $C_{5-10}$heteroaryl. In a further embodiment, the heteroatom in the heteroaryl group is nitrogen. In another embodiment,

is pyridyl. In another embodiment, $R^1$ is

wherein X is H. In a further embodiment, y is an integer between 4 and 10. In another embodiment, y is an integer between 6 and 10. In a further embodiment, y is 8. In another embodiment, w is an integer of between 0 and 4. In a further embodiment, w is 0. In another embodiment, y is an integer between 4 and 10 and w is 0. In a further embodiment, y is an integer between 6 and 10 and w is 0. In another embodiment, y is 8 and w is 0.

In some embodiments of the compound of Formula I, wherein one of $R^2$, $R^3$, $R^4$ and $R^5$ is F and the others are —OH and the compound of Formula I(d), $R^1$ is

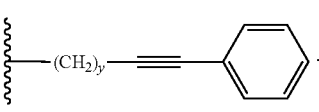

In a further embodiment, y is an integer between 2 and 8. In another embodiment of the present application, y is an integer between 3 and 5. In a further embodiment, y is 4.

In some embodiments of the compound of Formula I, wherein one of $R^2$, $R^3$, $R^4$ and $R^5$ is F and the others are —OH and the compound of Formula I(d), $R^1$ is:

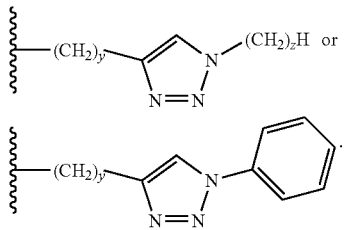

In some embodiments of the compound of Formula I, wherein one of $R^2$, $R^3$, $R^4$ and $R^5$ is F and the others are —OH and the compound of Formula I(d), $R^1$ is

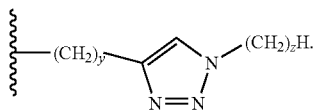

In another embodiment, y+z is an integer between 2 and 10. In a further embodiment, y+z is an integer between 4 and 7. In another embodiment of the present application, y is 1 and z is 4.

In some embodiments of the compound of Formula I, wherein one of $R^2$, $R^3$, $R^4$ and $R^5$ is F and the others are —OH and the compound of Formula I(d), $R^1$ is

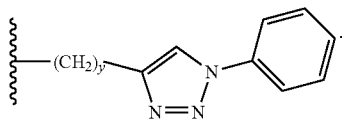

In another embodiment, y is an integer between 2 and 10. In a further embodiment, y is an integer between 4 and 6. In another embodiment of the present application, y is 5.

In some embodiments of the compound of Formula I, wherein one of $R^2$, $R^3$, $R^4$ and $R^5$ is F and the others are —OH and the compound of Formula I(d), $R^2$ is F and $R^3$, $R^4$ and $R^5$ are —OH.

In an embodiment of the compounds of Formulae I (wherein X is F), I(a) (wherein X is F), I(a)(i), I(b) (wherein X is F), I(b)(i), I(c) and I(d), X is $^{18}F$.

In an embodiment of the compounds of Formulae I (wherein X is F), I(a) (wherein X is F), I(a)(i), I(b) (wherein X is F), I(b)(i), I(c) and I(d), X is $^{19}F$.

In some embodiments, compounds of Formula I, wherein $R^1$ is —$(CH_2)_xCH_3$ or

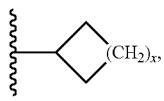

wherein x is as defined herein for the compound of Formula I are prepared via the reaction of the desired conduritol aziridine intermediate having suitable protecting groups with the desired $S_N2$ electrophile followed by deprotection under suitable conditions to obtain the compound of Formula I. In an embodiment, the $S_N^2$ electrophile is Z—$(CH_2)_x$CH$_3$ or

wherein Z is halo and x is as defined herein for the compounds of Formula I. In another embodiment of the present application, Z is bromo or iodo.

In some embodiments, compounds of Formula I, wherein $R^1$ is —$(CH_2)_xCH_2F$,

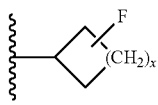

or —$(CH_2)_yCHF(CH_2)_zCH_3$, wherein x, y and z are as defined herein for the compound of Formula I are prepared via the reaction of the desired conduritol aziridine intermediate having suitable protecting groups with the desired $S_N2$ electrophile comprising an —OH group at the position where the F will ultimately be, reacting the product thereby obtained with a reagent which will provide, together with the oxygen from the —OH group, a suitable leaving group (e.g. a source of methanesulfonyl, tosyl and triflyl), reacting the product thereby obtained with a suitable source of F, followed by deprotection under suitable conditions to obtain the compound of Formula I. In an embodiment, the $S_N^2$ electrophile is Z—$(CH_2)_xCH_2OH$,

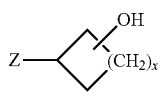

or —$(CH_2)_yCH(OH)(CH_2)_zCH_3$, wherein Z is halo and x, y and z are as defined herein for the compounds of Formula I. In another embodiment of the present application, Z is bromo or iodo.

In some embodiments, compounds of Formula I, wherein $R^1$ is —$(CH_2)_yNH(CH_2)_zCH_3$, are prepared via the reaction of the desired conduritol aziridine intermediate having suitable protecting groups with Michael acceptors such as vinyl cyanide or nitro propene followed by reduction to the primary amine then reductive amination with an aldehyde of the desired chain length followed by deprotection under suitable conditions to obtain the compound of Formula I.

In some embodiments, compounds of Formula I, wherein $R^1$ is —$(CH_2)_yNH(CH_2)_zCH_2F$ are prepared via the reaction of the desired conduritol aziridine intermediate having suitable protecting groups with Michael acceptors such as vinyl cyanide or nitro propene followed by reduction to the primary amine then reductive amination with the desired aldehyde, conjugating the product thereby obtained with a prosthetic for labelling followed by treating the product thereby obtained with a suitable source of F, followed by deprotection under suitable conditions to obtain the compound of Formula I.

In some embodiments, compounds of Formula I, wherein $R^1$ is

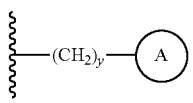

are prepared via the reaction of the desired conduritol aziridine intermediate having suitable protecting groups with the corresponding $S_N2$ electrophile having the structure

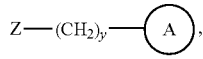, wherein Z is halo and y is as defined herein for the compounds of Formula I (such as 1-bromo-4-phenyl-hexane, -pentane, -butane, or -propane) in the presence of base followed by deprotection under suitable conditions to obtain the compound of Formula I.

In some embodiments, compounds of Formula I, wherein $R^1$ is

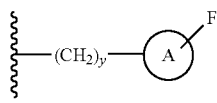

are prepared via the reaction of the corresponding conduritol aziridine intermediate, wherein $R^1$ is

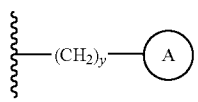

with a suitable reagent for replacing an H of the

group with F (for example, a hypervalent iodine-based reagent[62]) or alternatively via the reaction of the corresponding conduritol aziridine intermediate, wherein $R^1$ is

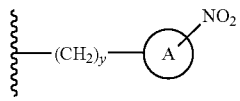

with a suitable reagent for replacing the $NO_2$ moiety with F (for example, a reagent suitable for $S_NAr$ reactions with $^{18}F$ similar to those used in the preparation of $^{18}F$-nifene) followed by deprotection, if required, under suitable conditions to obtain the compound of Formula I.

In some embodiments, compounds of Formula I, wherein $R^1$ is

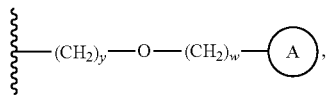

and y, w and

are as defined for the compounds of Formula I can be prepared via the reaction of the of the following compound:

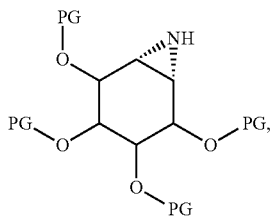

wherein PG is a suitable leaving group, with

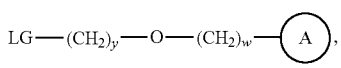, wherein LG is a suitable leaving group (such as —O-tosyl) followed by deprotection under suitable conditions to obtain the compound of Formula I. In some embodiments PG is MOM. In other embodiments, PG is another protecting group such as methoxy ethyl ethers (MEM) which require more reactive agents or longer reaction times to be removed (e.g. TFA and TMSBr) than MOM ethers. Accordingly, in some embodiments of the present application, PG is MEM.

In some embodiments, compounds of Formula I, wherein $R^1$ is

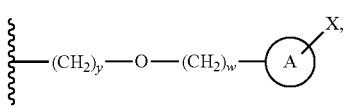

X is F and y, w and

are as defined for the compounds of Formula I can be prepared via the reaction of the of the following compound:

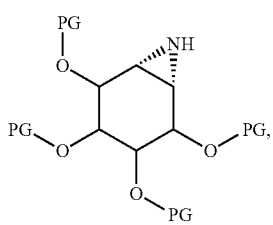

wherein PG is a suitable leaving group, with

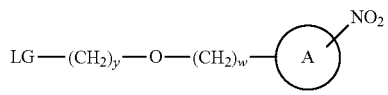

followed by replacement of the NO₂ group using a suitable source of F such as KF under suitable conditions (for example, KF/Kytofix™ in DMSO at about 160° C. for a time of about 5 hours) followed by deprotection to obtain the compound of Formula I. In some embodiments, PG is MOM. In embodiments wherein F is not $^{18}$F, other protecting groups such as methoxy ethyl ethers (MEM) may be used but require more reactive agents or longer reaction times to be removed (e.g. TFA and TMSBr) than MOM ethers. Accordingly, in some embodiments of the present application, PG is MEM.

In some embodiments, compounds of Formula I, wherein $R^1$ is

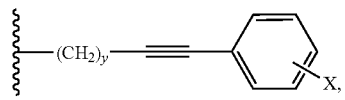

wherein X is H or F and y is as defined for the compounds of Formula I can be prepared via the reaction of the desired conduritol aziridine intermediate, optionally having suitable protecting groups with the desired $S_N2$ electrophile comprising an acetylene moiety followed by Sonogashira coupling with the desired reagent and, if required, deprotection under suitable conditions to obtain the compound of Formula I. In an embodiment, the $S_N2$ electrophile comprising an acetylene moiety has the formula

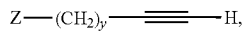

wherein Z is halo and y is as defined herein for the compounds of Formula I. In another embodiment of the present application, Z is bromo or iodo. In an embodiment, X is F and the desired reagent for Sonogashira coupling is 4-fluoroiodobenzene.

In some embodiments, compounds of Formula I, wherein $R^1$ is

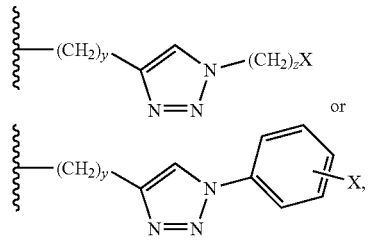

wherein X is H or F and y and z are as defined herein for the compound of Formula I are prepared by a method comprising copper-catalyzed click chemistry. In some embodiments, such compounds of Formula I are prepared via the reaction of the desired conduritol aziridine intermediate having suitable protecting groups with the desired $S_N2$ electrophile comprising an acetylene moiety followed by copper-catalyzed click chemistry with the desired azide-containing reagent and deprotection under suitable conditions to obtain the compound of Formula I. In an embodiment, the $S_N2$ electrophile comprising an acetylene moiety has the formula

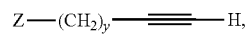

wherein Z is halo and y is as defined herein for the compounds of Formula I. In another embodiment of the present application, Z is bromo or iodo. Suitable reagents for copper-catalyzed click chemistry are known and can be selected by a person skilled in the art. In an embodiment, the conditions for the copper-catalyzed click chemistry comprise reaction in the presence of sodium ascorbate and a copper catalyst (e.g. $CuSO_4$) in a suitable solvent such as $DMF:H_2O$.

In some embodiments, compounds of Formula I, wherein one of $R^2$, $R^3$, $R^4$ and $R^5$ is F are prepared via the reaction of the corresponding conduritol aziridine intermediate wherein the desired $R^2$, $R^3$, $R^4$ and $R^5$ is —OH and the others are protected with a suitable protecting group with a suitable reagent for replacing the desired —OH with F followed by deprotection under suitable conditions to obtain the compound of Formula I. In an embodiment, the reagent is PyFluor$^{63}$.

The appropriate conduritol aziridine intermediate will depend, for example, on whether all of $R^2$, $R^3$, $R^4$ and $R^5$ are —OH (or similarly where one of $R^2$, $R^3$, $R^4$ and $R^5$ is ultimately F, and the others are —OH) versus where one or two of $R^2$, $R^3$, $R^4$ and $R^5$ is —$OC_{1-20}$alkyl or —$OC_{4-20}$cycloalkyl, and the others are —OH or where one of $R^2$, $R^3$, $R^4$ and $R^5$ is F-substituted —$OC_{1-20}$alkyl or F-substituted —$OC_{4-20}$cycloalkyl, two or three of the others are —OH, and optionally one of the others is —$OC_{1-20}$alkyl or —$OC_{4-20}$cycloalkyl.

In some embodiments, compounds of Formula I, wherein all of $R^2$, $R^3$, $R^4$ and $R^5$ are —OH (or similarly where one of $R^2$, $R^3$, $R^4$ and $R^5$ is ultimately F, and the others are —OH) are prepared via use of the following intermediate compound:

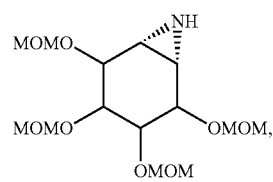

which in some embodiments of the present application, has one or both of the following stereochemical configurations:

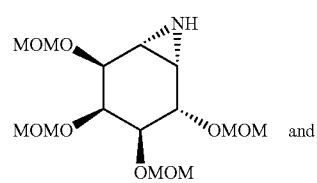

and

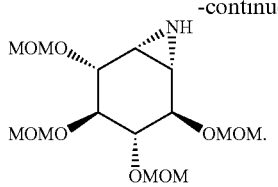

The intermediate compound in the paragraph hereinabove may be prepared, for example, according to the synthetic route in the concurrently filed application entitled "FLUORINATED N-ALKYL CONDURITOL AZIRIDINES, PROCESSES FOR THE PREPARATION THEREOF AND THEIR USE IN POSITRON-EMISSION TOMOGRAPHY (PET) IMAGING" which claims the benefit of priority from U.S. provisional application No. 62/574,563 filed on Oct. 19, 2017. In embodiments wherein F is not $^{18}$F, other protecting groups such as methoxy ethyl ethers (MEM) may be used but require more reactive agents or longer reaction times to be removed (e.g. TFA and TMSBr) than MOM ethers.

In some embodiments, compounds of Formula I, wherein one or two of $R^2$, $R^3$, $R^4$ and $R^5$ is $-OC_{1-20}$alkyl or $-OC_{4-20}$cycloalkyl, and the others are $-OH$ or where one of $R^2$, $R^3$, $R^4$ and $R^5$ is F-substituted $-OC_{1-20}$alkyl or F-substituted $-OC_{4-20}$cycloalkyl, two or three of the others are $-OH$, and optionally one of the others is $-OC_{1-20}$alkyl or $-OC_{4-20}$cycloalkyl are prepared via the use of the intermediate of Formula II:

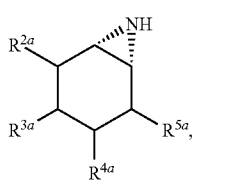

II which in some embodiments of the present application, has one or both of the following stereochemical configurations:

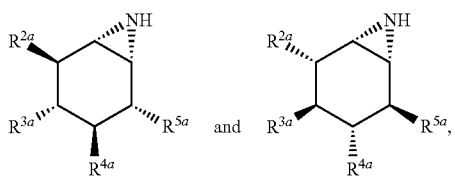

wherein, as the case may be:
(i) one or two of $R^{2a}$, $R^{3a}$, $R^{4a}$ and $R^{5a}$ is $-OC_{1-20}$alkyl or $-OC_{4-20}$cycloalkyl, and the others are -MOM; or
(ii) one of $R^{2a}$, $R^{3a}$, $R^{4a}$ and $R^{5a}$ is F-substituted $-OC_{1-20}$alkyl or F-substituted $-OC_{4-20}$cycloalkyl, two or three of the others are $-OMOM$, and optionally one of the others is $-OC_{1-20}$alkyl or $-OC_{4-20}$cycloalkyl. In embodiments wherein F is not $^{18}$F, other protecting groups such as methoxy ethyl ethers (MEM) may be used.

In some embodiments of the compound of Formula I, $R^2$ is $-OC_{1-20}$alkyl or $-OC_{4-20}$cycloalkyl and the compound of Formula II is prepared in accordance with the general reaction shown in Scheme 2:

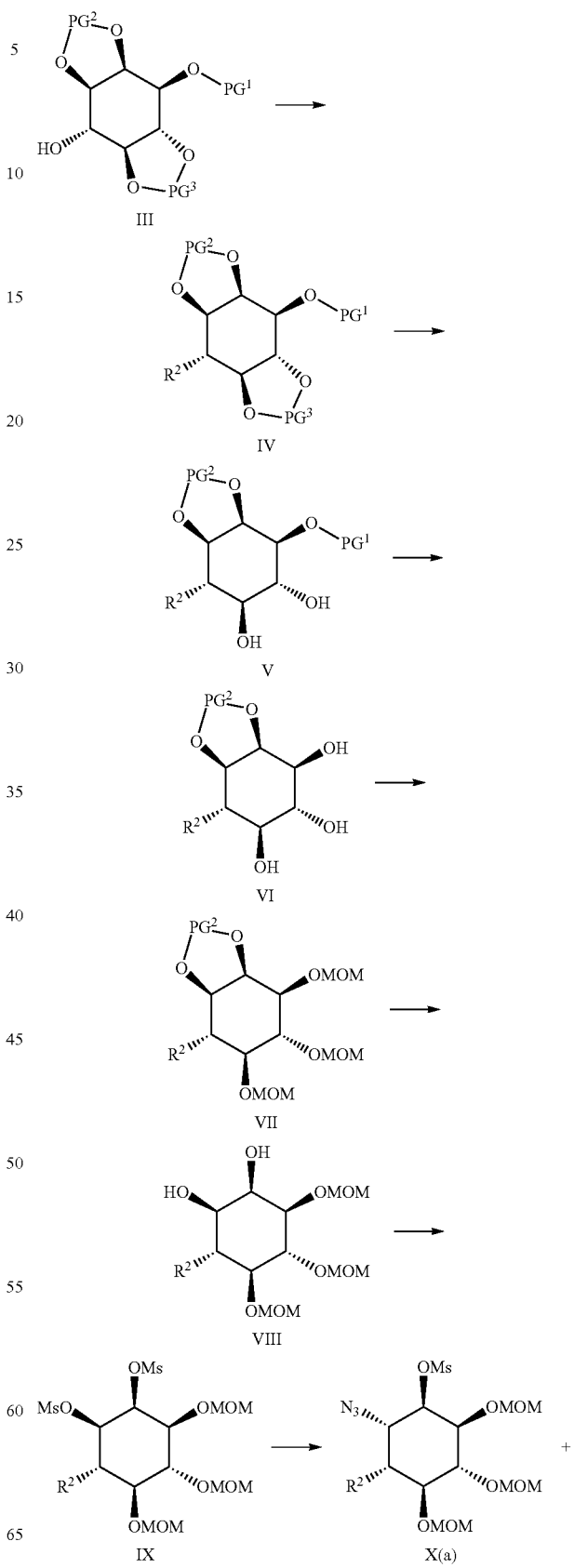

Scheme 2

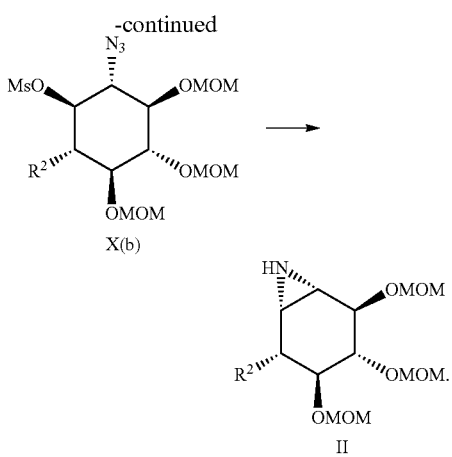

Referring to Scheme 2, the compound of Formula III is reacted with a suitable $S_N^2$ reagent under conditions to obtain the compound of Formula IV, which is selectively deprotected to remove $PG^3$ under conditions to give the compound of Formula V, which is selectively deprotected to remove $PG^1$ under conditions to give the compound of Formula VI, then protected via reaction with a source of -MOM (e.g. MOMCl) under conditions to give the compound of Formula VII, which is selectively deprotected to remove $PG^2$ under conditions to give the compound of Formula VIII, which is reacted with a reagent which will provide, together with the oxygen from the —OH group, a suitable leaving group (e.g. a source of methanesulfonyl as shown in Scheme 2 or alternatively, tosyl or triflyl) to give the compound of Formula IX, which is azidolyzed under conditions to give the mixture of the compounds of Formulae X(a) and X(b) which are reduced under conditions to give the compound of Formula II. In the compounds of Scheme 2, $PG^1$, $PG^2$ and $PG^3$ are suitable protecting groups. In some embodiments, $PG^1$ is Bn and $PG^2$ and $PG^3$ are —(CH$_3$)$_2$— or Suitable conditions can be made by a person skilled in the art in light of their common general knowledge and with reference to the Examples hereinbelow. It will also be appreciated by a person skilled in the art in light of their common general knowledge and with reference to the present application, alternative stereochemical configurations of the compounds of Formulae III, IV, V, VI, VII, VIII, IX, X(a) and/or X(b) are used when the reaction is for preparing a compound of Formula II that has the following stereochemical configuration:

or for preparing a compound of Formula II that is a mixture of the following stereochemical configurations:

In embodiments wherein one of $R^2$, $R^3$, $R^4$ and $R^5$ is F-substituted —OC$_{1-20}$alkyl or F-substituted —OC$_{4-20}$cycloalkyl, this substituent can be installed in the methods of preparation using a synthetic scheme similar to that described hereinabove for where $R^1$ is —(CH$_2$)$_x$CH$_2$F, or —(CH$_2$)$_y$CHF(CH$_2$)$_z$CH$_3$, wherein x, y and z are as defined herein for the compound of Formula I.

Nucleophilic $^{18}$F is produced by a cyclotron which has the ability to accelerate a hydride anion by using alternating electromagnets called dees. The negatively charged particle travels in a circular motion until the particle has enough kinetic energy to reach the outer diameter of the cyclotron chamber. Once traveling at sufficient speeds, the hydride ion is stripped of its electrons and the positively charged proton rapidly bombards a target made of highly pure materials. For a source of nucleophilic $^{18}$F-fluoride, $^{18}$O enriched water is used as the target material. Upon proton bombardment, the $^{18}$O is converted into $^{18}$F after releasing a neutron. When preparing radiopharmaceuticals, the following may also be considered:

Safety: In the case of a positron emitting isotope like $^{18}$F, high energy (511 keV) gamma rays will be consistently produced as positrons annihilate with surrounding electrons. These gamma rays are harmful to humans in high doses and reasonable measures should be taken to limit exposure to this ionizing energy. This means using proper shielding (lead blocks) and manually handling low amounts of activity. Working around shielding or in an automated synthesis module may, for example, limit the types of chemical techniques and/or specific reactions that can be utilized for the synthesis of compounds.

Time: All radioactive isotopes have a characteristic half-life limiting the length of time for the chemical reactions. In the case of $^{18}$F the half-life is 109.8 minutes meaning the total reaction and purification time advantageously does not exceed one half-life. Incorporation of the $^{18}$F isotope is advantageously carried out within the last steps of the processes of the present application.

Concentration: In radiopharmaceutical production, stoichiometry may be significantly different than in a typical organic reaction. For example, 1.5 mg of $^{18}$F would amount to approximately 5.5 million GBq. This amount of activity would be harmful and require significant amounts of energy to produce. However, since PET detectors are the most sensitive of the molecular imaging modalities, the amount of $^{18}$F used for a PET scan is less than 1 GBq. Although this is beneficial for limiting exposure to radioactivity it has an effect how the radiopharmaceuticals are produced. A typical production of 5.5 GBq of $^{18}$F equates to only 1.5 ng of isotope. This means that stoichiometric ratios of $^{18}$F to the chemical precursor may, for example, be about 1:10^4 or about 1:10^5.

HPLC of $^{18}$F-radiolabelled compounds can be carried out, for example, using a VP 250/10 Nucleosil 100-5 C18 Nautilus semi-preparative column (100 Å, 250×10 mm, 5 µm) or a similar column. [$^{18}$F] Fluoride (n.c.a.) may be produced, for example, on a TR-24 cyclotron (Advanced Cyclotron Systems Inc., Richmond, Canada) or a similar cyclotron via the $^{18}$O(p,n)$^{18}$F nuclear reaction. Depending on the desired activity the target may be irradiated, for example, at 18 MeV and the F-18 containing $^{18}$O enriched water may, for example, be transferred and used directly for use in synthesis, or the previously emptied target may, for example, be washed with deionized water followed by transfer to a reaction set up.

In an embodiment wherein F is $^{18}$F, radiochemical step(s) of the methods of preparation are carried out via an automated synthesizer.

Compounds and intermediates may be isolated from their reaction mixtures and may be purified using conventional laboratory techniques including, for example, solvent extraction, column chromatography using silica gel as well as alumina, distillation, crystallization, recrystallization and/or chiral separation.

Preparation of an optical isomer of compounds and intermediates may be performed, for example by the reaction of the appropriate optically active starting material under reaction conditions which will not cause racemization or alternatively the individual enantiomer or diastereomer (with more than one chiral center) is isolated by the separation of a racemic mixture using standard techniques such as fractional crystallization, chiral salt formation and/or chiral HPLC separation.

The present application also includes a composition comprising a compound of the application and a carrier. The compounds of the application are suitably formulated into compositions for administration to cells or subjects in a biologically compatible form suitable for administration in vitro or in vivo, as the case may be. Accordingly, the present application further includes a pharmaceutical composition comprising a compound of the application and a pharmaceutically acceptable carrier.

The present application also includes a composition comprising an $^{18}$F-labelled compound of the application and a carrier. The $^{18}$F-labelled compounds of the application are suitably formulated into compositions for administration to subjects in a biologically compatible form suitable for administration in vivo. Accordingly, the present application further includes a radiopharmaceutical composition for positron-emission tomography (PET) imaging of β-glucocerebrosidase activity in a subject comprising an $^{18}$F-labelled compound of the application and a radiopharmaceutically acceptable carrier.

The $^{18}$F-labelled compounds of the application may be administered to a subject in a variety of forms depending on the selected route of administration, as will be understood by those skilled in the art. In an embodiment, the $^{18}$F-labelled compounds of the application are administered parenterally and the radiopharmaceutical composition formulated accordingly. In another embodiment of the present application, the $^{18}$F-labelled compounds of the application are administered by intravenous administration and the radiopharmaceutical composition formulated accordingly. Pharmaceutical forms suitable for injectable administration or use include sterile aqueous solutions or dispersions and sterile powders for the extemporaneous preparation of sterile injectable solutions or dispersions. In all cases, the form must be sterile and must be fluid to the extent that easy syringability exists.

The present application also includes a composition comprising a non-fluorinated compound of the application and a carrier. The non-fluorinated compounds of the application are suitably formulated into compositions for administration to cells or subjects such as mammals in a biologically compatible form suitable for administration in vitro or in vivo, as the case may be. Accordingly, the present application further includes a pharmaceutical composition comprising a non-fluorinated compound of the application and a pharmaceutically acceptable carrier.

The non-fluorinated compounds of the application can be administered to a cell or a subject or used in a variety of forms depending on the selected route of administration or use, as will be understood by those skilled in the art. In an embodiment, the non-fluorinated compound of the application is administered to the subject, or used, by oral (including sublingual and buccal) or parenteral (including, intravenous, intraperitoneal, subcutaneous, intramuscular, transepithelial, nasal, intrapulmonary, intrathecal, rectal, topical, patch, pump and transdermal) administration or use and the compound formulated accordingly. For example, the non-fluorinated compounds of the application are administered or used by injection, in a spray, in a tablet/caplet, in a powder, topically, in a gel, in drops, by a patch, by an implant, by a slow release pump or by any other suitable method of administration or use, the selection of which can be made by a person skilled in the art. In another embodiment of the application, the non-fluorinated compounds of the application are freeze dried and the lyophilizates obtained, are used for example, for the preparation of products for injection. In another embodiment, the non-fluorinated compounds of the application are administered or for use parenterally. In a further embodiment, the non-fluorinated compounds of the application are administered or for use via intraperitoneal injection. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists.

IV. Methods of Imaging, Uses and Kits

The compounds of the present application are new therefore the present application includes all uses of these compounds.

The $^{18}$F-labeled compounds of the application may be useful, for example, for detection of GCase in animal-based models and humans using PET imaging. Such activity based probes may, for example, be useful molecular tools for elucidating GCase's involvement in the progression of PD, for evaluating therapeutic potential of new drugs and/or for the accurate and early diagnosis of PD.

Accordingly, the present application also includes a use of an $^{18}$F-labelled compound of the application for positron-emission tomography (PET) imaging of β-glucocerebrosidase activity in a subject; a use of an $^{18}$F-labelled compound of the application for the preparation of a radiopharmaceutical composition for positron-emission tomography (PET) imaging of β-glucocerebrosidase activity in a subject; as well as an $^{18}$F-labelled compound of the application for use in positron-emission tomography (PET) imaging of β-glucocerebrosidase activity in a subject.

The present application also includes a method for imaging β-glucocerebrosidase activity in a subject, the method comprising:
- administering an $^{18}$F-labelled compound of the application to the subject; and
- detecting the presence of retained radioactivity in the subject using positron-emission tomography (PET).

The term "retained radioactivity" as used herein refers to the radioactivity from $^{18}$F labelled compounds of the application that are bound to β-glucocerebrosidase in the subject. It will be appreciated by a person skilled in the art that the time between the administration or use of the $^{18}$F-labelled compound of the application and the detection step is sufficient to allow the $^{18}$F-labelled compound of the application to bind to the β-glucocerebrosidase in the tissue of interest which is being imaged by the PET. The time may depend, for example, on the potency of the $^{18}$F labelled compound of the application as an inhibitor to β-glucocerebrosidase and can be selected by a person skilled in the art.

In an embodiment, the imaging is for diagnosis of a disease associated with decreased β-glucocerebrosidase activity. In another embodiment of the present application, the disease is Parkinson's disease or Gaucher disease. In another embodiment, the disease is Parkinson's disease. In a further embodiment, the disease is early Parkinson's disease. In an embodiment, the diagnosis comprises comparing the retained radioactivity of the subject to a control and determining whether there is diminution in the amount or pattern of the retained radioactivity, which signals the presence of the disease.

In an embodiment, the imaging is for monitoring the progression of a disease associated with decreased β-glucocerebrosidase activity. In another embodiment, the disease is Parkinson's disease or Gaucher disease. In a further embodiment, the disease is Parkinson's disease. In another embodiment of the present application, the disease is Gaucher disease. In an embodiment, the monitoring comprises comparing the retained radioactivity of the subject obtained at a first point in time to the retained radioactivity of the subject obtained at a second point of time and determining whether there is an alteration in the amount or pattern of the retained radioactivity, which signals a change in the disease.

In an embodiment, the imaging is for monitoring the effect on β-glucocerebrosidase activity of a therapy for treatment of a disease associated with decreased β-glucocerebrosidase activity. In an embodiment, the disease is Gaucher disease and the therapy is enzyme replacement therapy. In a further embodiment, the imaging is for monitoring the effect of a therapy being investigated for use in treatment of the disease. In an embodiment, the monitoring comprises comparing the retained radioactivity of the subject obtained at a first point in time to the retained radioactivity of the subject obtained at a second point of time and determining whether there is an alteration in the amount or pattern of the retained radioactivity, which signals a change in the disease. In another embodiment, the imaging is for determining whether a subject is suitable for the therapy being investigated for use in treatment of the disease. For example, in such embodiments, the subject may have decreased β-glucocerebrosidase activity in comparison to a control and/or the subject may have a level of β-glucocerebrosidase activity within a certain range. In an embodiment, the therapy is being investigated for use in the treatment of Parkinson's disease.

In an embodiment, the imaging is of the brain of the subject.

Imaging β-glucocerebrosidase activity outside of the brain may also be useful because fibroblast cells from patients having Parkinson's disease have been shown to have reduced β-glucocerebrosidase activity. Accordingly, in another embodiment, the imaging is of a tissue comprising fibroblast cells.

The amount or dosage of the $^{18}$F-labelled compound of the application required to image the β-glucocerebrosidase activity in the subject can be readily ascertained by one of ordinary skill in the nuclear medicine art taking into account, for example, the specific activity of the compound and the radiation dosimetry. The high sensitivity of PET may allow, for example, the micro dosing of the radiotracer in the microgram to nanogram range thus addressing concerns of chemical toxicity of the imaging probe. For example, in an $^{18}$F-FDG PET scan for the average adult, 2-3 μg of imaging agent is used for a full body scan[64] and the amount of the $^{18}$F-labelled compound of the application can be determined similarly. At the micro dosing levels of the injected radiotracer, even drug candidates that may be too toxic as pharmaceuticals may be radioactively labeled and used as PET imaging probes in humans and animals.

It will be also be appreciated by the skilled person that because of the short half-life of the radioisotopes, it is often necessary to complete the final stages of the process for preparing the radiolabelled compound at or near the site of administration or use. Accordingly, the present application also includes a kit comprising a non-radiolabeled intermediate to an $^{18}$F-labelled compound of the application and optionally instructions for use of the non-radiolabeled intermediate in the preparation of the $^{18}$F-labelled compound of the application for positron-emission tomography (PET) imaging of β-glucocerebrosidase activity.

New conduritol aziridine derivatives have been prepared which are inhibitors of the lysosomal enzyme glucocerebrosidase (GCase). For example, O-octyl, N-butyl conduritol aziridine is the most potent inhibitor of GCase reported to date. Therefore the compounds of the application may also be useful, for example, in knocking out GCase in cells and/or animals.

Accordingly, the present application also includes a method of inhibiting β-glucocerebrosidase activity comprising administering a compound of the application to a cell. The present application also includes a use of a compound of the application for inhibiting β-glucocerebrosidase activity in a cell; a use of a compound of the application for preparation of a medicament for inhibiting β-glucocerebrosidase activity in a cell; and a compound of the application for use to inhibit β-glucocerebrosidase activity in a cell.

In an embodiment, the compound of the application is a non-fluorinated compound of the application.

In an embodiment, the administration or use is for the preparation of a model for investigating a disease associated with decreased β-glucocerebrosidase activity such as Gaucher disease or Parkinson's disease.

In an embodiment, the cell is in a mammal. In another embodiment, the mammal is a mouse. In another embodiment of the present application, the cell is a neuron. In a further embodiment, the cell is in the brain.

The amount or dosage of the compound of the application required to inhibit the β-glucocerebrosidase activity in the cell or subject can be readily ascertained by one of ordinary skill in the art taking into account, for example, the specific activity of the compound of the application.

An effective amount of the compound of the application is administered to or for use in a cell either in cell culture or in a subject. As used herein, the term "effective amount"

means an amount effective, at dosages and for periods of time necessary to achieve a desired result. For example, in the context of inhibiting β-glucocerebrosidase activity, an effective amount of the compound of the application is an amount that, for example, reduces the β-glucocerebrosidase activity compared to the β-glucocerebrosidase activity without administration or use of the compound of the application. Effective amounts may vary according to factors such as whether the cell is in cell culture or in a subject as well as the age, sex, weight and/or species of the subject. The amount of a given compound that will correspond to such an amount will vary depending upon various factors, such as the given compound, the pharmaceutical formulation, the route of administration or use, the type of model for studying disease being created, the identity of the subject or cell and the like, but can nevertheless be routinely determined by one skilled in the art.

Methods comprise administering to a subject or cell or use of an effective amount of the compound of the application, optionally consisting of a single administration or use, or alternatively comprising a series of administrations or uses. For example, the compound of the application is administered or for use at least once a week. However, in another embodiment, the compound is administered to the subject or for use from about one time per three weeks, or about one time per week to about once daily for a given administration or use. In another embodiment, the compounds are administered or for use 2, 3, 4, 5 or 6 times daily. It will also be appreciated that the effective dosage of a compound administered or used may increase or decrease over the course of a particular regime. Changes in dosage may result and become apparent by standard diagnostic assays known in the art.

The following non-limiting examples are illustrative of the present application:

EXAMPLES

Example 1: Preparation of Fluorophenyl Conduritol Aziridine Derivatives

1. Materials and Methods

Experimental

All buffers and reagents were obtained from Fisher Scientific or Sigma-Aldrich and used without further purification. Synthetic reactions were monitored by TLC using precoated silica gel plates (Silicycle 60F254, 0.25 mm thickness). Compounds were detected by ultraviolet light (λ=254 nm) followed by visualization with ammonium molybdate (10% w/v in 2M $H_2SO_4$), permanganate (1% w/v in water), or ninhydrin (1.5% w/v solution in butanol), with heating. Flash chromatography was performed using Silicycle silica gel (230-400 mesh). NMR spectra were obtained using a Varian Unity Inova 500 MHz spectrometer dissolving samples in the appropriate deuterated solvents ($CDCl_3$, or $CD_3OD$). Chemical shifts were reported in ppm downfield from tetramethylsilane. Low resolution ESI mass spectrometry was performed on an Advion Expression CMS Mass Spectrometer.

The compounds in the synthetic procedures of Example 1 are present as a mixture of enantiomers having the following stereochemical configurations:

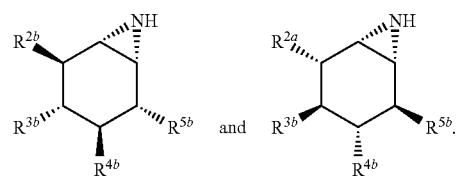

Synthesis (±)-(1R,2S,3R,4R,5S,6S)-7-(hex-5-yn-1-yl)-2,3,4,5-tetrakis(methoxymethoxy)-7-azabicyclo[4.1.0]heptane (32)

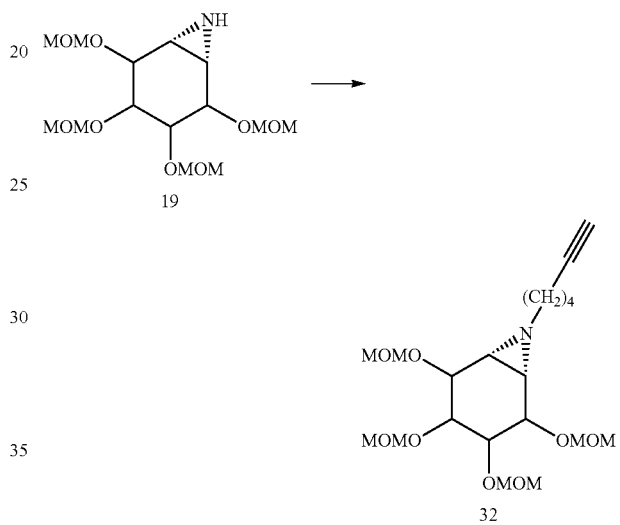

Compound 19 was prepared according to the synthetic route described in the concurrently filed application entitled "FLUORINATED N-ALKYL CONDURITOL AZIRIDINES, PROCESSES FOR THE PREPARATION THEREOF AND THEIR USE IN POSITRON-EMISSION TOMOGRAPHY (PET) IMAGING" which claims the benefit of priority from U.S. provisional application No. 62/574,563 filed on Oct. 19, 2017. 19 (700 mg, 2.075 mmol), 6-iodo-1-hexyne (0.82 mL, 6.224 mmol) and DIPEA (1.08 mL, 6.224 mmol) were dissolved in 22 mL of acetonitrile and heated to reflux for 2 days. The reaction was allowed to cool to room temperature and the solvent was removed under vacuum. The crude reaction mixture was partitioned between 200 mL of EtOAc and 200 mL of water. The aqueous layer was extracted 2 more times with 100 mL of EtOAc. The organic layers were combined and washed with brine, dried with sodium sulphate, filtered and concentrated under vacuum. The mixture was then purified using silica gel chromatography (1:1 EtOAc:Hexanes) to yield 32 (228 mg, 30%) as a colourless oil. $^1$H NMR (500 MHz, $CDCl_3$) δ 4.87-4.70 (m, 8H), 3.75 (dd, J=14.0, 5.6 Hz, 2H), 3.51 (dd, J=9.5 Hz, 1H), 3.42 (s, 6H), 3.39 (s, 6H), 3.36-3.28 (m, 1H), 2.69-2.57 (m, J=11.6, 7.0 Hz, 1H), 2.25-2.15 (m, J=6.5 Hz, 2H), 1.99-1.84 (m, 3H), 1.73-1.50 (m, 5H). $^{13}$C NMR (126 MHz, $CDCl_3$) δ 98.46, 98.06, 97.70, 97.19, 84.50, 80.32, 79.76, 78.89, 76.81, 68.52, 60.44, 56.29, 56.15, 55.94, 55.60, 43.53, 42.21, 28.67, 26.25, 18.49. LRMS (ESI): m/z Calcd for $[C_{20}H_{35}NO_8+Na]^+$: 440.2260; found: 440.5.

75

(±)-(1R,2S,3R,4R,5S,6S)-7-(6-(4-fluorophenyl)hex-5-yn-1-yl)-2,3,4,5-tetrakis(methoxymethoxy)-7-azabicyclo[4.1.0]heptane (33)

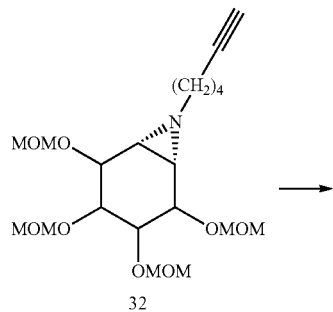

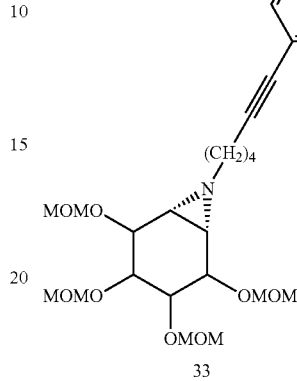

32 (75.06 mg, 0.18 mmol), triethylamine (0.1 mL, 0.72 mmol), CuI (8 mg, 0.04 mmol) and tetrakis (4 mg, 0.034 mmol) were dissolved in 3 mL of acetonitrile. To this was added 4-fluoroiodobenzene (22 µL, 0.198 mmol) and the reaction was refluxed for 20 minutes. The reaction was cooled and partitioned between 20 mL of water and 20 mL of EtOAc. The aqueous phase was extracted 2 times with 20 mL of EtOAc and the organic layers were combined. The organic portion was washed with brine, dried with sodium sulphate, filtered and concentrated under vacuum. After silica gel column chromatography (1:2 EtOAc:Hexanes) 33 (90 mg, 95%) was isolated as a colourless oil. $^1$H NMR (500 MHz, CDCl$_3$) δ 7.35 (dd, 2H), 6.96 (dd, 2H), 4.86-4.72 (m, 8H), 3.77 (t, J=7.7 Hz, 2H), 3.53 (t, J=9.5 Hz, 1H), 3.46-3.38 (m, J=7.4, 2.8 Hz, 12H), 3.38-3.31 (m, 1H), 2.69 (dd, J=11.4, 6.5 Hz, 1H), 2.41 (t, J=6.0 Hz, 2H), 2.02-1.89 (m, J=18.6, 9.0, 5.0 Hz, 2H), 1.83-1.64 (m, J=20.6, 11.3 Hz, 5H). $^{13}$C NMR (126 MHz, CDCl$_3$) δ 163.09, 161.10, 133.42, 133.35, 120.11, 115.52, 115.35, 98.42, 98.03, 97.65, 97.17, 89.75, 80.27, 79.73, 78.89, 76.77, 60.54, 56.25, 56.12, 55.88, 55.54, 43.51, 42.23, 28.89, 26.53, 19.42. LRMS (ESI): m/z Calcd for [C$_{26}$H$_{38}$FNO$_8$+H]$^+$: 512.2654; found: 512.2.

76

(±)-(1R,2S,3R,4R,5S,6S)-7-(6-(4-fluorophenyl)hex-5-yn-1-yl)-7-azabicyclo[4.1.0]heptane-2,3,4,5-tetraol (34)

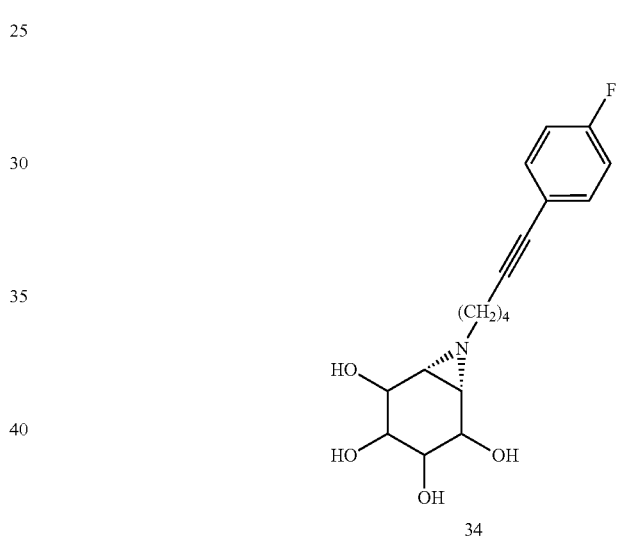

33 (50 mg, 0.098 mmol) was dissolved in 1 mL of acetonitrile and cooled to 0° C. TMSBr (256 µL, 1.960 mmol) was added slowly to the mixture and this was stirred for 40 minutes at 0° C. The reaction was quenched with 2 mL of saturated sodium bicarbonate while stirring vigorously at 0° C. and allowed to warm to room temperature. The solvent was removed under vacuum. The resulting solids were dissolved in 1:1 MeOH:CHCl$_3$, filtered and the solvents were again removed under vacuum. This crude mixture was purified using silica gel column chromatography (1:6, MeOH:CHCl$_3$) and lyophilized to yield 34 (16 mg, 49%) as an off white solid. $^1$H NMR (500 MHz, CD$_3$OD) δ 7.38 (dd, 2H), 7.03 (dd, 2H), 3.70 (dd, J=8.4, 3.5 Hz, 1H), 3.65 (d, J=8.1 Hz, 1H), 3.24 (t, 1H), 3.06 (dd, 1H), 2.49-2.36 (m, 3H), 2.30-2.19 (m, 1H), 1.96 (dd, J=6.0, 3.7 Hz, 1H), 1.81-1.70 (m, J=16.0, 8.2 Hz, 2H), 1.71-1.61 (m, J=11.8 Hz, 3H). $^{13}$C NMR (126 MHz, CD$_3$OD) δ 134.49, 134.42, 116.40, 116.23, 90.45, 80.65, 77.88, 74.08, 73.43, 73.13, 61.39, 45.89, 45.41, 29.79, 27.59, 19.86. LRMS (ESI): m/z Calcd for [C$_{18}$H$_{23}$FNO$_4$+H]$^+$: 336.160563; found: 336.6. HRMS (TOF ESI); found: 336.1615.

or

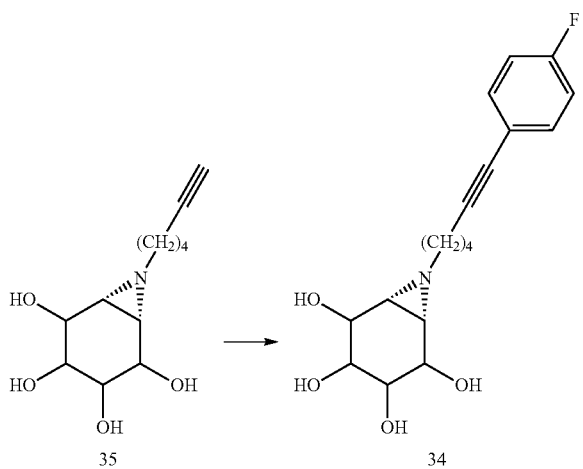

35 (21.7 mg, 0.09 mmol), triethylamine (50 µg, 0.36 mmol), CuI (4 mg, 0.02 mmol) and tetrakis (2 mg, 0.0017 mmol) were dissolved in 1.5 mL of an acetonitrile water mixture (1:1). To this was added 4-fluoroiodobenzene (11 µL, 0.099 mmol) and the reaction was heated at 90° C. for 20 minutes. The reaction was cooled and partitioned between 10 mL of water and 10 mL of EtOAc. The aqueous phase was extracted 2 times with 10 mL of EtOAc and the organic layers were combined. The organic portion was washed with brine, dried with sodium sulphate, filtered and concentrated under vacuum. After silica gel column chromatography (1:6, MeOH:CHCl$_3$) 34 (27 mg, 90%) was isolated as a white solid and matched the TLC, mass and NMR from the compound made through the alternate pathway. NMR spectra matched that of the product made from 33.

(±)-(1R,2S,3R,4R,5S,6S)-7-(hex-5-yn-1-yl)-7-azabi-cyclo[4.1.0]heptane-2,3,4,5-tetraol (35)

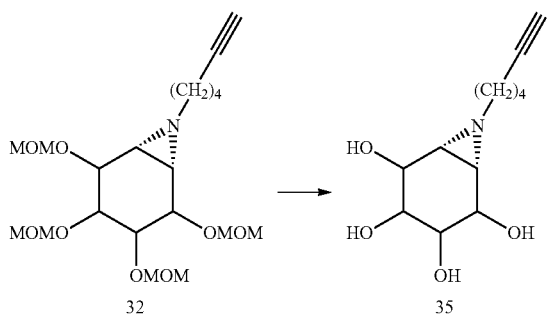

32 (200 mg, 0.480 mmol) was dissolved in 5 mL of acetonitrile and cooled to 0° C. TMSBr (1.26 mL, 9.592 mmol) was added slowly to the mixture and this was stirred for 40 minutes at 0° C. The reaction was quenched with 10 mL of saturated sodium bicarbonate while stirring vigorously at 0° C. and allowed to warm to room temperature. The solvent was removed under vacuum. The resulting solids were dissolved in 1:1 MeOH:CHCl$_3$, filtered and the solvents were again removed under vacuum. This crude mixture was purified using silica gel column chromatography (6:1 to 5:1, EtOAc:MeOH) and lyophilized to yield 35 (110 mg, 95%) as an white solid. $^1$H NMR (500 MHz, CD$_3$OD) δ 3.75 (dd, J=8.3, 3.1 Hz, 1H), 3.65 (d, J=8.1 Hz, 1H), 3.25 (t, 1H), 3.11 (t, 1H), 2.40 (dd, J=11.7, 7.0 Hz, 1H), 2.29-2.13 (m, J=14.0 Hz, 4H), 2.03-1.93 (m, 1H), 1.75-1.64 (m, 3H), 1.64-1.54 (m, 2H). $^{13}$C NMR (126 MHz, CD$_3$OD) δ 84.82, 77.52, 74.03, 73.29, 72.89, 69.65, 61.21, 45.77, 45.37, 29.55, 27.38, 18.95. LRMS (ESI): m/z Calcd for [C$_{12}$H$_{19}$NO$_4$+Na]$^+$: 264.1206; found: 264.5.

II. Results and Discussion

PET imaging can be used, for example, to non-invasively track GCase activity in a living biological organism like a mouse or human. In order to do this, a radioactive derivative, labeled with a PET isotope like $^{18}$F may be used as a radiopharmaceutical imaging agent.

In the present studies, Sonogashira coupling using commercially available non-radioactive 4-fluoro-iodobenzene (FIB) was investigated. The MOM protected aziridine 19 was alkylated using 6-iodo-alkyne to cleanly obtain alkyne 32 in 30% yield (Scheme 3). Subsequent Sonogashira coupling with FIB was shown to be efficient in refluxing acetonitrile, yielding aryl-fluorinated aziridine 33 nearly quantitatively after only 30 minutes reaction time (Scheme 3). Then, fluorinated derivative 33 was deprotected using TMSBr deprotection to yield the free aziridine 34 in 49% yield (Scheme 3). These were useful results, since high yields and rapid reactions are optimal for radiochemistry using the short-lived $^{18}$F isotope. It was also found that the MOM groups of 32 could be deprotected before Sonogashira coupling to give alkyne 35, an extremely polar derivative (Scheme 3). For Sonogashira coupling of 35 with FIB the solvent was switched to 1:1 acetonitrile:water to compensate for the increased polarity of the reactants and to ensure solubility. It was surprising that this Sonogashira coupling proceeded in the presence of water as Sonogashira couplings are often required to be anhydrous. The coupling of FIB with 35 was just as efficient as with 32 to also yield compound 34 quantitatively (Scheme 3). The robustness of this coupling may, for example, be useful for performing radiochemical reactions.

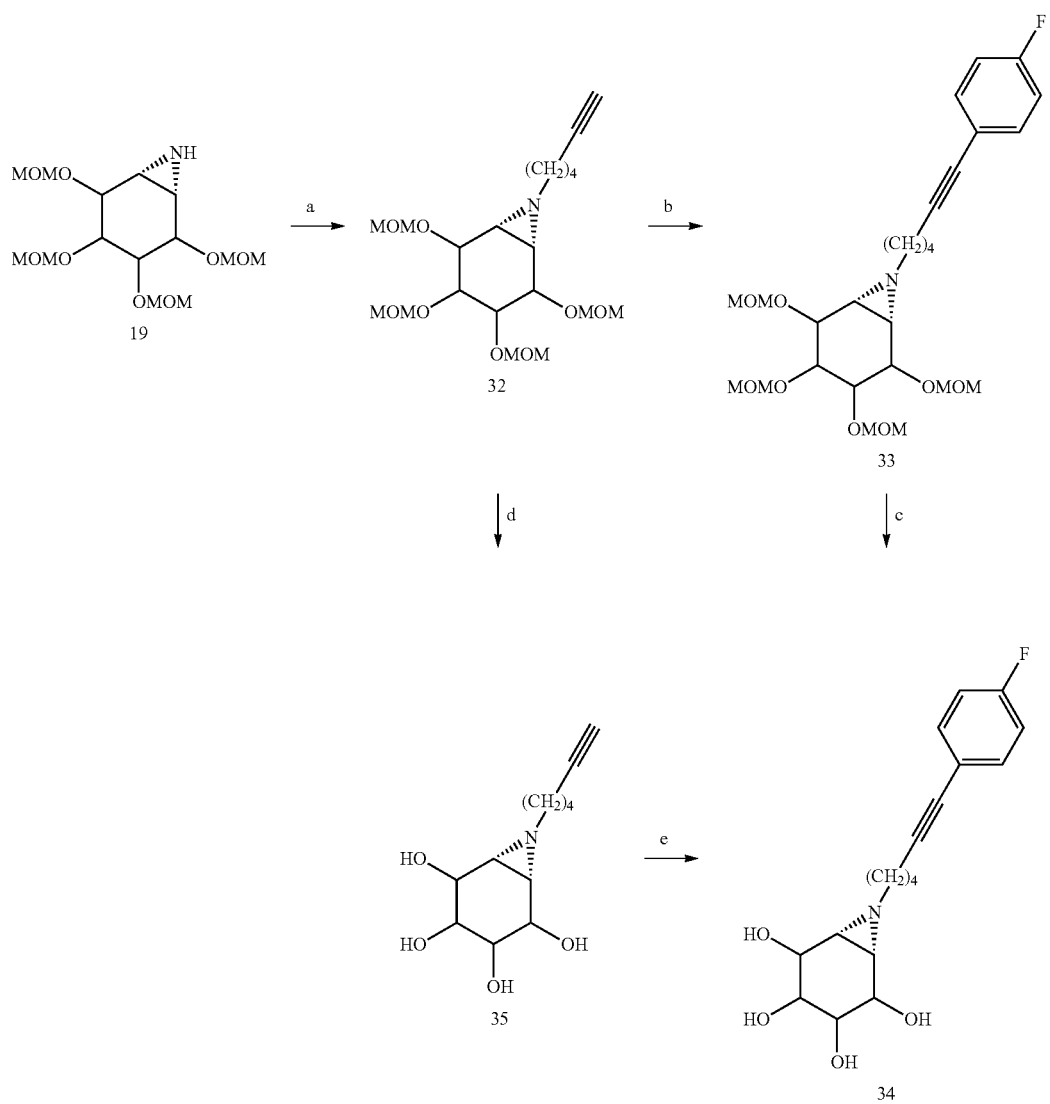

Scheme 3: Synthesis of fluorinated conduritol aziridine authentic standards for radiochemistry. (a) 6-iodo-1-hexyne, DIPEA, acetonitrile, reflux, 30%; (b) FIB, Pd(PPh$_3$)$_4$, CuI, TEA, acetonitrile, reflux, 15 min, 95%; (c) TMSBr, acetonitrile, 0° C., 30 min, 49%; (d) TMSBr, acetonitrile, 0° C., 30 min, 95%; (e) FIB, Pd(PPh$_3$)$_4$, CuI, TEA, acetonitrile:H$_2$O 1:1, reflux, 15 min, 95%.

Given the results using Sonogashira coupling with FIB, $^{18}$F-FIB may also be synthesized and then conjugated to alkyne 35 using Sonogashira coupling under suitable conditions for radiolabelling conduritol aziridines. For example, the synthesis of $^{18}$F-FIB has been published by Wuest et al. using commercially available precursor (4-iodophenyl)diphenylsulfonium triflate.[65]

Example 2: Regioselective Synthesis of O-Alkylated-N-Substituted Aziridines

I. Methods

Scheme 4 shows an overview of the reaction conditions for the synthesis of the O-alkylated-N-substituted aziridines of Example 2.

Scheme 4

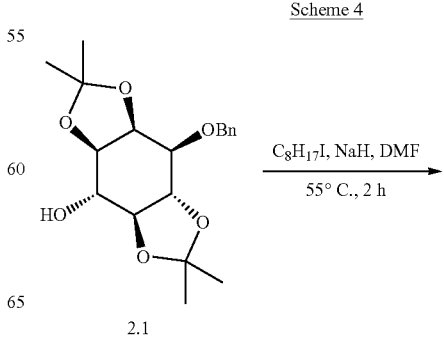

-continued

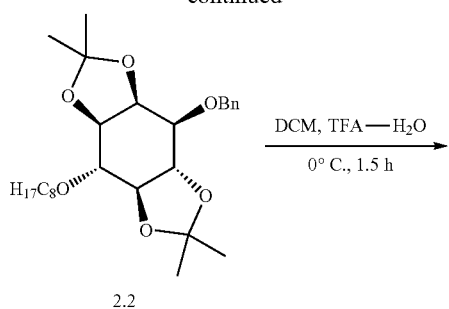
2.2

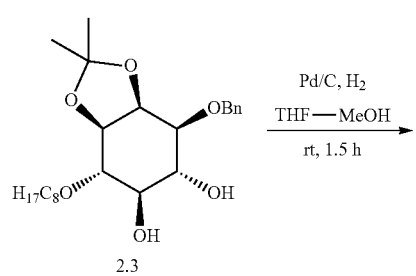
2.3

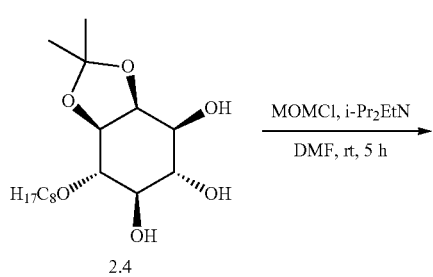
2.4

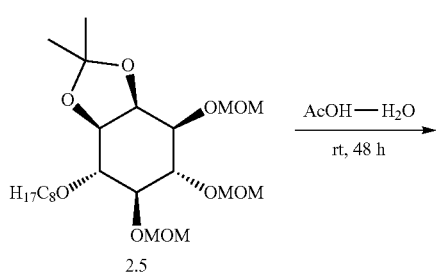
2.5

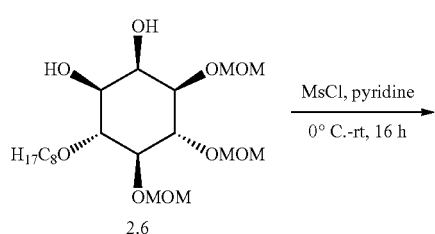
2.6

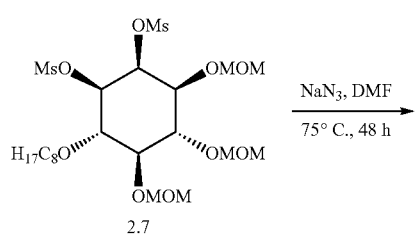
2.7

-continued

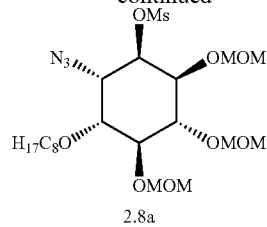
2.8a

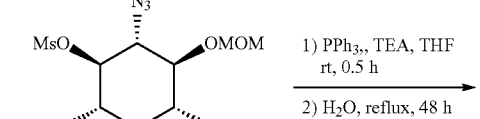
2.8b

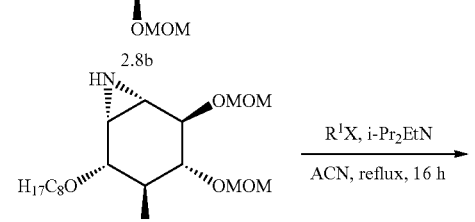
2.9

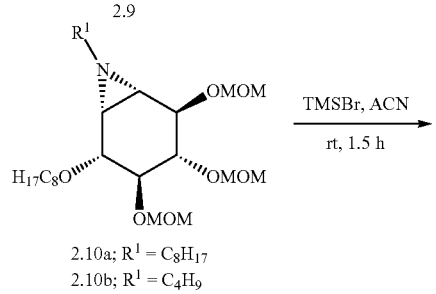
2.10a; $R^1 = C_8H_{17}$
2.10b; $R^1 = C_4H_9$

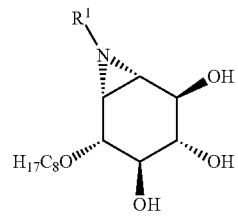
2.11a; $R^1 = C_8H_{17}$
2.11b; $R^1 = C_4H_9$

For clarity, only one stereochemical configuration is shown in Scheme 4, although the compounds are present as a mixture of enantiomers. For example, compound 2.11a is present as the following mixture:

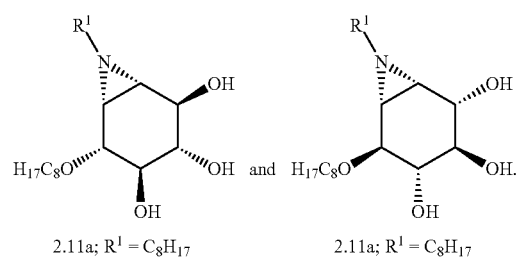
2.11a; $R^1 = C_8H_{17}$     2.11a; $R^1 = C_8H_{17}$

Synthesis of Compound 2.2:
1-Iodooctane (1.1 mL, 5.87 mmol) and then NaH (60% in oil, 190 mg, 7.82 mmol) were added to a solution of 2.1

(1.37 g, 3.91 mmol) in dry DMF (50 mL) at 0° C. under argon. The reaction mixture was heated at 55° C. for 2 h. It was then cooled to room temperature, quenched with water and extracted with ethyl acetate (50 mL×3). The combined organic phase was successively washed with water (100 mL×3), brine (100 mL), and dried ($Na_2SO_4$). After filtration, the filtrate was evaporated under reduced pressure to yield the crude product which was purified by silica gel flash column chromatography using DCM and then ethyl acetate as eluents. The purified compound 2.2 was obtained as a white solid, 1.64 g, 91%. $^1$H NMR (500 MHz, $CDCl_3$) δ 0.85-0.94 (m, 3H), 1.23-1.37 (m, 10H), 1.36 (s, 3H), 1.47 (s, 3H), 1.50 (s, 3H), 1.58 (s, 3H), 1.56-1.65 (m, 2H), 3.28 (dd, J=10.4, 9.5 Hz, 1H), 3.58 (dd, J=10.6, 6.4 Hz, 1H), 3.65-3.75 (m, 2H), 3.75 (dd, J=10.2 4.2 Hz, 1H), 3.99 (dd, J=5.2, 1.0 Hz, 1H), 4.06 (t, J=9.8 Hz, 1H), 4.32 (t, J=4.6 Hz, 1H), 4.82 (d, J=12.5 Hz, 1H), 4.92 (d, J=12.5 Hz, 1H), 7.28-7.45 (m, 5H).

Synthesis of Compound 2.3:

A mixture of trifluoroacetic acid (551 μL) in water (83 μL) was added to a solution of 2.2 (1.62 g, 3.50 mmol) in dry DCM (55 mL) at 0° C. and stirred for 1.5 h. After reaction, the mixture was neutralized with saturated $NaHCO_3$ aqueous solution. The organic layer was separated and washed with brine (25 mL), and dried ($Na_2SO_4$). After filtration the filtrate was evaporated under reduced pressure to yield the crude product which was purified by silica gel flash column chromatography using ethyl acetate:hexanes:$NH_4OH$ (2:2:0.05) as eluents. The purified compound 2.3 was obtained as a white solid, 1.26 g, 85%. $^1$H NMR (500 MHz, $CDCl_3$) δ 0.86-0.94 (m, 3H), 1.22-1.36 (m, 10H), 1.36 (s, 3H), 1.57 (s, 3H), 1.55-1.65 (m, 2H), 2.71 (s, 1H), 2.72 (s, 1H), 3.30-3.37 (m, 1H), 3.40 (dd, J=9.6, 6.9 Hz, 1H), 3.55 (dd, J=9.6, 4.0 Hz, 1H), 3.56-3.65 (m, 1H), 3.83-3.90 (m, 1H), 3.95-4.05 (m, 2H), 4.31 (dd J=4.9, 4.0 Hz, 1H), 4.78 (d, J=12.5 Hz, 1H), 4.82 (d, J=12.5 Hz, 1H), 7.29-7.46 (m, 5H).

Synthesis of compound 2.4:

A solution of 2.3 (1.26 g, 2.98 mmol) was made in a mixture of dry THE (25 mL) and dry MeOH (10 mL), and Pd/C (10%, 0.5 g) was added under argon. Hydrogen gas was bubbled through the reaction mixture for a minute and it was then kept under balloon pressure at room temperature for 1.5 h. After reaction, the mixture was filtered through a plug of celite and silica gel, and the filtrate was evaporated under reduced pressure to yield the pure product 2.4 as an oil, 0.96 g, quant. $^1$H NMR (500 MHz, $CDCl_3$) δ 0.85-0.90 (m, 3H), 1.22-1.36 (m, 10H), 1.37 (s, 3H), 1.53 (s, 3H), 1.55-1.65 (m, 2H), 2.94 (bs, 2H), 3.27-3.40 (m, 3H), 3.53-3.58 (m, 1H), 3.72-3.90 (m, 3H), 4.07-4.11 (m, 1H), 4.41 (dd, J=5.1, 4.1 Hz, 1H).

Synthesis of Compound 2.5:

N,N-Diisopropylethylamine (2 ml, 11.90 mmol) was added to a solution of 2.4 (0.98 g, 2.95 mmol) in dry DMF (10 mL) and cooled to 0° C. Chloromethyl methyl ether (1.2 mL, 15.80 mmol) was added slowly to the reaction mixture which was then stirred at room temperature for 5 h. After reaction, the mixture was slowly neutralized with saturated $NaHCO_3$ aqueous solution and extracted with $Et_2O$ (50 mL×3). The combined organic phase was successively washed with water (100 mL×3), brine (100 mL), and dried ($Na_2SO_4$). After filtration, the filtrate was evaporated under reduced pressure to yield the crude product which was purified by silica gel flash column chromatography using ethyl acetate:hexanes (2:1) as eluents. The purified compound 2.5 was obtained as an oil, 1.26 g, 92%. $^1$H NMR (500 MHz, $CDCl_3$) δ 0.85-0.91 (m, 3H), 1.22-1.36 (m, 10H), 1.38 (s, 3H), 1.57 (s, 3H), 1.55-1.65 (m, 2H), 3.42-3.65 (m, 12H), 3.75-3.85 (m, 2H), 3.92-3.98 (m, 1H), 4.10 (t, J=6.1 Hz 1H), 4.44 (dd, J=5.8, 3.9 Hz, 1H), 4.77-4.89 (m, 6H).

Synthesis of Compound 2.6:

A mixture of 80% acetic acid in water (4 ml) was added to compound 2.5 (1.26 g, 2.71 mmol) and the reaction mixture stirred at room temperature for 48 h. After reaction, the mixture was slowly neutralized with saturated $NaHCO_3$ aqueous solution and extracted with $Et_{2O}$ (75 mL×3). The combined organic phase was successively washed with water (100 mL), brine (100 mL), and dried ($Na_2SO_4$). After filtration, the filtrate was evaporated under reduced pressure to yield the crude product which was purified by silica gel flash column chromatography using ethyl acetate as eluents. The purified compound 2.6 was obtained as a white solid, 0.84 g, 73%. $^1$H NMR (500 MHz, $CDCl_3$) δ 0.80-0.85 (m, 3H), 1.15-1.32 (m, 10H), 1.52-1.61 (m, 2H), 2.88 (d, J=5.1 Hz, 1H), 3.06 (d, J=1.2 Hz, 1H), 3.37 (s, 3H), 3.38 (s, 3H), 3.40 (s, 3H), 3.30-3.50 (m, 4H), 3.61-3.79 (m, 2H), 3.85 (t, J=9.6 Hz, 1H), 4.11 (dd, J=5.8, 3.9 Hz, 1H), 4.69-4.85 (m, 6H).

Synthesis of Compound 2.7:

Methanesulfonyl chloride (0.75 mL, 9.69 mmol) was added slowly to a solution of 2.6 (0.83 g, 1.96 mmol) in dry pyridine (5 mL) at 0° C. and the reaction mixture stirred at room temperature for 16 h. After reaction, water (25 mL) was added to the reaction mixture and extracted with ethyl acetate (50 mL×3). The combined organic phase was successively washed with citric acid (0.1 M, 100 mL×2), water (100 mL), brine (100 mL), and dried ($Na_2SO_4$). After filtration, the filtrate was evaporated under reduced pressure to yield the crude product which was purified by silica gel flash column chromatography using ethyl acetate as eluents. The purified compound 2.7 was obtained as an oil, 1.14 g, quant. $^1$H NMR (500 MHz, $CDCl_3$) δ 0.85-0.95 (m, 3H), 1.22-1.37 (m, 10H), 1.55-1.65 (m, 2H), 3.16 (s, 3H), 3.21 (s, 3H), 3.45 (s, 3H), 3.46 (s, 3H), 3.49 (s, 3H), 3.40-3.51 (m, 2H), 3.60-3.79 (m, 4H), 3.86 (t, J=9.6 Hz, 1H), 4.50 (dd, J=10.1, 2.8 Hz, 1H), 4.75-4.95 (m, 6H).

Synthesis of Compound 2.8:

Sodium azide (0.14 g, 2.16 mmol) was added to a solution of 2.7 (1.14 g, 1.96 mmol) in dry DMF (20 mL) and the reaction mixture was heated at 90° C. for 48 h. After reaction, water (75 mL) was added to the reaction mixture and extracted with ethyl acetate (75 mL×3). The combined organic phase was successively washed with water (100 mL×3), brine (100 mL), and dried ($Na_2SO_4$). After filtration, the filtrate was evaporated under reduced pressure to yield the crude product mixture (2.8a+2.8b) as an oil (1.1 g) which was used for the next reaction without further purification.

Synthesis of Compound 2.9:

To a solution of 2.8a+2.8b (1.1 g) in dry THF (15 mL) was added $PPh_3$ (0.75 g) and TEA (0.65 mL) and the reaction mixture was stirred at room temperature for 0.5 h. Water (1.5 mL) was then added to the reaction mixture and was heated to reflux for 48 h. After reaction, the reaction mixture was evaporated to dryness under reduced pressure to yield the crude product which was purified by silica gel column chromatography using DCM and then ethyl acetate as eluents. The purified compound 2.9 was obtained as an oil, 0.21 g, 26% over 2 steps. $^1$H NMR (500 MHz, $CDCl_3$) δ 0.82-0.93 (m, 3H), 1.20-1.41 (m, 10H), 1.60-1.68 (m, 2H), 2.40-2.44 (m, 1H), 2.60-2.68 (m, 1H), 3.42 (s, 3H), 3.43 (s, 3H), 3.45 (s, 3H), 3.40-3.50 (m, 2H) 3.55-3.68 (m, 3H), 3.70-3.76 (m, 1H), 3.82 (d, J=7.8 Hz, 1H), 4.75-4.87 (m, 6H).

General Procedure for the Synthesis of Compounds 2.10a and 2.10b:

To a solution of 2.9 (81 mg, 0.20 mmol) in dry acetonitrile (3 mL)) was added the desired alkyl iodide (0.60 mmol) and N,N-diisopropylethylamine (105 µL, 0.60 mmol), and the reaction mixture was heated to reflux for 48 h. After reaction, the mixture was evaporated to dryness under reduced pressure to yield the crude product which was purified by silica gel column chromatography using DCM and then ethyl acetate:hexanes (1:1) as eluents.

The purified compound 2.10a was obtained as a brown oil, 88 mg, 85%. $^1$H NMR (500 MHz, CDCl$_3$) δ 0.88-0.93 (m, 6H), 1.42-1.82 (m, 20H), 1.50-1.70 (m, 6H), 1.90-1.95 (m, 1H), 2.00-2.10 (m, 1H), 2.40-2.50 (m, 1H), 3.32-3.40 (m, 1H), 3.47 (s, 3H), 3.48 (s, 3H), 3.49 (s, 3H), 3.50-3.60 (m, 2H) 3.70-3.75 (m, 1H), 3.76 (d, J=7.8 Hz, 1H), 4.75-4.88 (m, 6H).

The purified compound 2.10b was obtained as a brown oil, 92 mg, quant. $^1$H NMR (500 MHz, CDCl$_3$) δ 0.75-0.93 (m, 6H), 1.23-1.45 (m, 12H), 1.50-1.65 (m, 4H), 1.69 (d, J=6.2 Hz, 1H), 1.72 (bs, 1H), 1.95 (dd, J=6.1, 3.2 Hz, 1H), 1H 4H), 2.05-2.10 (m, 1H), 2.42-2.51 (m, 1H), 3.35 (dd, J=10.0, 8.4 Hz, 1H), 1H), 3.43 (s, 3H), 3.45 (s, 3H), 3.46 (s, 3H), 3.45-3.60 (m, 2H) 3.68-3.75 (m, 1H), 3.76 (d, J=8.3 Hz, 1H), 4.75-4.88 (m, 6H).

General Procedure for the Synthesis of Compounds 2.11a and 2.11b:

To a solution of 2.10 (0.01 mmol) in dry acetonitrile (2 mL)) was added TMSBr (0.60 mmol) and the reaction mixture was stirred at room temperature for 1.5 h. After reaction, the mixture was evaporated to dryness under reduced pressure and the residue was extracted with a mixture of CHCl$_3$:MeOH (1:1) (10 mL×3). The combined extract was evaporated to dryness under reduced pressure to yield the crude product which was purified by silica gel column chromatography using DCM:MeOH (6:1) as eluents.

The purified compound 2.11a was obtained as a brown solid, 11 mg, 29%. $^1$H NMR (500 MHz, CDCl$_3$) δ 0.83-0.94 (m, 6H), 1.20-1.45 (m, 20H), 1.50-1.70 (m, 4H), 1.73 (d, J=6.1 Hz, 1H), 1.95-2.01 (m, 1H), 2.19-2.35 (m, 2H), 3.30 (t, J=8.4 Hz, 1H), 3.47-3.57 (m, 2H), 3.57-3.68 (m, 1H), 3.70-3.78 (m, 1H), 3.85 (d, J=7.6 Hz, 1H).

The purified compound 2.11b was obtained as a brown solid, 8 mg, 23%. $^1$H NMR (500 MHz, CDCl$_3$) δ 0.85-0.98 (m, 6H), 1.23-1.45 (m, 12H), 1.50-1.70 (m, 4H), 1.75 (d, J=6.2 Hz, 1H), 1.95-2.10 (m, 1H), 2.29 (t, J=7.3 Hz, 2H), 3.30-3.40 (m, 1H), 3.45-3.60 (m, 3H), 3.72-3.78 (m, 1H), 3.90 (d, J=7.6 Hz, 1H).

II. Results and Discussion

In brief, compound 2.1 was heated at 55° C. with 1-iodooctane in presence of NaH in DMF to yield 0-octylated compound 2.2 which was selectively deprotected with TFA-H$_2$O to give 2.3 in high yield. Hydrogenation of 2.3 in presence of Pd/C/H$_2$ furnished 2.4. Protection of OH groups with MOMCl yielded 2.5 which was followed by deprotection using AcOH—H$_2$O to give 2.6 in high yield. Mesylation of 2.6 with MsCl resulted in 2.7 in quantitative yield. Azidation of 2.7 with NaN$_3$ gave a mixture of compounds 2.8a and 2.8b with full conversion. Aziridine 2.9 was obtained by treating 2.8 with PPh$_3$, TEA and H$_2$O. N-Alkylation was carried out by treating the aziridines with the corresponding alkyl halide to give 2.10a and 2.10b in high yields. Finally, deprotection of 2.10 with TMSBr furnished the dialkyl aziridines 2.11a and 2.11b in reasonable yields.

A significant advantage of the aziridine chemistry is that the structure may be efficiently and systematically modified, for example, to introduce physicochemical properties that are known to be advantageous for enhanced BBB penetrations: for example lipophilicity (log P or log D), and/or total polar surface area. For example, lipophilicity and polar surface area can be controlled by systematically increasing the length of the alkyl chains at the nitrogen of the aziridine and appending alkyl groups, for example, to the 3-OH group of the cyclitol ring. Based on the use of online calculators, the total polar surface area of dialkylated derivatives is within the typical range for passive brain uptake. Given that the N-octyl conduritol aziridine 1.7 appears to be actively transported into cell via SMIT and HMIT, while not wishing to be limited by theory, it is likely that the monoalkylated aziridines will be actively transported into the brain while the dialkylated aziridines could enter the brain largely through passive transmembrane diffusion. Since lipid solubility can increase transport rates across the BBB, compounds that are too hydrophobic can be sequestered by the capillary bed preventing the compounds from entering brain cells. Notably, the uptake rate of drugs or radiotracers that are actively transported into the brain is approximately 10 times higher than transmembrane diffusion,[66] with either mechanism leading to sufficient brain uptake of the aziridines for PET imaging.

Preparation of $^{18}$F-radiolabelled analogs to dialkylated conduritol aziridines such as 2.11a and 2.11b may be of interest, for example, as PET radiotracer candidates since: 1) glucose derivatives modified at the C-1 and C-6 carbons with hydrophobic groups are readily hydrolyzed by GCase,[67] 2) advantageous specificity may be observed since C-6 modified glucose derivatives are not readily accepted by GBA2/GBA3,[67] 3) chemical blocking of the C-3 hydroxyl group from the inositol ring with an alkyl chain may reduce polar surface area and hydrogen bonding capacity of the probe increasing the likelihood of brain uptake, 4) they potently inhibit GCase (see data in Example 3) and/or 5) two alkyl chains are now potential options for $^{18}$F-labeling.

Example 3: Enzyme Kinetics—Measuring Inactivation Rates of Inhibitors

I. Materials and Methods

Inactivation solutions contained a final concentration of 16.55 nM of Cerezyme® (Recombinant GCase) in 200 µL of Reaction Buffer (50 mM acetate, 0.2% v/v Triton X-100, 0.3% w/v sodium taurocholate, pH 5.5). The Cerezyme® was collected from leftover patient vials and had approximately 8275 nM in the vial. These enzyme Reaction Buffers were brought to 37° C. and spiked with a corresponding inhibitor to make the final inhibitor concentration either 20 nM, 40 nM, 60 nM, 80 nM, 120 nM, 160 nM and 200 nM. Once the inhibitor was added this was considered time=0 minutes. Meanwhile a 96 well plate inside a Biotek Synergy 4 hybrid multi-mode reader at 37° C. was being incubated. In the wells of the plate were waiting a high concentration (3.2 mM) of 2,4-DNP-β-Glc substrate in 180 µL of Reaction Buffer. As the inhibitor inactivation was occurring, 20 µL aliquots were taken from the inactivation solutions and diluted on the plate containing the substrate bringing the final concentration of the substrate to 4 mM. Once all the aliquots were added the solution in the wells was measured for absorbance at 400 nm for 8 minutes. At this time the measurements were paused and the next set of aliquots were taken to see how residual enzyme activity changes over time. Inactivation rates for varying inhibitor concentrations were calculated using GraphPad Prism software and Equation 2 (below). These observed rate constants were then used to calculate $k_i/K_i$ using Equation 4 (below).

II. Results and Discussion

To compare the rate of GCase inactivation of fluorinated derivative 34 to that of compound 1.7, a range of eight concentrations of the inhibitor predicted to surround the $K_i$ value were incubated with Cerezyme® (recombinant GCase), and the reaction mixtures were assayed for residual enzyme activity at different time intervals. Small aliquots of these reaction mixtures were withdrawn and diluted 20-fold in 96 well plates containing a final concentration of 4 mM of the substrate 2,4-DNP-β-D-Glc. Dilution of the reaction mixture effectively halts further inactivation by diluting the inhibitor and active site competition by excess substrate. Residual enzymatic activity at different time points and concentrations was monitored by quantifying the release of 2,4-DNP after 2,4-DNP-3-D-Glc cleavage by Cerezyme®. In Equation 1, $k_i$ is the rate constant for inhibitor inactivation of an enzyme and $K_i$ ($k_{-1}/k_1$) is the dissociation constant for the inhibitor with the enzyme otherwise known as the binding affinity.[68]

Equation 1

The ratio $k_i/K_i$ is an indication of the efficiency of an inhibitor, taking into account both binding efficiency and inactivation rate.

The velocity data obtained from this inactivation assay was fit, using the GraphPad Prism software, to Equation 2, a one phase decay equation. From this equation it is possible to obtain an observed rate constant $k_{obs}$ for the inactivation of Cerezyme by the inhibitors tested. The observed rate constant would allow for the determination of enzyme kinetic parameters $k_i$ and $K_i$.

$$Y=(Y_0-\text{Plateau})e^{(-k_{obs})x}+\text{Plateau} \quad \text{Equation 2:}$$

Inactivation data would follow Equation 3 if saturation of the enzyme's active site occurs at high inhibitor concentrations. This allows for separation of $k_i$ and $K_i$ values. The data will have an observable curve when this equation can be used effectively.

$$k_{obs} = \frac{k_i[I]}{K_i + [I]} \quad \text{Equation 3}$$

In cases where saturation cannot be observed due to rapid inactivation of the enzyme at high concentrations of inhibitor, the data will appear linear and Equation 4 must be used which gives the second order rate constant as the ratio of $k_i$ to $K_i$.

$$k_{obs} = \frac{k_i[I]}{K_i} \quad \text{Equation 4}$$

The inhibitors tested followed Equation 4 demonstrating their highly efficient rate of inactivation. The kinetic analysis of the aziridine inhibitors can be seen in FIGS. 1-2. The rapid inactivation of Cerezyme by the inhibitors tested prevented the determination of individual $K_i$ and $k_i$ values. This is because at saturating concentrations of inhibitor, the enzyme is almost instantaneously inactivated. As a result, the second order rate constant of inactivation $k_i/K_i$ was determined, a parameter still useful to compare the efficiency of fluorinated probes 34 to compound 1.7. It was previously reported that the $k_i/K_i$ values for butyl, hexyl and octyl (1.7) conduritol aziridines were 3.8±0.1 mM$^{-1}$ min$^{-1}$, 640±30 mM$^{-1}$min$^{-1}$, and 3670±70 mM$^{-1}$min$^{-1}$ respectively.[44] It is clear from this data that as carbons are added to the alkyl chain binding affinity increases dramatically.

Figure 2:
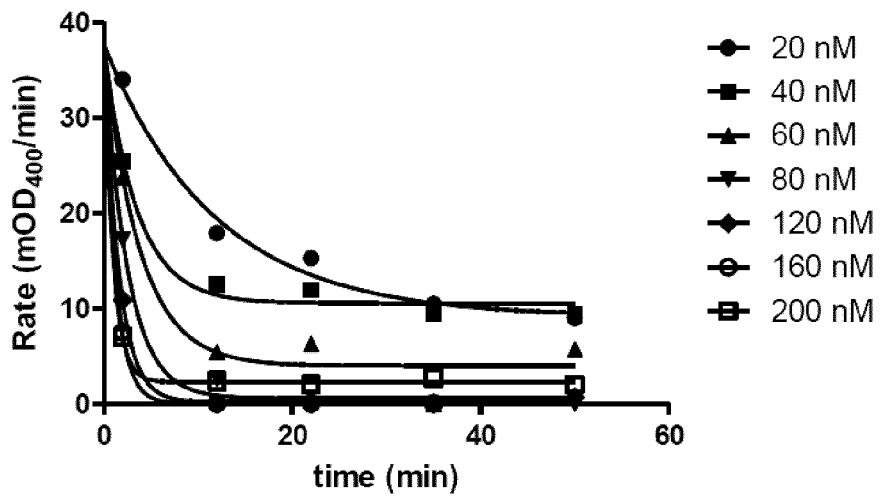
FIG. 2 shows a plot of remaining enzyme activity over time at the indicated inhibitor concentrations fitted to a one phase decay equation for a fluorinated conduritol aziridine (top) and a plot of the observed rate constants of inactivation versus the concentration of inhibitor for that compound (bottom).
Figure 2:
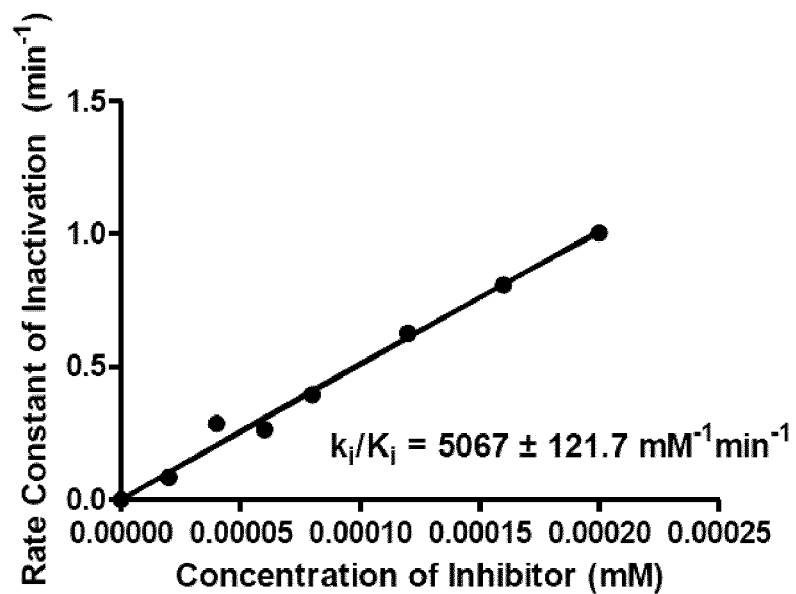
Figure 3:
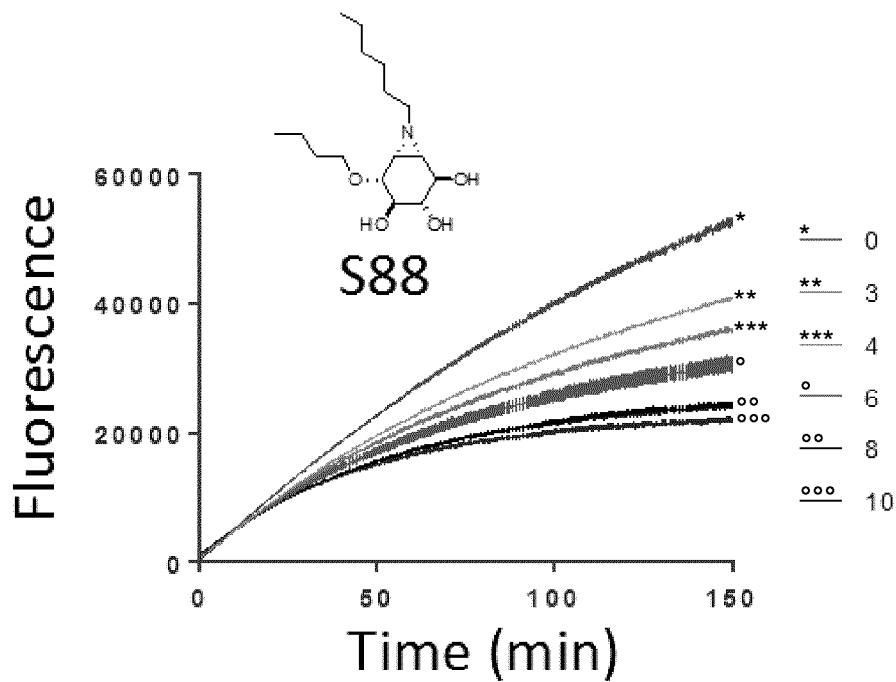
FIG. 3 shows a plot of the enzymatic turnover of 4-methylumbelliferyl β-D-glucopyranoside by β-glucocerebrosidase in the presence of conduritol aziridine derivative S88 to determine $K_{obs}$ at various inhibitor concentrations vs time (top) and a corresponding secondary plot of $K_{obs}$ vs concentration of inhibitor for that compound (bottom).
Figure 3:
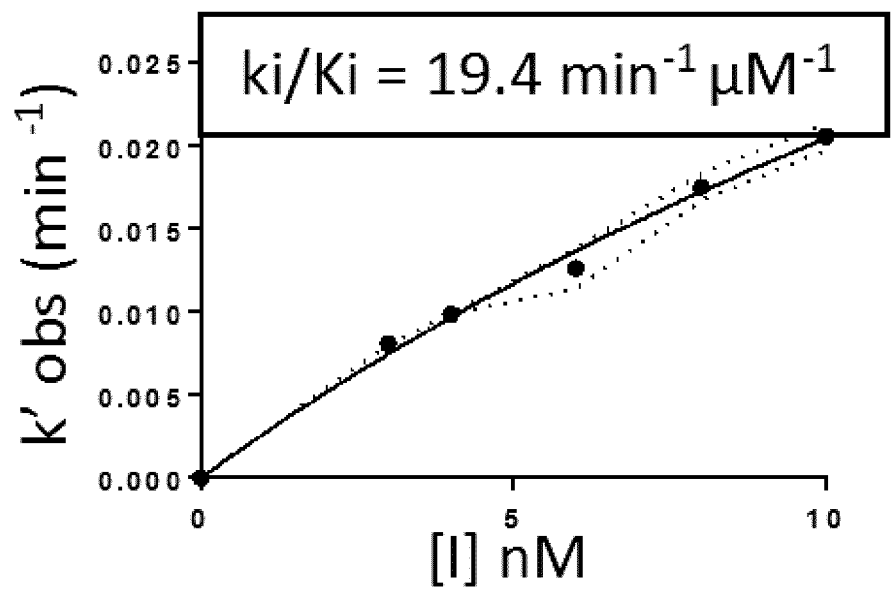
Figure 4:
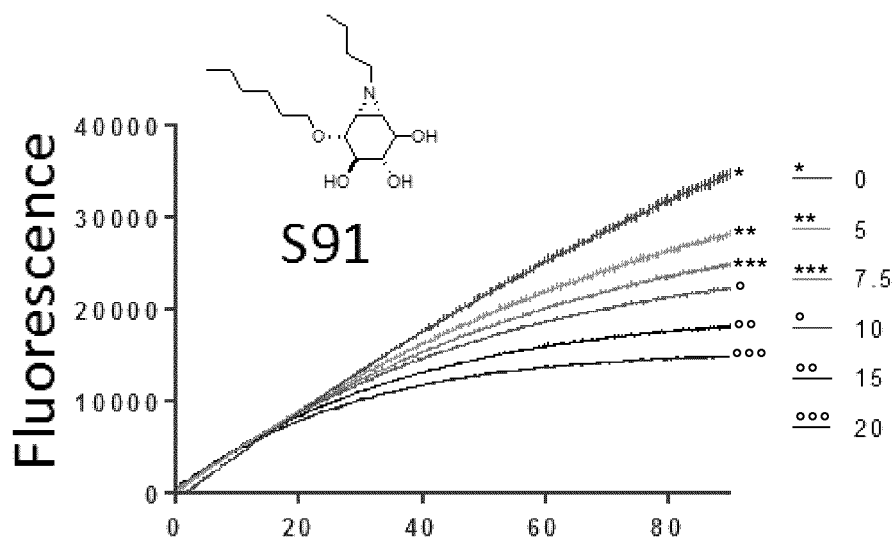
FIG. 4 shows a plot of the enzymatic turnover of 4-methylumbelliferyl β-D-glucopyranoside by β-glucocerebrosidase in the presence of conduritol aziridine derivative S91 to determine $K_{obs}$ at various inhibitor concentrations vs time (top) and a corresponding secondary plot of $K_{obs}$ vs concentration of inhibitor for that compound (bottom).
Figure 4:
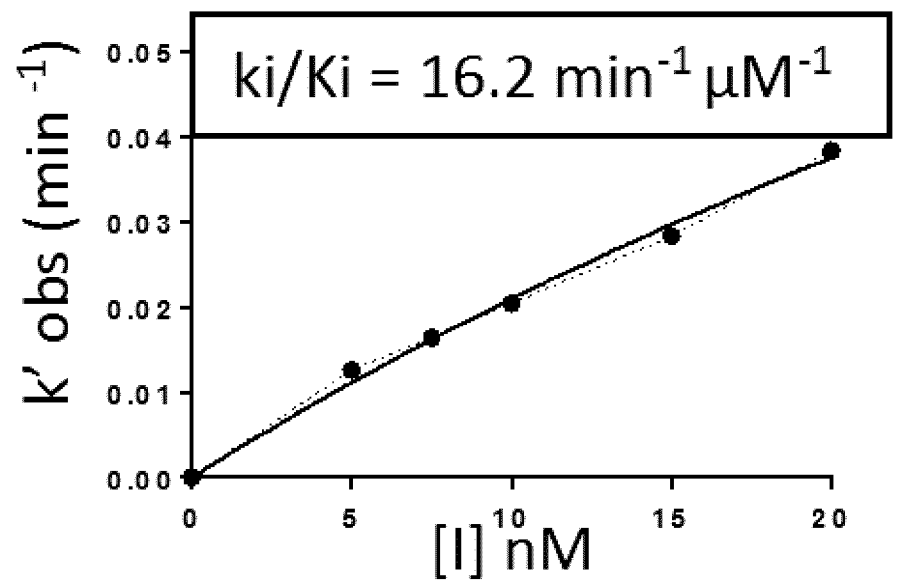
Figure 5:
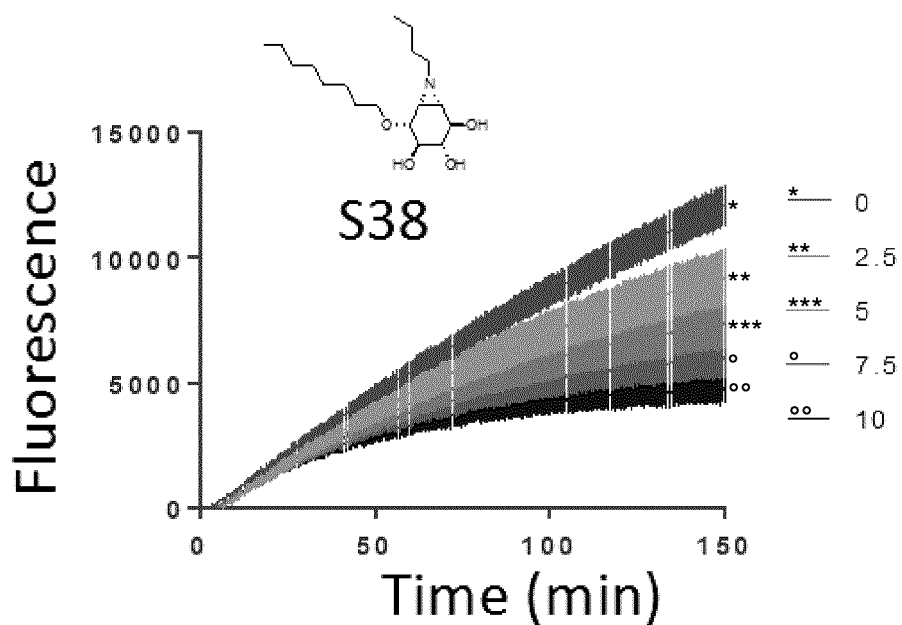
FIG. 5 shows a plot of the enzymatic turnover of 4-methylumbelliferyl β-D-glucopyranoside by β-glucocerebrosidase in the presence of conduritol aziridine derivative 38 (compound 2.11b) to determine $K_{obs}$ at various inhibitor concentrations vs time (top) and a corresponding secondary plot of $K_{obs}$ vs concentration of inhibitor for that compound (bottom).
Figure 5:
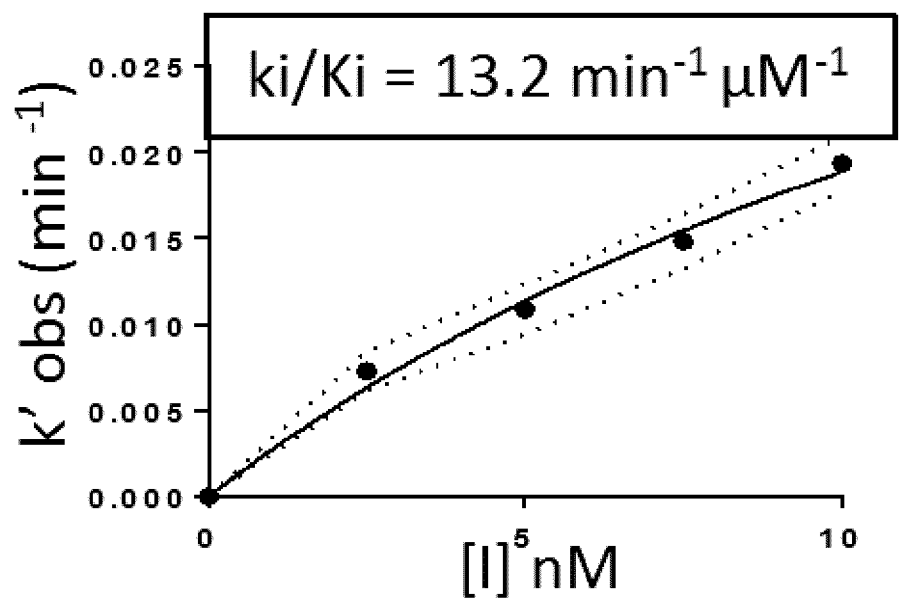
Figure 6:
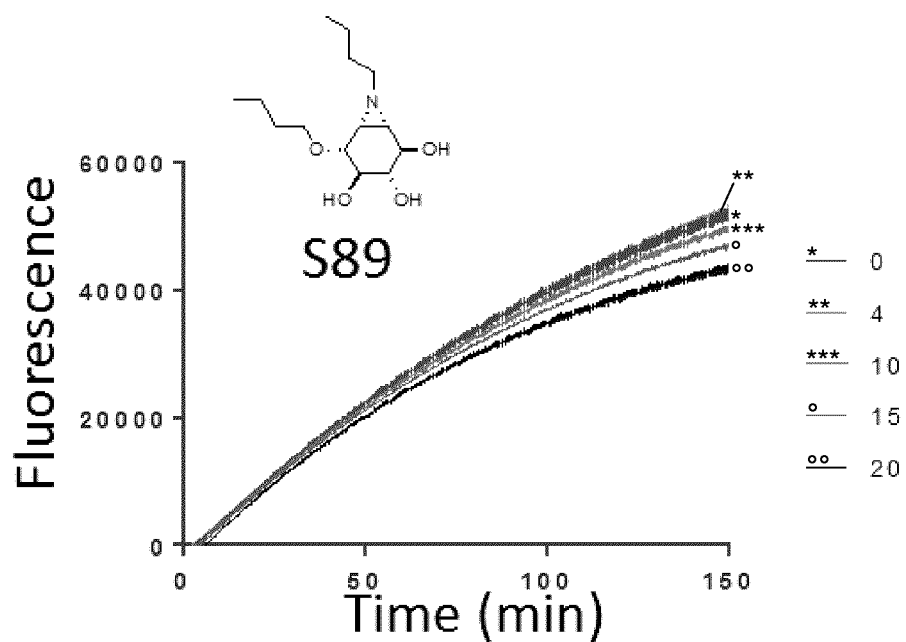
FIG. 6 shows a plot of the enzymatic turnover of 4-methylumbelliferyl β-D-glucopyranoside by β-glucocerebrosidase in the presence of conduritol aziridine derivative S89 to determine $K_{obs}$ at various inhibitor concentrations vs time (top) and a corresponding secondary plot of $K_{obs}$ vs concentration of inhibitor for that compound (bottom).
Figure 6:
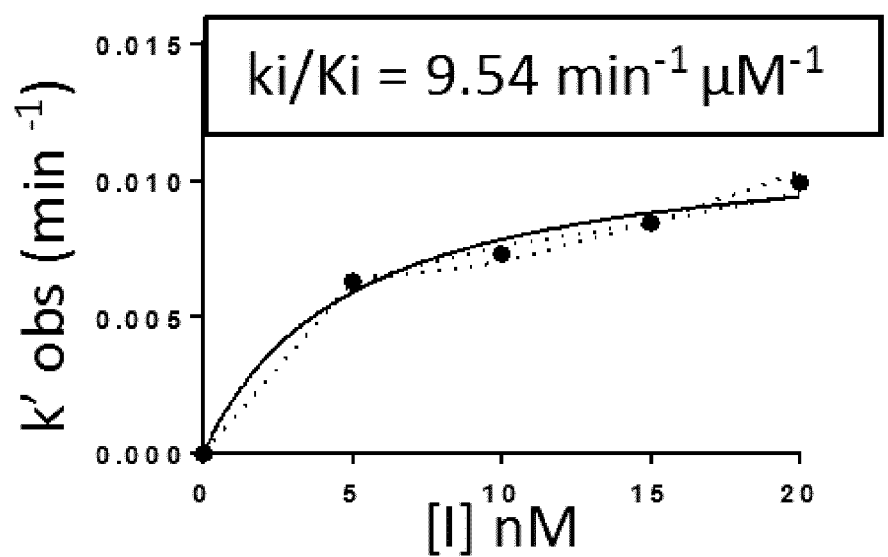
Figure 7:
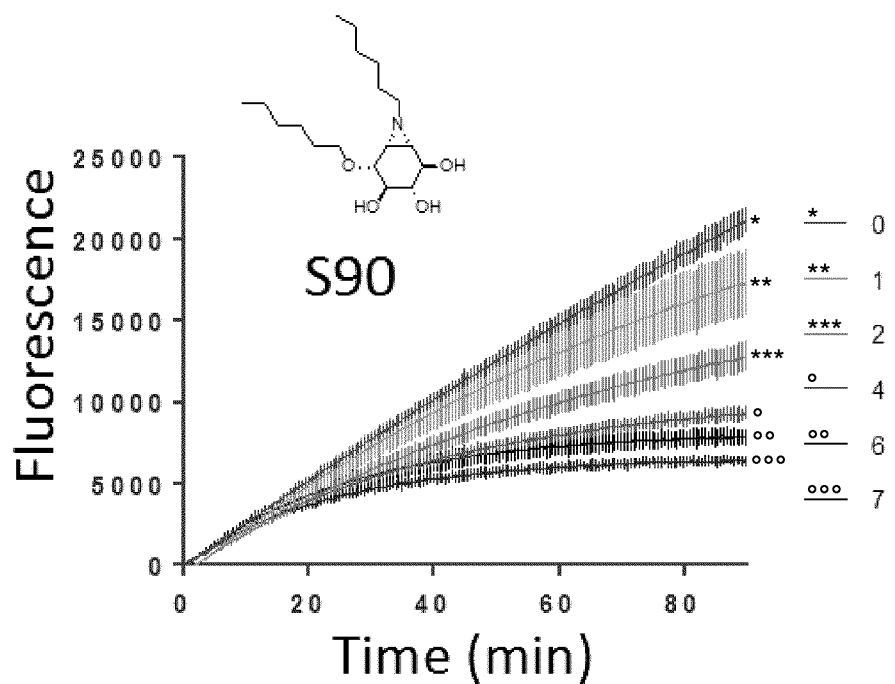
FIG. 7 shows a plot of the enzymatic turnover of 4-methylumbelliferyl β-D-glucopyranoside by β-glucocerebrosidase in the presence of conduritol aziridine derivative S90 to determine $K_{obs}$ at various inhibitor concentrations vs time (top) and a corresponding secondary plot of $K_{obs}$ vs concentration of inhibitor for that compound (bottom).
Figure 7:
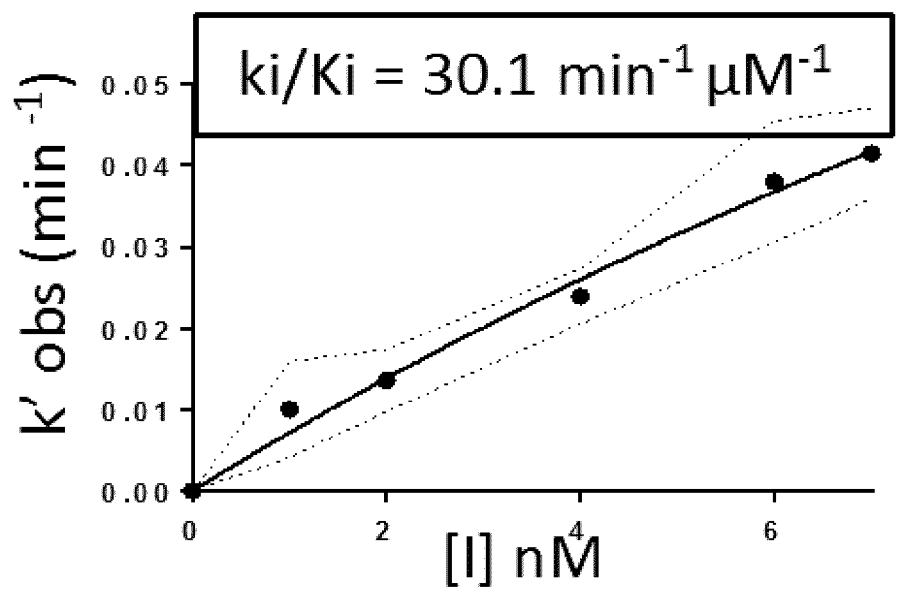
Figure 8:
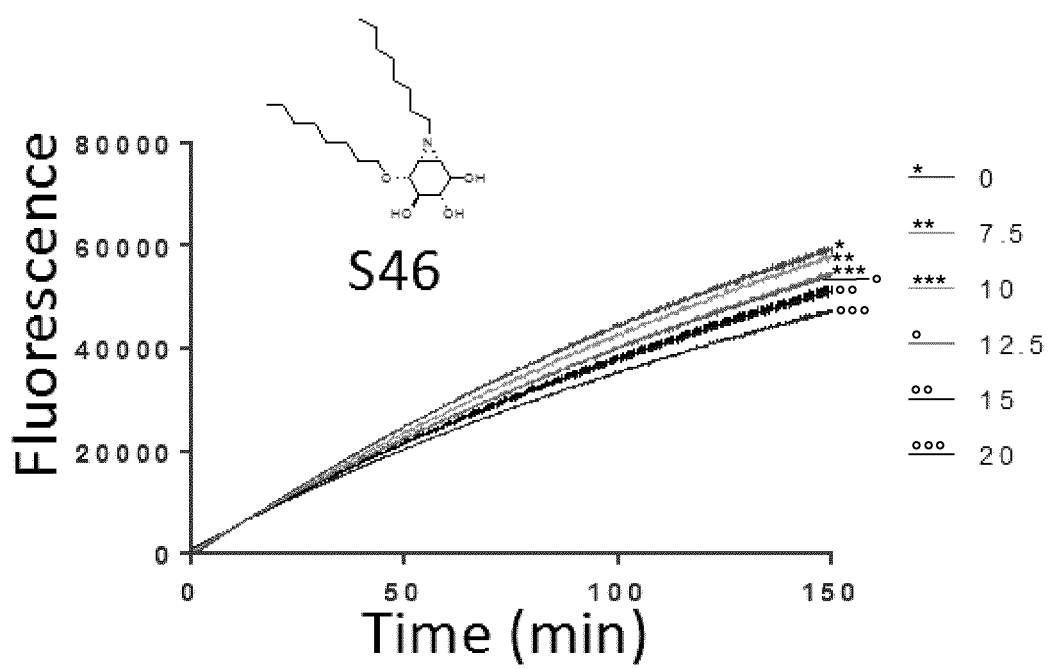
FIG. 8 shows a plot of the enzymatic turnover of 4-methylumbelliferyl β-D-glucopyranoside by β-glucocerebrosidase in the presence of conduritol aziridine derivative S46 (compound 2.11a) to determine $K_{obs}$ at various inhibitor concentrations vs time (top) and a corresponding secondary plot of $K_{obs}$ vs concentration of inhibitor for that compound (bottom).
Figure 8:
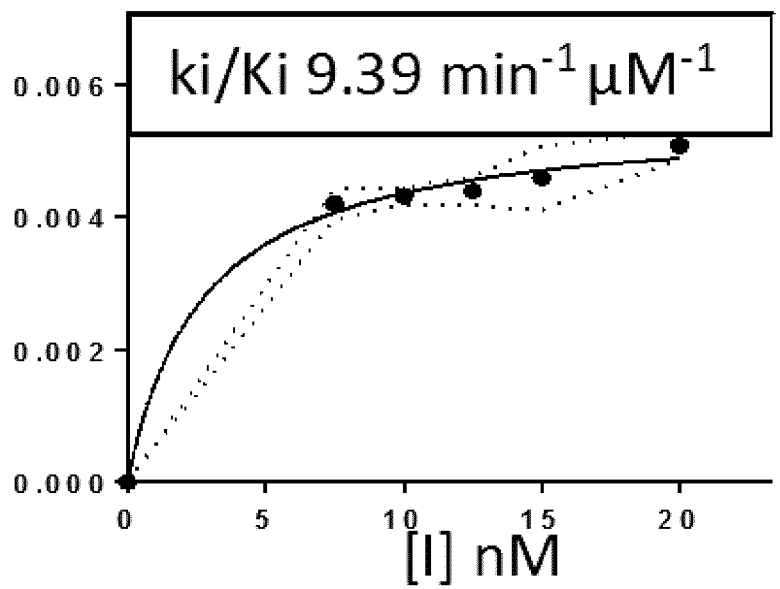

From examining the $k_i/K_i$ values obtained from the inactivation experiments it was clear that the binding affinity of 34 was similar to that of compound 1.7 (FIGS. 1-2). The $k_i/K_i$ values for 1.7 and 34 were found to be 4.70±0.25 μM$^{-1}$ min$^{-1}$ and 5100±100 mM$^{-1}$ min$^{-1}$ respectively. This demonstrates how potency was conserved upon installation of the fluorine or fluorinating handle. This kinetic information shows that fluorinated derivative 34 does not suffer from decreased binding affinity to GCase and radioactive derivatives have promise as PET imaging probes for imaging GCase in living organisms. For comparison, [$^{11}$C]-deprenyl is an irreversible inhibitor used to PET image monoamine oxidase B in the human brain. Since [$^{11}$C]-deprenyl was measured to inactivate monoamine oxidase B with a $k_i/K_i$ of 6400 mM$^{-1}$ min$^{-1}$,[69] this suggests that the fluorinated PET tracer candidate 34 has sufficient inactivation rates to be used as a PET tracer for imaging GCase in the brain of animals or humans.

Radioactive $^{18}$F derivatives of conduritol aziridines such as 34 used as PET probes may, for example, be useful molecular tools for elucidating the involvement of GCase in PD, aid in drug design for compounds that seek to increase GCase levels in PD and Gaucher disease and/or help unravel the molecular mechanisms of disease progression involving GCase.

Compound 2.11b was estimated to have a relative $k_i/K_i$ of 10 in comparison to 1.7, which made it one of the most potent inhibitors of GCase yet.

Example 4: Enzyme Kinetics of O-Alkylated-N-Substituted Aziridines

Compounds S88-S91 having the below structures were prepared by a similar method as described herein above for compounds 2.11a and 2.11b in Scheme 4 by employing alkyl iodides of varying chain length for the O-alkylation and N-alkylation steps:

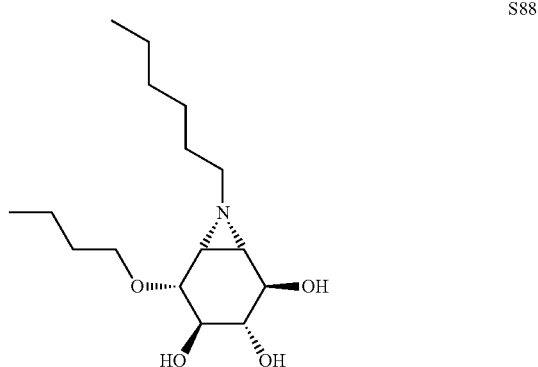

S88

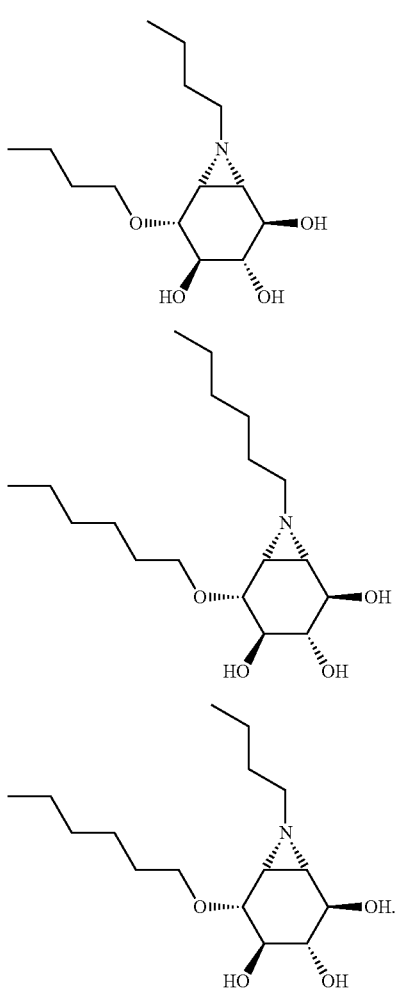

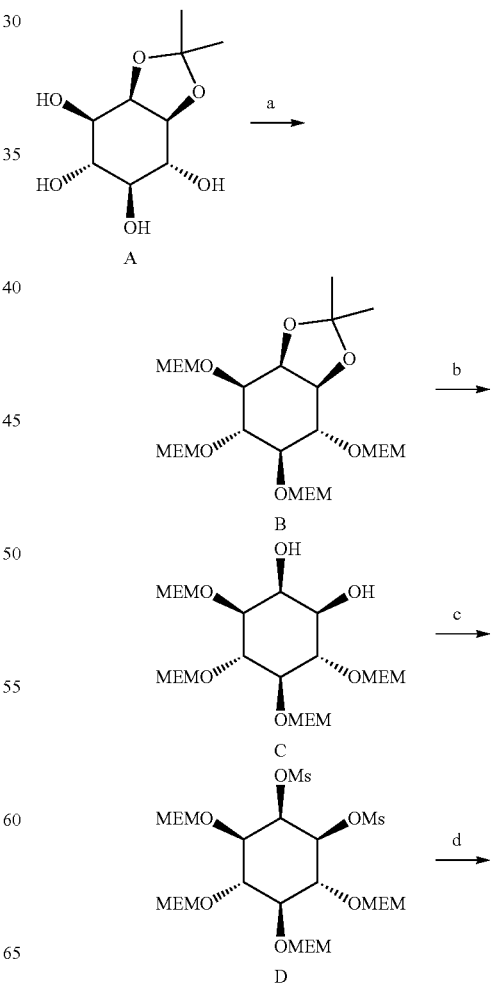

To assay the potency of the O-alkylated-N-substituted aziridines, continuous-release inhibition assays of GCase were carried out using the concentrations of aziridine at a temperature of 37° C. each corrected for photobleaching and spontaneous hydrolysis as shown in FIGS. 3-8 (top) for compounds S88, S91, S38 (compound 2.11b), S89, S90 and S46 (compound 2.11A) having the chemical structures shown in the inset to each plot. In the plots, data points represent the mean values, solid lines represent best fit according to Equation 2 (see Example 3, herein above) while dashed lines represent standard deviation. A secondary plot of $K_{obs}$ versus [ ] where data points represent the mean $K_{obs}$ values and error bars the standard deviation is also shown in FIGS. 3-8 (bottom). The solid line represents the best fit according to Equation 3 and the $k_i/K_i$ values of 19.4 min$^{-1}$ μM$^{-1}$ (S88), 16.2 min$^{-1}$ μM$^{-1}$ (S91), 13.2 min$^{-1}$ μM$^{-1}$ (S38), 9.54 min$^{-1}$ μM$^{-1}$ (S89), 30.1 min$^{-1}$ μM$^{-1}$ (S90) and 9.39 min$^{-1}$ μM$^{-1}$ (S46) were calculated using Equation 4.

The kinetic studies have revealed that the O-alkylated-N-substituted aziridines have high potency towards GCase, exceeding the $k_i/K_i$ values of existing inactivators of GCase and existing PET radiotracers that are irreversible inhibitors capable of imaging activity of enzymes from other enzyme families. In addition, preliminary enzyme kinetic studies using recombinant GBA2 and GBA3 have demonstrated that the dialkylated compounds are more potent towards GCase over GBA2 and GBA3. While not wishing to be limited by theory, this finding is in line with the fact that crystal structures of recombinant GBA2 revealed that important hydrogen bonds are formed between active site amino acids and the exocyclic C-6 hydroxyl group of glucose analogs (See: Charoenwattanasatien et al., "Bacterial β-Glucosidase Reveals the Structural and Functional Basis of Genetic Defects in Human Glucocerebrosidase 2 (GBA2)" *ACS Chem. Biol.*, 2016, 11 (7), pp 1891-1900 doi: 10.1021/acschembio.6b00192). This may, for example, explain the low potency of conduritols like conduritol B-epoxide towards GBA2 (ref 47) and while not wishing to be limited by theory, would likely hold true with conduritol aziridines since both classes of compounds lack the exocyclic C-6 hydroxyl group. This suggests that the present compounds could selectively inactivate GCase in cells and animals and that $^{18}$F-labeled O-alkylated-N-substituted aziridines would generate PET radiotracers selective to GCase over GBA2 and GBA3.

Example 5: Synthesis of Pyridine-Substituted Aziridine

An example of an aziridine having a pyridine substituent connected to the nitrogen was prepared via the following synthetic route:

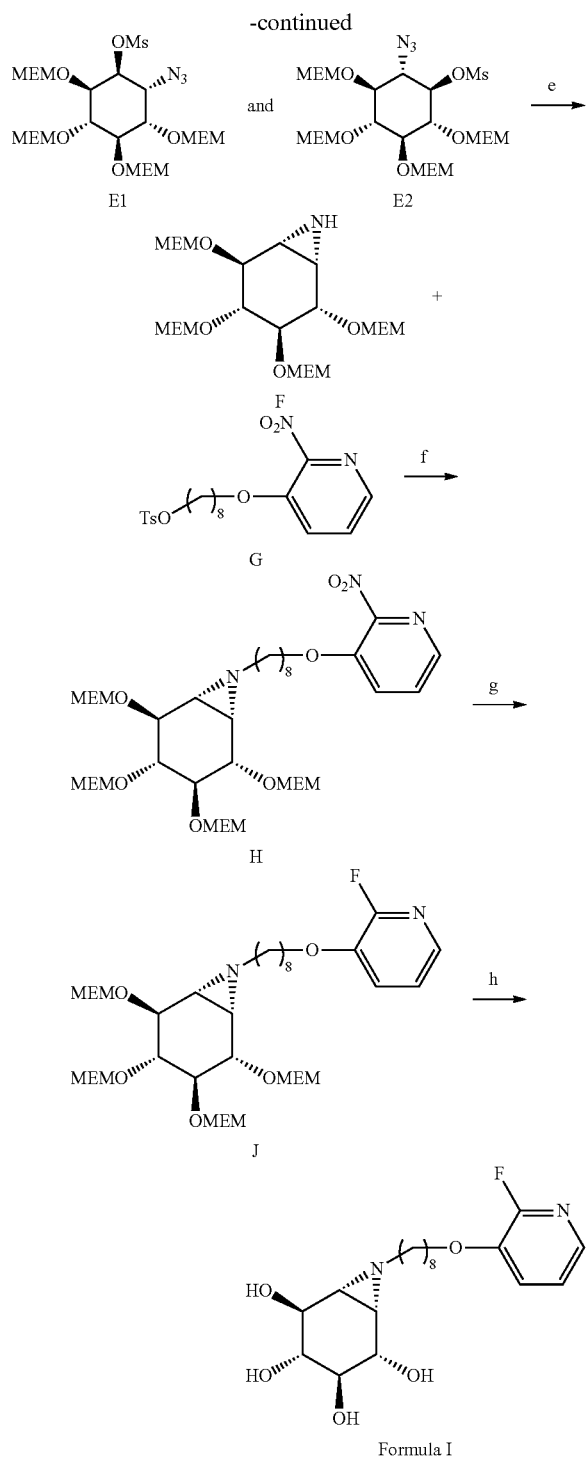

Reagents and conditions: (a) anhydrous DMF, MEMCl, DIPEA, 50° C., overnight, 79%; (b) 80% acetic acid, 50° C., 4 h, 63%; (c) MsCl, anhydrous pyridine, RT; (d) NaN₃, anhydrous DMF, 90° C., overnight; (e) PPh₃, water, acetonitrile, TEA, 75° C., overnight, 32%; (f) anhydrous acetonitrile, Na₂CO₃, 70° C., 68%; (g) KF/Kytofix®, DMSO, 160° C., 5 h, 71%; (h) TFA/DCM (1:1), RT, overnight, compound of Formula I: 70% chemical yield. Further details on the syntheses and characterization of the compounds in this scheme were as follows:

Compound B: To compound A (6.6 g, 30 mmol) and DIPEA (37.2 ml, 210 mmol) in 100 ml of anhydrous DMF, MEMCl (20.6 ml, 180 mmol) was dropped into the reaction solution slowly at 0° C. The mixture was allowed to increase to 65° C. overnight, and then cooled down to RT, whereupon 250 ml NaHCO₃ saturated solution was added to quench the reaction. The mixture was extracted with ×3 times 250 ml ethyl acetate, washed with NaCl saturated solution, dried over anhydrous Na₂SO₄, filtered and the resulting solution was concentrated under high vacuum. The residue was purified by silica gel column (hexane:ethyl acetate=1:1 to ethyl acetate) to yield the desired product 13.6 g, 23.8 mmol 79% as a light yellow oil. ¹H NMR (CDCl₃) δ 1.34 (s, 3H), 1.53 (s, 3H), 3.37 (d, J=2, 12H), 3.37-3.93 (m, 20H), 4.08 (t, J=5, 1H), 4.45 (dd, J=5, 1H), 4.86-4.92 (m, 8H).

Compound C: 100 ml, 80% acetic acid was added to compound B (13.6 g, 23.8 mmol), then the temperature increased to 50° C. for 4 h. The acetic acid was removed under high vacuum, and to the residue was added 500 ml ethyl acetate, then the mixture washed with saturated NaHCO₃ solution, separated, concentrated under vacuum, purified by silica gel column (EA to EA:methanol=20:1) to yield the desired product: 8 g, 15 mmol, 63% as a light yellow oil. ¹H NMR (CDCl₃) δ 3.36-3.38 (m, 12H), 3.42-3.96 (m, 20H), 4.25 (t, J=5, 1H), 4.31 (s, 1H), 4.82-4.93 (m, 8H).

Compound D: Compound C was dissolved in 50 ml anhydrous pyridine, MsCl (6.97 ml, 90 mmol) was dropped into the solution at 0° C., and after 1 h the temperature was allowed to increase to RT and continue to stir overnight. Then 500 ml ethyl acetate was added to the reaction solution, and the mixture washed with 0.1N citric acid solution and NaCl saturated solution, then separated, dried over anhydrous Na₂SO₄, filtered and the solvent removed under vacuum. The residue was purified by silica gel column (EA:Methanol=20:1) to yield the desired product: 9.4 g, 13.7 mmol, 91% as a light-yellow oil. ¹H NMR (CDCl₃) δ 3.19 (d, j=2.5, 6H), 3.39-3.40 (m, 12H), 3.50-3.97 (m, 20H), 4.52 (dd, J=5, 1H), 4.82-4.98 (m, 8H), 5.27 (s, 1H).

Compound E: To compound D (9.4 g, 13.67 mmol) in 60 ml of anhydrous DMF was added NaN₃ (889 mg, 13.67 mmol), and the mixture refluxed at 90° C. for 24 h. The reaction solution was cooled down to room temperature, 500 ml water was added, extracted with 500 ml×3 times ethyl acetate, separated, dried over anhydrous Na₂SO₄, filtered and concentrated under high vacuum, the residue was passed through a silica gel pad, and the solvents removed to yield 8.1 g of a mixture compounds E1 and E2 which were used in the subsequent step of the reaction scheme without purification.

Compound F: To a mixture of 8.1 g of compounds E1 and E2 in THF (100 ml) was added PPh₃ (3.34 g, 12.76 mmol) and TEA (25.51 mmol, 3.56 ml), the mixture was stirred 30 min at room temperature, then was added 10 ml water, and the temperature increased to 70° C. overnight. The solvent was removed under vacuum, the residue was purified by silica chromatography (EA to EA:methanol:NH₄OH=100:10:1) to yield the desired product 2.3 g, 32% as a light yellow oil. ¹H NMR (CDCl₃) δ 2.46 (s, 1H), 2.68 (s, 1H), 3.37 (t, J=5, 12H), 3.39-3.84 (m, 20H), 4.83-4.92 (m, 8H).

Compound H: To compound F (1 mmol, 513 mg) and compound G (1.1 eq, 1.1 mmol, 464.4 mg) in 30 ml anhydrous acetonitrile was added Na₂CO₃ (3 mmol, 318 mg), and the mixture stirred for 48 h at 70° C., then the solvent removed under high vacuum, and the residue was purified with a silica gel column (EA to EA:methanol=10:1) to yield the desired product: 526 mg, 0.58 mmol, 68% as a yellow oil. $^1$H NMR (CDCl$_3$) δ 1.34 (s, 6H), 1.44-1.48 (m, 2H), 1.55-1.59 (m, 2H), 1.69-1.73 (m, 1H), 1.81-1.87 (m, 2H), 1.95-2.01 (m, 2H), 2.51-2.54 (m, 1H), 3.52-3.59 (m, 8H), 3.67-3.89 (m, 10H), 4.13 (t, J=5, 2H), 4.83-4.91 (m, 8H), 7.52-7.53 (m, 2H), 8.07 (dd, J=2, 1H).

Compound J: Compound H (160 mg, 0.21 mmol) was dissolved in 1.5 ml anhydrous DMSO, then was added KF (2 eq, 0.42 mmol, 24 mg) and Kytofix®222 (1.2 eq, 0.25 mmol, 94 mg), then the reaction temperature increased to 160° C. for 5 h. The solvent was then removed under high vacuum, and the residue was purified with a silica column (EA to EA:methanol=10:1) to yield the desired product: 110 mg, 0.14 mmol, 71% chemical yield. $^1$H NMR (CDCl$_3$) δ 1.34 (s, 6H), 1.46-1.50 (t, J=2.5, 2H), 1.57 (s, 2H), 1.77 (s, 3H), 1.83-1.86 (m, 2H), 2.01 (s, 2H), 2.53 (s, 1H), 3.38-3.40 (m, 12H), 3.55-3.87 (m, 18H), 4.04 (t, J=6.5, 2H), 4.84-4.91 (m, 8H), 7.12 (dd, J=5, 1H), 7.73-7.75 (m, 1H).

Exemplary compound of Formula I: Compound J (60 mg, 0.08 mmol) was dissolved in 1 ml of TFA:DCM (1:1) solution, the reaction solution stirred for 48 h at RT, then dropped into saturated NaHCO$_3$ solution, the solvents removed under high vacuum, and the residue was purified with a silica gel column (EA:methanol=10:1.5) to yield the desired product; 22 mg, 0.057 mmol as a colourless oil with a 70% chemical yield. $^1$H NMR (MD$_3$OD) δ 1.38 (s, 6H), 1.50 (s, 2H), 1.60 (s, 2H), 1.69 (d, J=5, 1H), 1.81-1.84 (m, 2H), 1.96-1.98 (m, 1H), 2.15-2.21 (m, 1H), 2.37-2.42 (m, 2H), 3.10-3.14 (m, 1H), 3.23-3.29 (m, 1H), 3.65-3.69 (m, 1H), 4.08-4.12 (m, 2H), 7.24 (dd, J=5, 1H), 7.53-7.57 (m, 1H), 7.67-7.68 (m, 1H).

While the present application has been described with reference to what are presently considered to be the preferred examples, it is to be understood that the application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE DESCRIPTION

[1] Lombard, V., Golaconda Ramulu, H., Drula, E., Coutinho, P. M., Henrissat, B. The carbohydrate-active enzymes database (CAZy) in 2013. *Nucleic Acids Res.* 2014, 42, D490.

[2] Horowitz, M., Wilder, S., Horowitz, Z., Reiner, O., Gelbart, T., Beutler, E. The human glucocerebrosidase gene and pseudogene: structure and evolution. *Genomics*, 1989, 4: 87-96.

[3] Reczek, D., Schwake, M., Schroder, J., Hughes, H., Blanz, J., Jin, X., Brondyk, W., Van Patten, S., Edmunds, T. and Saftig, P. LIMP-2 is a receptor for lysosomal mannose-6-phosphate-independent targeting of beta-glucocerebrosidase. *Cell*, 2007, 131, 770-83.

[4] Siebert, M., Sidransky, E. and Westbroek, W. Glucocerebrosidase is shaking up the synucleinopathies. *Brain.* 2014, 137, 1304-1322.

[5] Jiang, J., Artola, M., Beenakker T. J. M., Schröder, S. P., Petracca, R., de Boer, C., Aerts, J. M., van der Marel, G. A., Codée, J. D. and Overkleeft. H. S. The Synthesis of Cyclophellitol-Aziridine and Its Configurational and Functional Isomers. *Eur. J. Org. Chem.* 2016, 3671-3678.

[6] (a) Soreghan, B., Thomas, S. N., Yang, A. J. Aberrant sphingomyelin/ceramide metabolic-induced neuronal endosomal/lysosomal dysfunction: potential pathological consequences in age-related neurodegeneration. *Adv. Drug Deliv. Rev.,* 2003, 55, 1515-24. (b) Jana, A., Hogan, E. L., Pahan, K. Ceramide and neurodegeneration: susceptibility of neurons and oligodendrocytes to cell damage and death. *J. Neurol. Sci.,* 2009, 278, 5-15. (c) Fortin, D. L., Troyer, M. D., Nakamura, K., Kubo, S., Anthony, M. D., Edwards, R. H. Lipid rafts mediate the synaptic localization of alpha-synuclein. *J. Neurosci.* 2004, 24, 6715-23.

[7] Kitatani, K., Idkowiak-Baldys, J., and Hannun, Y. A. The sphingolipid salvage pathway in ceramide metabolism and signaling. *Cell Signal,* 2008, 20, 1010-8.

[8] Gillard, B. K., Clement, R. G., Marcus, D. M. Variations among cell lines in the synthesis of sphingolipids in de novo and recycling pathways. *Glycobiology,* 1998, 8, 885-90. (b) Tettamanti, G., Bassi, R., Viani, P., Riboni, L. Salvage pathways in glycosphingolipid metabolism. *Biochimie.* 2003, 85, 423-37.

[9] (a) Rosenbloom, B., Balwani, M., Bronstein, J. M., Kolodny, E., Sathe, S., Gwosdow, A. R., Taylor, J. S., Cole, J. A., Zimran, A. and Weinreb, N. J. The incidence of Parkinsonism in patients with type 1 Gaucher disease: Data from the ICGG Gaucher Registry. *Blood Cell. Mol. Dis.* 2011, 46, 95-102. (b) Neumann, J., Bras, J., Deas, E., O'Sullivan, S. S., Parkkinen, L., Lachmann, R. H., Li A, Holton, J., Guerreiro, R., Paudel, R., Segarane, B., Singleton, A., Lees, A., Hardy, J., Houlden, H., Revesz, T. and Wood, N. W. Glucocerebrosidase mutations in clinical and pathologically proven Parkinson's disease. *Brain,* 2009, 132, 1783-94. (c) Sidransky, E., Nalls, M. A., Aasly, J. O., Aharon-Peretz, J., Annesi, G., Barbosa, E. R., Bar-Shira, A., Berg, D., Bras, J., Brice, A., Chen, C. M., Clark, L. N., Condroyer, C. De Marco, E. V. et al. Multicenter analysis of glucocerebrosidase mutations in Parkinson's disease. *N. Engl. J. Med.* 2009, 361, 1651-61. (d) Lwin, A., Orvisky, E., Goker-Alpan, O., LaMarca, M. E. and Sidransky, E. Glucocerebrosidase mutations in subjects with parkinsonism. *Mol. Genet. Metab.* 2004, 81, 70-73. (e) Goker-Alpan, O., Stubblefield, B. K., Giasson, B. I. and Sidransky, E. Glucocerebrosidase is present in α-synuclein inclusions in Lewy body disorders. *Acta Neuropathol.* 2010, 120, 641-649.

[10] Grabowski, G. A., Lysosomal storage disease 1-Phenotype, diagnosis, and treatment of Gaucher's disease. *Lancet,* 2008, 372 (9645), 1263-1271.

[11] Beutler, E. and Grabowski, G. A. (2001) Gaucher Disease. In: The Metabolic and Molecular Bases of Inherited Disease, Vol. II (ed. by C. R. Scriver, W. S. Sly, B. Childs, A. L. Beaudet, D. Valle, K. W. Kinzler & B. Vogelstein), pp. 3635-3668. McGraw-Hill Inc., Columbus, USA.

[12] Tamargo, R. J., Velayati, A., Goldin, E., and Sidransky, E. The role of saposin C in Gaucher disease. *Mol. Genet. Metab.* 2012, 106(3), 257-263.

[13] Jmoudiak, M. and Futerman A. H. Gaucher disease: pathological mechanisms and modem management. *Brit. J. Haematol.* 2005, 129, 178-188.

[14] Zimran, A. (ed.) (1997) Gaucher's Disease. Balliere Tindall, Cambridge, UK.

[15] Goker-Alpan, O., Schiffmann, R., Park, J. K., Stubblefield, B. K., Tayebi, N. and Sidransky, E. Phenotypic continuum in neuronopathic Gaucher disease: an intermediate phenotype between type 2 and type 3. *Journal of Pediatrics,* 2003, 143, 273-276.

[16] Weinreb, N. J., Charrow, J., Andersson, H. C., Kaplan, P., Kolodny, E. H., Mistry, P., Pastores, G., Rosenbloom, B. E., Scott, C. R., Wappner, R. S. & Zimran, A. Effectiveness of enzyme replacement therapy in 1028 patients with type 1 Gaucher disease after 2 to 5 years of treatment: a report from the Gaucher Registry. *American Journal of Medicine,* 2002, 113, 112-119.

[17] (a) Dvir, H., Harel, M., McCarthy, A. A., Toker, L., Silman, I., Futerman, A. H. and Sussman, J. L. X-ray structure of human acid-betaglucosidase, the defective enzyme in Gaucher disease. *EMBO Reports,* 2003, 4, 704-709. (b) Desnick, R. J. Enzyme replacement and enhancement therapies for lysosomal diseases. *Journal of Inherited Metabolic Disease,* 2004, 27, 385-410. (c) Fan, J. Q. A contradictory treatment for lysosomal storage disorders: inhibitors enhance mutant enzyme activity. *Trends in Pharmacological Science,* 2003, 24, 355-360.

[18] Bultron, G. et al. The risk of Parkinson's disease in type 1 Gaucher disease. *J Inherit Metab Dis* 33, 167-173, doi:10.1007/s0545-010-9055-0 (2010).

[19] Hoehn, M. M. and Yahr, M. D. Parkinsonism: onset, progression and mortality. *Neurology,* 1967, 17, 427-442.

[20] Kotzbauer, P. T., Tu, Z. and Mach, R. H. Current status of the development of PET radiotracers for imaging alpha synuclein aggregates in Lewy bodies and Lewy neurites. *Clin. Transl. Imaging,* 2017, 5:3-14.

[21] (a) Cullen, V. et al. Acid beta-glucosidase mutants linked to Gaucher disease, Parkinson disease, and Lewy body dementia alter alpha-synuclein processing. *Ann Neurol* 69, 940-953, doi:10.1002/ana.22400 (2011). (b) Manning-Bog, A. B., Schule, B. & Langston, J. W. Alpha-synuclein-glucocerebrosidase interactions in pharmacological Gaucher models: a biological link between Gaucher disease and parkinsonism. *Neurotoxicology* 30, 1127-1132, doi:10.1016/j.neuro.2009.06.009 (2009). (c) Sardi, S. P. et al. CNS expression of glucocerebrosidase corrects alpha-synuclein pathology and memory in a mouse model of Gaucher-related synucleinopathy. *Proc Natl Acad Sci USA* 108, 12101-12106, doi:10.1073/pnas.1108197108 (2011). (d) Xu, Y. H. et al. Accumulation and distribution of alpha-synuclein and ubiquitin in the CNS of Gaucher disease mouse models. *Mol Genet Metab* 102, 436-447, doi:10.1016/j.ymgme.2010.12.014 (2011). (e) Yap, T. L. et al. Alpha-synuclein interacts with Glucocerebrosidase providing a molecular link between Parkinson and Gaucher diseases. *J Biol Chem* 286, 28080-28088, doi:10.1074/jbc.M111.237859 (2011).

[22] Spillantini, M. G., Crowther, R. A., Jakes, R., Hasegawa, M. and Goedert, M. (1998) alpha-Synuclein in filamentous inclusions of Lewy bodies from Parkinson's disease and dementia with lewy bodies. *Proc. Natl. Acad. Sci. USA,* 1998, 95(11):6469-6473.

[23] Bahr, B. A. and Bendiske, J. The neuropathogenic contributions of lysosomal dysfunction. *J. Neurochem.* 2002, 83, 481-489.

[24] Olanow, C. W, Hauser, R. A., Gauger, L., Malapira, T., Koller, W., Hubble, J., Bushenbark, K., Lilienfeld, D. and Esterlitz, J. The effect of deprenyl and levodopa on the progression of Parkinson's disease. *Ann. Neurol.,* 1995, 38, 771-7.

[25] Fahn, S., Oakes, D., Shoulson, I., et al. Levodopa and the progression of Parkinson's disease. New *Engl. J. Med.* 2004, 351(24), 2498-2508.

[26] Tveiten, O. V., Skeie, G. O., Haugarvoll, K., Muller, B., Larsen, J. P. and Tysnes, O. B. Treatment in early Parkinson's disease: the Norwegian Park West study. *Acta. Neurol. Scand.* 2013, 128, 107-113.

[27] Hughes, A. J., Ben-Shlomo, Y., Daniel, S. E. and Lees, A. J. What features improve the accuracy of clinical diagnosis in Parkinson's disease: a clinicopathologic study. *Neurology,* 1992, 42(6), 1142-1146.

[28] (a) Marsden, C. D. Parkinson's disease. *Lancet.* 1990, 335, 948-952. (b) Ross, G. W., Petrovitch, H., Abbott, R. D., Nelson, J., Markesbery, W., Davis, D., Hardman, J., Launer, L., Masaki, K., Tanner, C. M. and White, L. R. Parkinsonian signs and substantia nigra neuron density in decedents elders without PD. *Ann. Neurol.* 2004, 56, 532-539.

[29] Skovronsky, D. M., Lee, V. M. and Trojanowski, J. Q. Neurodegenerative diseases: new concepts of pathogenesis and their therapeutic implications. *Annu. Rev. Pathol.* 2006, 1151-170.

[30] Booth, T. C., Nathan, M., Waldman, A. D., Quigley, A. M., Schapira, A. H., and Buscombe, J. The Role of Functional Dopamine-Transporter SPECT Imaging in Parkinsonian Syndromes, Part 1, *AJNR Am J Neuroradiol,* 2015, 36, 229-35.

[31] Rosenbloom, B., Balwani, M., Bronstein, J. M., Kolodny, E., Sathe, S., Gwosdow, A. R., Taylor, J. S., Cole, J. A., Zimran, A. and Weinreb, N. J. The incidence of Parkinsonism in patients with type 1 Gaucher disease: Data from the ICGG Gaucher Registry. *Blood Cell. Mol. Dis.* 2011, 46, 95-102.

[32] (a) Neumann, J., Bras, J., Deas, E., O'Sullivan, S. S., Parkkinen, L., Lachmann, R. H., Li A, Holton, J., Guerreiro, R., Paudel, R., Segarane, B., Singleton, A., Lees, A., Hardy, J., Houlden, H., Revesz, T. and Wood, N. W. Glucocerebrosidase mutations in clinical and pathologically proven Parkinson's disease. *Brain,* 2009, 132, 1783-94. (b) Sidransky, E., Nalls, M. A., Aasly, J. O., Aharon-Peretz, J., Annesi, G., Barbosa, E. R., Bar-Shira, A., Berg, D., Bras, J., Brice, A., Chen, C. M., Clark, L. N., Condroyer, C. De Marco, E. V. et al. Multicenter analysis of glucocerebrosidase mutations in Parkinson's disease. *N. Engl. J. Med.* 2009, 361, 1651-61.

[33] Lwin, A., Orvisky, E., Goker-Alpan, O., LaMarca, M. E. and Sidransky, E. Glucocerebrosidase mutations in subjects with parkinsonism. *Mol. Genet. Metab.* 2004, 81, 70-73.

[34] Goker-Alpan, O., Stubblefield, B. K., Giasson, B. I. and Sidransky, E. Glucocerebrosidase is present in α-synuclein inclusions in Lewy body disorders. *Acta Neuropathol.* 2010, 120, 641-649.

[35] Clark, L. N., Kartsaklis, L. A., Wolf Gilbert, R., Dorado, B., Ross, B. M., Kisselev, S., Verbitsky, M., Mejia-Santana, H., Cote, L. J., Andrews, H., Vonsattel, J. P., Fahn, S., Mayeux, R., Honig, L. S., Marder, K. Association of glucocerebrosidase mutations with dementia with Lewy bodies. *Arch. Neurol.* 2009, 66(5), 578-583.

[36] Bae, E., Yang, N. A., Lee, C., Lee, H., Kim, S., Sardi, S. P. and Lee, S. Loss of glucocerebrosidase 1 activity causes lysosomal dysfunction and α-synuclein aggregation. *Exp. Mol. Med.* 2015, 47, 1-8.

[37] Gegg, M. E. et al. Glucocerebrosidase deficiency in substantia nigra of parkinson disease brains. *Ann Neurol* 72, 455-463, doi:10.1002/ana.23614 (2012).

[38] Sardia, S. P., Clarke, J., Viel, C., Chan, M., Tamsett, T. J., Treleaven, C. M., Bu, J., Sweet, L., Passini, M. A., Dodge, J. C., Yu, W. H., Sidman, R. L., Cheng, S. H. and Shihabuddin, L. S. Augmenting CNS glucocerebrosidase activity as a therapeutic strategy for parkinsonism and other Gaucher-related synucleinopathies. *PNAS.* 2013, 110, 3537-3542.

[39] Murphy, K. E., Gysbers, A. M., Abbott, S. K., Tayebi, N., Kim, W. S., Sidransky, E., Cooper, A., Garner, B. and Halliday, G. M. Reduced glucocerebrosidase is associated with increased α-synuclein in sporadic Parkinson's disease. *Brain.* 2014, 137, 834-848.

[40] Murphy, K. E. & Halliday, G. M. Glucocerebrosidase deficits in sporadic Parkinson disease. *Autophagy* 10, 1350-1351, doi:10.4161/auto.29074 (2014).

[41] Mazzulli, J. R., Xu, Y. H., Sun, Y., Knight, A. L., McLean, P. J., Caldwell, G. A., Sidransky, E., Grabowski, G. A. and Krainc, D. Gaucher disease glucocerebrosidase and alpha-synuclein form a bidirectional pathogenic loop in synucleinopathies. *Cell,* 2011, 146, 37-52.

[42] Walvoort, M. T. C., Kallemeijn, W. W., Willems, L. I., Witte, M. D., Aerts, J. M. F. G., van der Marel, G. A., Codée, J. D. and Overkleeft. H. S. Tuning the leaving group in 2-deoxy-2-fluoroglucoside results in improved activity-based retaining b-glucosidase probes. *Chem. Commun.,* 2012, 48, 10386-10388.

[43] Willems, L. I., Jiang, J., Li, K., Witte, M. D., Kallemeijn, W. W., Beenakker T. J. M., Schröder, S. P., Aerts, J. M., van der Marel, G. A., Codée, J. D. and Overkleeft. H. S. From Covalent Glycosidase Inhibitors to Activity-Based Glycosidase Probes. *Chem. Eur. J.* 2014, 20, 10864-10872.

[44] Adams, B. T., Niccoli, S., Chowdhury, M. A., Esarik, A. N., Lees, S. J., Rempel, B. P. and Phenix, C. P. N-Alkylated Conduritol Aziridines are Potent, Specific and Cell-permeable Covalent Inactivators of Human pi-Glucocerebrosidase. *Chem. Commun. (Camb).* 2015, 51(57), 11390-11393.

[45] (a) Withers, S. G., Street, I. P., Bird, P. and Dolphin, D. H. *J. Am. Chem. Soc.,* 1987, 109, 7530. (b) Withers, S. G., Rupitz, K. and Street, I. P. *J. Biol. Chem.,* 1988, 263, 7929.

[46] Phenix, C. P., Rempel, B. P., Colobong, K., Doudet, D. J., Adam, M. J., Clarke, L. A. and Withers, S. G. Imaging of enzyme replacement therapy using PET. *PNAS.* 2010, 107, 10842-10847.

[47] Ridley, C. M., Thur, K. E., Shanahan, J., Thillaiappan, N. B., Shen, A., Uhl, K., Walden, C. M., Rahim, A. A., Waddington, S. N., Platt, F. M. and van der Spoel, A. C. beta-Glucosidase 2 (GBA2) Activity and Imino Sugar Pharmacology. *J. Biol. Chem.* 2013, 288, 26052-26066.

[48] Premkumar, L., Sawkar, A. R, Boldin-Adamsky, S., Toker, L., Silman, I., Kelly, J. W., Futerman, A. H. and Sussman, J. L. X-ray Structure of Human Acid-β-Glucosidase Covalently Bound to Conduritol-B-Epoxide IMPLICATIONS FOR GAUCHER DISEASE. *J. Biol. Chem.* 2005, 280 (25), 23815-23819.

[49] (a) Walvoort, M. T. C., Kallemeijn, W. W., Willems, L. I., Witte, M. D., Aerts, J. M. F. G., van der Marel, G. A., Codée, J. D. and Overkleeft. H. S. Tuning the leaving group in 2-deoxy-2-fluoroglucoside results in improved activity-based retaining b-glucosidase probes. *Chem. Commun.,* 2012, 48, 10386-10388. (b) Li, K. Y., Jiang, J., Witte, M. D., Kallemeijn, W. W., Donker-Koopman, W. E., Boot, R. G., Aerts, J. M., Codée, J. D., van der Marel, G. A. and Overkleeft, H. S. Exploring functional cyclophellitol analogues as human retaining beta-glucosidase inhibitors. *Org. Biomol. Chem.,* 2014, 12, 7786. (c) Jiang J., Beenakker, T. J., Kallemeijn, W. W., van der Marel, G. A., van den Elst, H., Codée, J. D. Aerts, J. M. F. G., and Overkleeft. H. S. Comparing Cyclophellitol N-Alkyl and N-Acyl Cyclophellitol Aziridines as Activity-Based Glycosidase Probes. *Chem. Eur. J.* 2015, 21, 10861-10869. (d) Willems, L. I., Jiang, J., Li, K., Witte, M. D., Kallemeijn, W. W., Beenakker T. J. M., Schröder, S. P., Aerts, J. M., van der Marel, G. A., Codée, J. D. and Overkleeft. H. S. From Covalent Glycosidase Inhibitors to Activity-Based Glycosidase Probes. *Chem. Eur. J.* 2014, 20, 10864-10872. (e) Jiang, J., Artola, M., Beenakker T. J. M., Schröder, S. P., Petracca, R., de Boer, C., Aerts, J. M., van der Marel, G. A., Codée, J. D. and Overkleeft. H. S. The Synthesis of Cyclophellitol-Aziridine and Its Configurational and Functional Isomers. *Eur. J. Org. Chem.* 2016, 3671-3678.

[50] Kallemeijn, W. W., Li, K. Y., Witte, M. D., Marques, A. R., Aten, J., Scheij, S., Jiang, J., Willems, L. I., Voom-Brouwer, T. M., van Roomen, C. P., Ottenhoff, R., Boot, R. G., van den Elst, H., Walvoort, M. T., Florea, B. I., Codée, J. D., van der Marel, G. A., Aerts, J. M. and Overkleeft, H. S. Novel Activity-Based Probes for Broad-Spectrum Profiling of Retaining β-Exoglucosidases In Situ and In Vivo. *Angew. Chem-Ger Edit.* 2012, 51(50), 12529-12533.

[51] Caron, G.; Withers, S. G., CONDURITOL AZIRIDINE—A NEW MECHANISM-BASED GLUCOSIDASE INACTIVATOR. Biochemical and Biophysical Research Communications 1989, 163 (1), 495-499.

[52] Smith, M. W. and Gumbleton, M. Endocytosis at the blood-brain barrier: from basic understanding to drug delivery strategies. *J. Drug Target.* 2006, 14, 191-214.

[53] Agarwal, S., Jain, R., Pal, D., and Mitra, A. K. Functional Characterization Of Peptide Transporters In MDCKII—MDR1 Cell line As A Model For Oral Absorption Studies. *Int. J. Pharm.* 2007, 332(1-2), 147-152.

54 Kolter, T., Winau, F., Schaible, U. E., Leippe, M. & Sandhoff, K. Lipid-binding proteins in membrane digestion, antigen presentation, and antimicrobial defense. *J Biol Chem* 280, 41125-41128, doi:10.1074/jbc.R500015200(2005).

55 Premkumar, L., Sawkar, A. R, Boldin-Adamsky, S., Toker, L., Silman, I., Kelly, J. W., Futerman, A. H. and Sussman, J. L. X-ray Structure of Human Acid-β-Glucosidase Covalently Bound to Conduritol-B-Epoxide IMPLICATIONS FOR GAUCHER DISEASE. *J. Biol. Chem.* 2005, 280 (25), 23815-23819.

[56] Lee, C. M. & Farde, L. Using positron emission tomography to facilitate CNS drug development. *Trends Pharmacol Sci* 27, 310-316, doi:10.1016/j.tips.2006.04.004 (2006).

57 Fowler, J. S. et al. Monoamine oxidase: radiotracer development and human studies. *Methods* 27, 263-277 (2002).

[58] Koeppe, R. A. et al. Kinetic modeling of N-[11C]methylpiperidin-4-yl propionate: alternatives for analysis of an irreversible positron emission tomography trace for measurement of acetylcholinesterase activity in human brain. *J Cereb Blood Flow Metab* 19, 1150-1163, doi:10.1097/00004647-199910000-00012 (1999).

[59] (a) Hicks, J. W. et al. Synthesis and preclinical evaluation of [11C-carbonyl] PF-04457845 for neuroimaging of fatty acid amide hydrolase. *Nucl Med Biol* 40, 740-746, doi: 10.1016/j.nucmedbio.2013.04.008 (2013). (b) Shimoda, Y. et al. N-(3,4-Dimethylisoxazol-5-yl)piperazine-4-[4-(2-fluoro-4-[(11)C]methylphenyl)thia zol-2-yl]-1-carboxamide: A promising positron emission tomography ligand for fatty acid amide hydrolase. *Bioorg Med Chem* 24, 627-634, doi:10.1016/j.bmc.2015.12.026 (2016). (c) Wyffels, L. et al. PET imaging of fatty acid amide hydrolase in the brain: synthesis and biological evaluation of an $^{11}$C-labelled URB597 analogue. *Nucl Med Biol* 37, 665-675, doi:10.1016/j.nucmedbio.2010.03.009 (2010). (d) Wilson, A. A. et al. [11C]CURB: Evaluation of a novel radiotracer for imaging fatty acid amide hydrolase by positron emission tomography. *Nucl Med Biol* 38, 247-253, doi:10.1016/j.nucmedbio.2010.08.001 (2011). (e) Rotstein, B. H. et al. PET imaging of fatty acid amide hydrolase with [(18)F]DOPP in nonhuman primates. *Mol Pharm* 11, 3832-3838, doi:10.1021/mp500316 h (2014).

[60] (a) Wang, C., Placzek, M. S., Van de Bittner, G. C., Schroeder, F. A. & Hooker, J. M. A Novel Radiotracer for Imaging Monoacylglycerol Lipase in the Brain Using Positron Emission Tomography. *ACS Chem Neurosci* 7, 484-489, doi:10.1021/acschemneuro.5b00293 (2016). (b) Wang, L. et al. Synthesis and Preclinical Evaluation of Sulfonamido-based [(11)C-Carbonyl]-Carbamates and Ureas for Imaging Monoacylglycerol Lipase. *Theranostics* 6, 1145-1159, doi:10.7150/thno.15257 (2016).

[61] Fowler, J. S. et al. Monoamine oxidase: radiotracer chemistry and human studies. *J Labelled Comp Radiopharm* 58, 51-64, doi:10.1002/jlcr.3247 (2015).

[62] Rotstein, B. H.; Stephenson, N. A.; Vasdev, N.; Liang, S. H. Spirocyclic hypervalent iodine(III)-mediated radiofluorination of non-activated and hindered aromatics. *Nature Communications* 2014, 5, 4365.

[63] See, for example: Nielsen, M. K.; Ugaz, C. R.; Li, W.; Doyle, A. G. PyFluor: A Low-Cost, Stable, and Selective Deoxyfluorination Reagent. *J. Am. Chem. Soc.* 2015, 137, 9571-9574.

[64] Huang, B., Law, M. W. and Khong, P. L. Whole-Body PET/CT Scanning: Estimation of Radiation Dose and Cancer Risk. *Radiology*, 2009, 251(1).

[65] Way, J. D., and Wuest, F. Automated radiosynthesis of no-carrier-added 4 [18F]fluoroiodobenzene: a versatile building block in 18F radiochemistry. *J. Label Compd. Radiopharm.*, 2014, 57, 104-109.

[66] Oldendorf, W. H. Brain uptake of radiolabeled amino acids, amines, and hexoses after arterial injection. *Am J Physiol* 221, 1629-1639 (1971).

[67] Yadav, A. K. et al. Fluorescence-quenched substrates for live cell imaging of human glucocerebrosidase activity. *J Am Chem Soc* 137, 1181-1189, doi:10.1021/ja5106738 (2015).

[68] (a) Briggs G E, H. J., A Note on the Kinetics of Enzyme Action. *Biochemical Journal* 1925, 19 (2), 338-339; (b) Michaelis L, M. M., Die Kinetik der Invertinwirkung. *Biochemische Zeitschrift* 1913, 49, 333-369; (c) Johnson, K. A.; Goody, R. S., The Original Michaelis Constant: Translation of the 1913 Michaelis-Menten Paper. *Biochemistry* 2011, 50 (39), 8264-8269.

[69] Fowler, J. S., MacGregor, R. R., Wolf, A. P., Arnett, C. D., Dewey, S. L., Schlyer, D., Christman, D., Logan, J., Smith, M., Sachs, H. Aquilonius, S. M., Bjurling, P., Halldin, C., Hartvig, P., Leenders, K. L., Lundqvist, H., Oreland, L., Stalnacke, C. G., Langstrom, B. Mapping Human-Brain Monoamine Oxidase-A and Oxidase-B With C-11 Labeled Suicide Inactivators and PET. *Science* 1987, 235, 481-485.

TABLE 1

Kinetic data on compounds of Scheme 1 for inhibition of GCase.

| Compound | IC$_{50}$(μM) | Ki(μM) | ki(min$^{-1}$) | k$_i$/K$_i$(μM$^{-1}$/min$^{-1}$) |
|---|---|---|---|---|
| 1.1 | >1000 | — | — | 12.00 |
| 1.2 | 9.49 | 140 | 0.590 | 4.20 × 10$^{-4}$ |
| 1.3 | — | 0.152 | 0.078 | 0.514 |

TABLE 1-continued

Kinetic data on compounds of Scheme 1 for inhibition of GCase.

| Compound | IC$_{50}$(μM) | Ki(μM) | ki(min$^{-1}$) | k$_i$/K$_i$(μM$^{-1}$/min$^{-1}$) |
|---|---|---|---|---|
| 1.5 | — | 2.40 | 0.140 | 0.058 |
| 1.6 | — | 0.050 | 0.140 | 2.80 |
| 1.7 | — | 0.005 | 0.120 | 25.0 |

The invention claimed is:

1. A compound of Formula I(b):

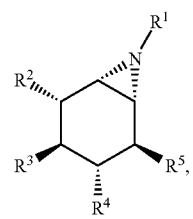

I(b)

wherein
R$^2$ is —OC$_{4-10}$alkyl;
R$^3$, R$^4$ and R$^5$ are each —OH;
R$^1$ is a group selected from:
—(CH$_2$)$_x$CH$_2$X,
—(CH$_2$)$_y$CHX(CH$_2$)$_z$CH$_3$,

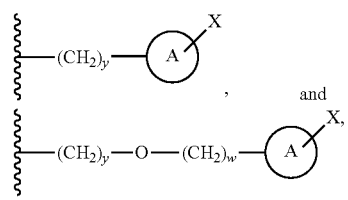

x is an integer between 1 and 20;
y is an integer between 1 and 10;
z is an integer between 1 and 10;
w is an integer between 0 and 10;

is phenyl or pyridyl;
X is H or F; and
F is $^{19}$F or [18]F.

2. The compound of claim 1, wherein X is F and R$^1$ is a group selected from:
—(CH$_2$)$_x$CH$_2$F,
—(CH$_2$)$_y$CHF(CH$_2$)$_z$CH$_3$,

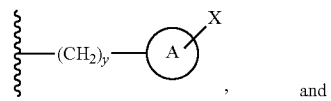

and

-continued

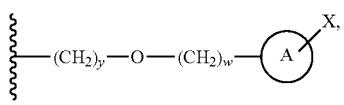

3. The compound of claim 2, wherein $R^1$ is —$(CH_2)_x$CH$_2$F and x is an integer between 2 and 10.

4. The compound of claim 2, wherein X is F, $R^1$ is

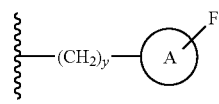

or $R^1$ is

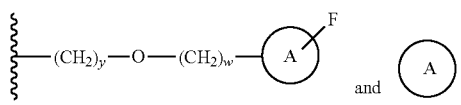

is phenyl or

is pyridyl.

5. The compound of claim 2, wherein $R^2$ is linear $C_{4-8}$alkyl.

6. The compound of claim 1, wherein the compound of Formula I(b) has the structure:

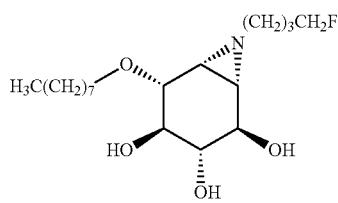

or

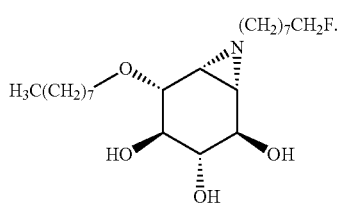

7. The compound of claim 1, wherein X is H, and $R^1$ is a group selected from:

—$(CH_2)_x$CH$_3$,

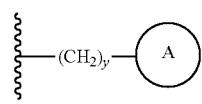

8. The compound of claim 7, wherein $R^1$ is —$(CH_2)_x$CH$_3$ and x is an integer between 2 and 10.

9. The compound of claim 7, wherein $R^1$ is

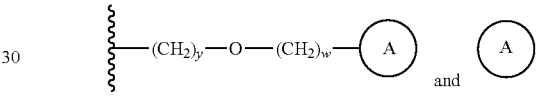

or $R^1$ is

is phenyl or is pyridyl.

10. The compound of claim 7, wherein $R^2$ is linear $C_{4-8}$alkyl.

11. The compound of claim 1, wherein the compound of Formula I(b) has the structure:

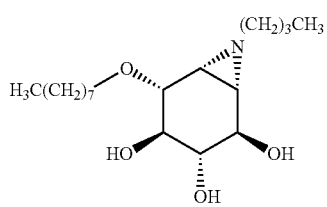

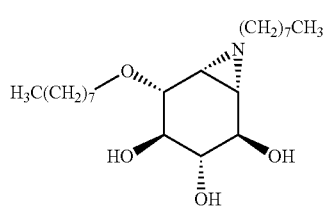

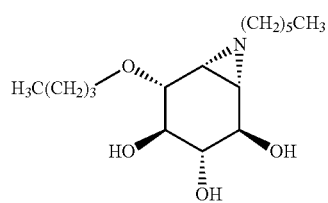

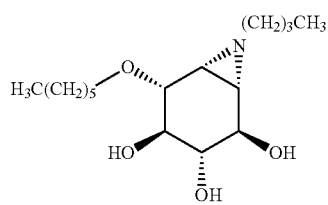

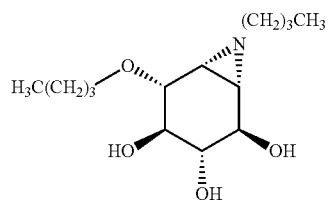

or

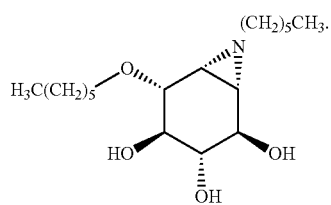

12. The compound of claim 1, wherein F is $^{18}$F.

13. A method for imaging β-glucocerebrosidase activity in a subject, the method comprising:
administering a compound as defined in claim 12 to the subject; and
detecting the presence of retained radioactivity in the subject using positron-emission tomography (PET).

14. The method of claim 13, wherein the imaging is for diagnosis of a disease associated with decreased β-glucocerebrosidase activity, or wherein the imaging is for monitoring the effect on β-glucocerebrosidase activity of a therapy for treatment of a disease associated with decreased β-glucocerebrosidase activity.

15. The method of claim 14, wherein the disease is Parkinson's disease or Gaucher disease.

16. The compound of claim 1, wherein the compound of Formula I(b) has the structure:

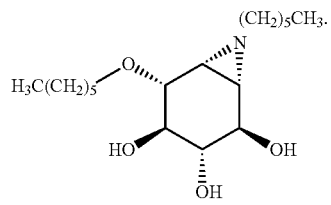

* * * * *

UNITED STATES PATENT AND TRADEMARK OFFICE
CERTIFICATE OF CORRECTION

PATENT NO. : 11,826,435 B2
APPLICATION NO. : 16/756872
DATED : November 28, 2023
INVENTOR(S) : Christopher Phenix et al.

Page 1 of 2

It is certified that error appears in the above-identified patent and that said Letters Patent is hereby corrected as shown below:

In the Claims

At Claim 1, Column 100, Lines 50-54, " 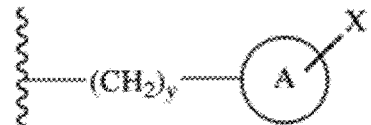 should read -- 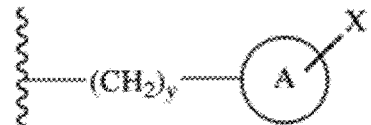 --.

At Claim 2, Column 100, Line 65, " 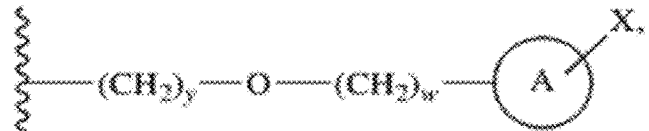 " should read -- 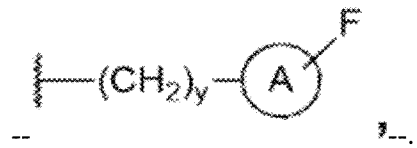 --.

At Claim 2, Column 101, Line 1, " 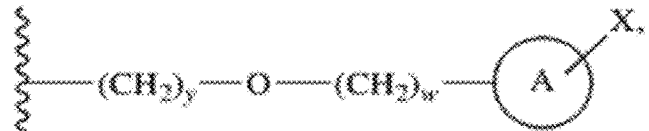 " should read -- 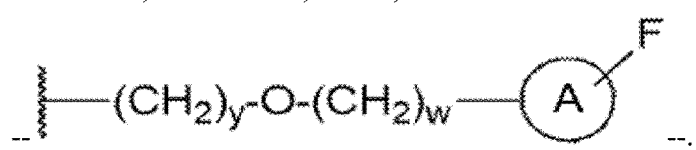 --.

Signed and Sealed this
Sixteenth Day of September, 2025

Coke Morgan Stewart
*Acting Director of the United States Patent and Trademark Office*

CERTIFICATE OF CORRECTION (continued)
U.S. Pat. No. 11,826,435 B2

At Claim 4, Column 101, Line 29, "is phenyl or Ⓐ is pyridyl." should read -- is phenyl or Ⓐ is pyridyl --.

At Claim 9, Column 102, Line 33, "is phenyl or Ⓐ is pyridyl." should read -- is phenyl or Ⓐ is pyridyl --.